US008592663B2

(12) United States Patent
Xu

(10) Patent No.: US 8,592,663 B2
(45) Date of Patent: *Nov. 26, 2013

(54) TOBACCO NICOTINE DEMETHYLASE GENOMIC CLONE AND USES THEREOF

(75) Inventor: Dongmei Xu, Glen Allen, VA (US)

(73) Assignee: U.S. Smokeless Tobacco Company LLC, Richmond, VA (US)

( * ) Notice: Subject to any disclaimer, the term of this patent is extended or adjusted under 35 U.S.C. 154(b) by 457 days.

This patent is subject to a terminal disclaimer.

(21) Appl. No.: 12/760,905

(22) Filed: Apr. 15, 2010

(65) Prior Publication Data

US 2011/0048437 A1 Mar. 3, 2011

Related U.S. Application Data

(60) Division of application No. 11/110,062, filed on Apr. 19, 2005, now Pat. No. 7,700,851, which is a continuation-in-part of application No. PCT/US2004/034065, filed on Oct. 15, 2004, and a continuation-in-part of application No. 10/934,944, filed on Sep. 3, 2004, now Pat. No. 7,812,227, which is a continuation-in-part of application No. 10/686,947, filed on Oct. 16, 2003, now abandoned, said application No. 11/110,062 is a continuation-in-part of application No. PCT/US2004/034218, filed on Oct. 15, 2004, and a continuation-in-part of application No. 10/943,507, filed on Sep. 17, 2004, now Pat. No. 7,855,318, and a continuation-in-part of application No. 10/934,944, said application No. 10/943,507 is a continuation-in-part of application No. 10/686,947, and a continuation-in-part of application No. 10/387,346, filed on Mar. 12, 2003, now abandoned, which is a continuation-in-part of application No. 10/340,861, filed on Jan. 10, 2003, now abandoned, which is a continuation-in-part of application No. 10/293,252, filed on Nov. 13, 2002, now abandoned.

(60) Provisional application No. 60/556,235, filed on Mar. 24, 2004, provisional application No. 60/566,235, filed on Apr. 29, 2004, provisional application No. 60/503,989, filed on Sep. 18, 2003, provisional application No. 60/485,368, filed on Jul. 8, 2003, provisional application No. 60/418,933, filed on Oct. 16, 2002, provisional application No. 60/363,684, filed on Mar. 12, 2002, provisional application No. 60/347,444, filed on Jan. 11, 2002, provisional application No. 60/337,684, filed on Nov. 13, 2001.

(51) Int. Cl.
C12N 15/82 (2006.01)
C12N 15/10 (2006.01)
C12N 15/00 (2006.01)
A01H 5/00 (2006.01)

(52) U.S. Cl.
USPC ..... 800/317.3; 800/278; 800/285; 435/320.1; 536/23.2

(58) Field of Classification Search
None
See application file for complete search history.

(56) References Cited

U.S. PATENT DOCUMENTS

| | | | |
|---|---|---|---|
| 4,693,976 | A | 9/1987 | Schilperoort et al. |
| 4,732,856 | A | 3/1988 | Federoff |
| 4,762,785 | A | 8/1988 | Comai |
| 4,801,540 | A | 1/1989 | Hiatt et al. |
| 4,801,541 | A | 1/1989 | Yoneda et al. |
| 4,940,838 | A | 7/1990 | Schilperoort et al. |
| 4,945,050 | A | 7/1990 | Sanford et al. |
| 5,004,863 | A | 4/1991 | Umbeck |
| 5,013,658 | A | 5/1991 | Dooner et al. |
| 5,034,322 | A | 7/1991 | Rogers et al. |
| 5,034,323 | A | 7/1991 | Jorgensen et al. |
| 5,104,310 | A | 4/1992 | Saltin |
| 5,107,065 | A | 4/1992 | Shewmaker et al. |
| 5,141,131 | A | 8/1992 | Miller, Jr. et al. |
| 5,149,645 | A | 9/1992 | Hoekema et al. |
| 5,159,135 | A | 10/1992 | Umbeck |
| 5,177,010 | A | 1/1993 | Goldman et al. |
| 5,231,019 | A | 7/1993 | Paszkowski et al. |
| 5,302,523 | A | 4/1994 | Coffee et al. |
| 5,352,605 | A | 10/1994 | Fraley et al. |
| 5,378,619 | A | 1/1995 | Rogers |
| 5,384,253 | A | 1/1995 | Krzyzek et al. |
| 5,463,174 | A | 10/1995 | Moloney et al. |
| 5,464,763 | A | 11/1995 | Schilperoort et al. |
| 5,464,765 | A | 11/1995 | Coffee et al. |
| 5,469,976 | A | 11/1995 | Burchell |
| 5,472,869 | A | 12/1995 | Krzyzek et al. |

(Continued)

FOREIGN PATENT DOCUMENTS

| | | |
|---|---|---|
| EP | 0 267 159 | 5/1988 |
| EP | 0 159 418 | 5/1990 |

(Continued)

OTHER PUBLICATIONS

U.S. Appl. No. 60/337,684, filed Nov. 13, 2001, Xu.

(Continued)

Primary Examiner — Brent T Page
(74) Attorney, Agent, or Firm — Fish & Richardson P.C.

(57) ABSTRACT

The present invention features tobacco nicotine demethylase nucleic acid and amino acid sequences, tobacco plants and plant components containing such sequences, including tobacco plants and plant components having reduced expression or altered enzymatic activity of nicotine demethylase, methods of use of nicotine demethylase sequences to create plants having altered levels of nornicotine or N'-nitrosonornicotine ("NNN") or both relative to a control plant, as well as tobacco articles having reduced levels of nornicotine or NNN.

25 Claims, 8 Drawing Sheets

(56) References Cited

U.S. PATENT DOCUMENTS

| | | | |
|---|---|---|---|
| 5,583,021 | A | 12/1996 | Dougherty et al. |
| 5,595,733 | A | 1/1997 | Carswell et al. |
| 5,614,399 | A | 3/1997 | Quail et al. |
| 5,641,664 | A | 6/1997 | D'Halluin et al. |
| 5,679,558 | A | 10/1997 | Gobel et al. |
| 5,712,135 | A | 1/1998 | D'Halluin et al. |
| 5,766,900 | A | 6/1998 | Shillito et al. |
| 5,929,304 | A | 7/1999 | Radin et al. |
| 6,002,070 | A | 12/1999 | D'Halluin et al. |
| 6,074,877 | A | 6/2000 | D'Halluin et al. |
| 6,730,832 | B1 | 5/2004 | Dominguez et al. |
| 6,907,887 | B2 | 6/2005 | Conkling |
| 6,953,040 | B2 | 10/2005 | Atchley et al. |
| 7,032,601 | B2 | 4/2006 | Atchley et al. |
| 7,184,992 | B1 | 2/2007 | Polyak et al. |
| 7,238,860 | B2 | 7/2007 | Ratcliffe et al. |
| 7,700,834 | B2 | 4/2010 | Xu et al. |
| 7,700,851 | B2 * | 4/2010 | Xu .............. 800/317.3 |
| 7,812,227 | B2 | 10/2010 | Xu |
| 7,884,263 | B2 | 2/2011 | Dewey et al. |
| 8,058,504 | B2 | 11/2011 | Xu |
| 8,188,337 | B2 | 5/2012 | Xu |
| 8,319,011 | B2 | 11/2012 | Xu et al. |
| 2002/0042934 | A1 | 4/2002 | Staub et al. |
| 2004/0103449 | A1 | 5/2004 | Xu |
| 2004/0111759 | A1 | 6/2004 | Xu |
| 2004/0117869 | A1 | 6/2004 | Xu |
| 2004/0162420 | A1 | 8/2004 | Xu |
| 2005/0132444 | A1 | 6/2005 | Xu |
| 2005/0160493 | A9 | 7/2005 | Ratcliffe et al. |
| 2005/0178398 | A1 | 8/2005 | Breslin et al. |
| 2005/0223442 | A1 | 10/2005 | Xu |
| 2005/0244521 | A1 | 11/2005 | Strickland et al. |
| 2006/0037096 | A1 | 2/2006 | Xu |
| 2006/0037623 | A1 | 2/2006 | Lawrence |
| 2006/0041949 | A1 | 2/2006 | Xu et al. |
| 2006/0185686 | A1 | 8/2006 | Lawrence |
| 2006/0191548 | A1 | 8/2006 | Strickland |
| 2007/0149408 | A1 | 6/2007 | Thomas et al. |
| 2007/0199097 | A1 | 8/2007 | Xu et al. |
| 2007/0292871 | A1 | 12/2007 | Xu |
| 2008/0076126 | A1 | 3/2008 | Xu |
| 2008/0182241 | A1 | 7/2008 | Xu |
| 2009/0205072 | A1 | 8/2009 | Dewey et al. |
| 2010/0218270 | A1 | 8/2010 | Xu et al. |
| 2010/0235938 | A1 | 9/2010 | Xu et al. |
| 2010/0235945 | A1 | 9/2010 | Xu et al. |
| 2011/0078817 | A1 | 3/2011 | Xu |
| 2012/0199148 | A1 | 8/2012 | Xu et al. |
| 2012/0233727 | A1 | 9/2012 | Xu |
| 2013/0074858 | A1 | 3/2013 | Xu et al. |
| 2013/0081157 | A1 | 3/2013 | Xu et al. |

FOREIGN PATENT DOCUMENTS

| | | |
|---|---|---|
| EP | 0 176 112 | 5/1990 |
| EP | 0 120 516 | 10/1991 |
| EP | 0 131 624 | 9/1992 |
| EP | 0 292 435 | 7/1995 |
| EP | 0 116 718 | 5/1996 |
| EP | 0 627 752 | 7/1997 |
| EP | 1 033 405 | 9/2000 |
| EP | 0 290 799 | 9/2004 |
| EP | 0 320 500 | 11/2004 |
| WO | WO 84/02919 | 8/1984 |
| WO | WO 87/06614 | 11/1987 |
| WO | WO 92/09696 | 6/1992 |
| WO | WO 93/21335 | 10/1993 |
| WO | WO 94/01930 | 1/1994 |
| WO | WO 02/072758 | 9/2002 |
| WO | WO 03/078577 | 9/2003 |
| WO | WO 2004/035745 | 4/2004 |
| WO | WO 2005/038018 | 4/2005 |
| WO | WO 2005/038033 | 4/2005 |
| WO | WO 2005/046363 | 5/2005 |
| WO | WO 2005/111217 | 11/2005 |
| WO | WO 2005/116199 | 12/2005 |
| WO | WO 2006/022784 | 3/2006 |
| WO | WO 2006/091194 | 8/2006 |
| WO | WO 2006/120570 | 11/2006 |
| WO | WO 2008/076802 | 6/2008 |

OTHER PUBLICATIONS

U.S. Appl. No. 60/347,444, filed Jan. 11, 2002, Xu.
U.S. Appl. No. 60/363,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 18, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/665,451, filed Mar. 24, 2005, Xu.
Asamizu et al., "A large scale analysis of cDNA in Arabidopsis thaliana: generation of 12,028 non-redundant expressed sequence tags from normalized and size-selected cDNA libraries," *DNA Res.*, 7(3):175-180, 2000.
Barik, "An intronic microRNA silences genes that are functionally antagonistic to its host gene," *Nucleic Acids Res.*, 36(16):5232-5241, 2008.
Boyette and Hamm, "Results of the Year 2000 TSNA sampling program in flue-cured tobacco," *Rec Adv Tob Sci.* 27:17-22, 2001.
Bozak et al., "Sequence analysis of ripening-related cytochrome P-450 cDNAs from avocado fruit," *Proc. Natl. Acad. Sci. USA*, 87(10):3904-3908, 1990.
Caruthers, "New Methods for Chemically Synthesizing Deoxyoligonucleotides," *Methods of DNA and RNA Sequencing*, Chapter 1, Weissman (ed.), Praeger Publishers, New York, pp. 1-22, 1983.
Chakrabarti et al., "CYP82E4-mediated nicotine conversion in tobacco is regulated by a senescence-specific signaling pathway" *Plant Mol Biol.*, 66(4):415-427, 2008.
EMBL Database Report for Accession No. EU 182719 dated Dec. 2, 2007, 2 pages.
Goldrick et al., "Molecular genetic analysis of the V kappa Ser group associated with two mouse light chain genetic markers. Complementary DNA cloning and southern hybridization analysis," *J Exp Med.*, 162(2):713-728, 1985.
Hayes et al., "Blotting techniques for the study of DNA, RNA, and proteins" *BMJ.*, 299(6705): 965-968, 1989.
Hecht and Hoffmann, "The relevance of tobacco-specific nitrosamines to human cancer," *Cancer Surveys*, 8(2): 273-294, 1989.
Hecht, "Biochemistry, biology, and carcinogenicity of tobacco-specific N-nitrosamines," *Chem. Res. Toxicol.*, 11(6): 559-603, 1998.
Hoffmann et al., "Tobacco-specific N-nitrosamines and Areca-derived N-nitrosamines: chemistry, biochemistry, carcinogenicity, and relevance to humans," *J. Toxicol. Environ. Health*, 41(1): 1-52, 1994.
Julio et al., "Targeted Mutation Breeding as a tool for tobacco crop improvement," presentation made in Oct. 2008, 15 pages.
McDougall et al., "Detection of viral DNA and RNA by in situ hybridization," *J. Histochem. Cytochem.*, 34(1):33-38, 1986
Ng et al., "Specific Detection and Confirmation of Campylobacter jejuni by DNA Hybridization and PCR," *Appl. Environ. Microbiol.*, 63(11):4558-4563, 1997.
Pauli et al., "Molecular cloning and functional heterologous expression of two alleles encoding (S)-N-methylcoclaurine 3'-hydroxylase (CYP80B1), a new methyl jasmonate-inducible cytochrome P-450-dependent mono-oxygenase of benzylisoquinoline alkaloid biosynthesis" *Plant J.* 13(6):793-801, 1998.
Petkova-Andonova et al., "CYP92B1, A cytochrome P450, expressed in petunia flower buds, that catalyzes monooxidation of long-chain fatty acids," *Biosci Biotechnol Biochem.* 66(9):1819-1828, 2002.
Seal et al., "Isolation of a Pseudomonas solanacearum—Specific DNA Probe by Subtraction Hybridization and Construction of Species-Specific Oligonucleotide Primers for Sensitive Detection by the

(56) References Cited

OTHER PUBLICATIONS

Polymerase Chain Reaction," *Appl. Environ. Microbiol.*, 58(11):3751-3758, 1992.
Sequence 6912f1 obtained from the Internet at http://mrg.psc.riken.go.jp/nicotiana/menu/069.html, on Aug. 29, 2007, document date unknown, 1 page.
Takeda et al., "Differentiation between Wild and Vaccine-Derived Strains of Poliovirus by Stringent Microplate Hybridization of PCR Products," *J. Clin. Microbiol.*, 32(1):202-204, 1994.
Takken et al., "A functional cloning strategy, based on a binary PVX-expression vector, to isolate HR-inducing cDNAs of plant pathogens." *The Plant Journal*, 24(2):275-283, 2000.
Vaucheret et al., "Post-transcriptional gene silencing in plants," *J. Cell Sci.*, 114:3083-3091, 2001.
Wernsman and Rufty, "Tobacco," Principles of cultivar development, vol. 2. "Crop species" Chapter 17, pp. 669-698, 1987.
Zwart et al., "Rapid Screening for Freshwater Bacterial Groups by Using Reverse Line Blot Hybridization," *Appl. Environ. Microbiol.*, 69(10):5875-5883, 2003.
GenBank Accession No. ABA07806, dated Mar. 7, 2005, 1 page.
GenBank Accession No. AEK08729 dated Feb. 23, 2005, 5 pages.
Office Action from U.S. Appl. No. 10/293,252, document dated Oct. 18, 2006.
Office Action from U.S. Appl. No. 10/686,947, document dated Oct. 30, 2006.
Office Action from U.S. Appl. No. 10/387,346, document dated Nov. 14, 2006.
Office Action from U.S. Appl. No. 10/340,861, document dated Nov. 14, 2006.
Office Action from U.S. Appl. No. 10/943,507, document dated May 4, 2007.
Office Action from U.S. Appl. No. 10/934,944, document dated Jun. 12, 2007.
GenBank Accession No. BAA35080, dated Sep. 26, 2000.
GenBank Accession No. AAK62347, dated Jun. 14, 2001.
EBI Accession AV557806, dated Jun. 16, 2000, 2 pages.
Sequence 6912f1 obtained from the Internet at http://mrg.psc.riken.go.jp/nicotiana/menu, on Aug. 13, 2007, document date unknown, 1 page.
Allen et al., "RNAi-mediated replacement of morphine with the nonnarcotic alkaloid reticuline in opium poppy," *Nat. Biotech.*, 2004, 22(12):1559-1566.
Alonso et al., "A *Hox* gene mutation that triggers nonsense-mediated RNA decay and affects alternative splicing during *Drosophila* development" *Nucleic Acids Research*, 31(14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt and Rank, "Colocalization of antisense RNAs and ribozymes with their target mRNAs," *Genome*, 1997, 40:785-797.
ARS-GRIN (PI 551280, http://www.ars-grin.gov/cgi-bin/npgs/acc/display.pl?1446216, accessed Feb. 2009).
Bak et al., "Transgenic tobacco and *Arabidopsis* plants expressing the two multifunctional sorghum cytochrome P450 enzymes, CYP79A1 and CYP71E1, are cyanogenic and accumulate metabolites derived from intermediates in Dhurrin biosynthesis," *Plant Physiol.*, 2000, 123:1437-1448.
Bartoszewski et al., "Cloning of a Wound Inducible *Lycopersicon esculentum* Cytochrome P450 Gene and Lack of Regeneration of Transgenic Plants with Sense or Antisense Constructs," *J. Am. Soc. Hort. Sci.*, 2002, 127(4):535-539.
Batard et al., "Increasing expression of P450 and P450-reductase proteins from monocots in heterologous systems" *Archives of Biochemistry and Biophysics*, 2000, 379:161-196.
Baulcombe, "Fast forward genetics based on virus-induced gene silencing," *Curr. Opin. Plant Biol.*, 1999, 2:109-113.
Bolitho et al., "Antisense apple ACC-oxidase RNA reduces ethylene production in transgenic tomato fruit," (1997) *Plant Science* 122: 91-99.

Bosher and Labouesse, "RNA interference: genetic wand and genetic watchdog," *Nat. Cell Biol.*, 2000, 2:E31-E36.
Branch, "A good antisense molecule is hard to find," *TIBS*, 1998, 23:45-50.
Brigneti et al., "Viral pathogenicity determinants are suppressors of transgene silencing in *Nicotiana benthamiana*," *EMBO J.*, 1998, 17(22):6739-6746.
Burns et al., "Large-scale analysis of gene expression, protein localization, and gene disruption in *Saccharomyces cerevisiae*," *Genes Dev.*, 1994, 8:1087-1105.
Burton et al. "Distribution of Tobacco Constituents in Tobacco Leaf Tissue. 1. Tobacco-specific nitrosamines, nitrate, nitrite, and alkaloids" *J. Agric. Food Chem.*, 1992, 20:1050-1055.
Burton et al., "Changes in Chemical Composition of Burley Tobacco During Senescence and Curing. 2. Acylated Pyridine Alkaloids," *J. Agric. Food Chem.*, 1988, 38(3):579-583.
Byers et al., "Killing the messenger: new insights into nonsense-mediated mRNA decay" *The Journal of Clinical Investigation*, 109(1):3-6 (2002).
Byzova et al., "Transforming petals into sepaloid organs in *Arabidopsis* and oilseed rape: implementation of the hairpin RNA-mediated gene silencing technology in an organ-specific manner," *Planta* 218:379-387 (2004).
Callis et al., "Introns increase gene expression in cultured maize cells," *Genes and Dev.*, 1987, 1:1183-1200.
Carron et al., "Genetic modification of condensed tannin biosynthesis in *Lotus corniculatus* .1. Heterologous antisense dihydroflavonol reductase down-regulates tannin accumulation in "hairy root" cultures," *Theoretical and Applied Genetics* 87(8): 1006-1015, 1994.
Caruthers, "New Methods for Chemically Synthesizing Deoxyoligonucleotides," *Methods of DNA and RNA Sequencing*, 1983, Chapter 1, Weissman (ed.), Praeger Publishers, New York.
Chai et al., "Reducing the maize amylopectin content through RNA interference manipulation," *Zhi Wu Sheng Li Yu Fen Zi Sheng Wu Xue Xue Buo* 31:625-630 (2005), Abstract Only.
Chakrabarti et al. "Inactivation of the cytochrome P450 gene CYP82E2 by degenerative mutations was a key event in the evolution of the alkaloid profile of modern tobacco" *New Phytologist*, 2007, 175(3):565-574.
Chao et al., "A silent mutation induces exon skipping in the phenylalanine hydroxylase gene in phenylketonuria," *Hum. Genet.*, 2001, 108:14-19.
Chappell, "Biochemistry and Molecular Biology of the Isoprenoid Biosynthetic Pathway in Plants," *Annu. Rev. Plant Physiol. Plant Mol. Biol.*, 1995, 46:521-547.
Chapple, "Molecular-Genetic Analysis of Plant Cytochrome P450-Dependent Monooxygenases," *Annu. Rev. Plant Physiol. Plant Mol. Biol.*, 1998, 49:311-343.
Chelvarajan et al., "Study of Nicotine Demethylation in *Nicotiana otophora*," *J. Agric. Food Chem.*, 1993, 41:858-862.
Cheung et al., "A Floral Transmitting Tissue-Specific Glycoprotein Attracts Pollen Tubes and Stimulates Their Growth," *Cell*, 1995, 82:383-393.
Chou et al., "Chromosome Rearrangements in *Arabidopsis thaliana* Generated Through Cre-*lox* Site Specific Recombination," *Plant and Animal Genome VII Conference Abstracts*, San Diego, Calif., Jan. 17-21, 1999. Abstract No. P133.
Chuang and Meyerowitz, "Specific and heritable genetic interference by double-stranded RNA in *Arabidopsis thaliana*," *Proc. Natl. Acad. Sci. USA*, 2000, 97(9):4985-4990.
Cogoni and Macino, "Post-transcriptional gene silencing across kingdoms," *Curr. Opin. Genet. Dev.*, 2000, 10:638-643.
Colbert et al., "High-throughput screening for induced point mutations" *Plant Physiology*, 126:480-484, (2001).
Colliver et al., "Differential modification of flavonoid and isoflavonoid biosynthesis with an antisense chalcone synthase construct in transgenic *Lotus corniculatus*," *Plant Mol. Biol.*, 1997, 35(4):509-522.
Crookshanks et al., 28.8% identical, found in the EST Database. Accession No. BF153877 from The Potato tuber transcriptome: analysis of 6077 expressed sequence tags, *FEBS Lett.*, 2001, 506(2):123-126.

(56) References Cited

OTHER PUBLICATIONS

D'Souza et al., "Missense and silent tau gene mutations cause frontotemporal dementia with parkinsonism-chromosome 17 type, by affecting multiple alternative RNA splicing regulatory elements" *Proc. Natl. Acad. Sci. USA*, 96:5598-5603 (1999).
Davuluri et al., "Fruit-specific RNAi-mediated suppression of DET1 enhances carotenoid and flavonoid content in tomatoes," *Nat. Biotechnol.* 23:890-895 (2005).
Dekeyser et al., "Transient Gene Expression in Intact and Organized Rice Tissues," *Plant Cell*, 1990, 2:591-602.
Dewey et al., Meeting Abstract dated Sep. 27, 2005, 1 page.
Dewey et al., Power point presentation "Functional characterization of the nicotine N-Demethylase gene of tobacco" *Philip Morris USA*, 21 pages, 2006.
Donato et al., "Fluorescence-Based Assays for Screening Nine Cytochrome P450 (P450) Activities in Intact Cells Expressing Individual Human P450 Enzymes," *Drug Metab. Dispos.*, 2004, 32(7):699-706.
Einset, "Differential expression of antisense in regenerated tobacco plants transformed with an antisense version of a tomato ACC oxidase gene," *Plant Cell Tissue and Organ Culture* 46(2): 137-141, 1996.
Elkind et al., "Abnormal plant development and down-regulation of phenylpropanoid biosynthesis in transgenic tobacco containing a heterologous phenylalanine ammonia-lyase gene," (1990). *Proc Natl Acad Sci U S A* 87(22):9057-61.
Escobar et al., "RNAi-mediated oncogene silencing confers resistance to crown gall tumorigenesis," *Proc. Natl. Acad. Sci.* USA 98: 13437-13442 (2001).
Falcón-Pérez et al., "Functional Domain Analysis of the Yeast ABC Transporter Ycf1p by Site-directed Mutagenesis," *J. Biol. Chem.*, 1999, 274(33):23584-23590.
Fang et al., "Multiple cis regulatory elements for maximal expression of the cauliflower mosaic virus 35S promoter in transgenic plants," *Plant Cell*, 1989, 1:141-150.
Fannin and Bush, "Nicotine demethylation in *Nicotiana*," *Med. Sci. Res.*, 1992, 20:807-808.
Faske et al., "Transgenic Tobacco Plants Expressing Pea Chloroplast Nmdh cDNA in Sense and Antisense Orientation," (1997) *Plant Physiol* 115(2): 705-715.
Fedoroff et al., "Cloning of the *bronze* locus in maize by a simple and generalizable procedure using the transposable controlling element *Activator* (Ac)," *Proc. Natl. Acad. Sci. USA*, 1984, 81:3825-3829.
Fire et al., "Potent and specific genetic interference by double-stranded RNA in *Caenorhabditis elegans*," *Nature*, 1998, 391:806-811.
Forsthoefel et al., "T-DNA Insertion Mutagenesis in *Arabidopsis*: Prospects and Perspectives," *Aust. J. Plant Physiol.*, 1992, 19:353-366.
Frank et al., "Cloning of Wound-Induced Cytochrome P450 Monooxygenases Expressed in Pea," *Plant Physiol.*, 1996, 110:1035-1046.
Freeman et al., "Quantitative RT-PCR: Pitfalls and Potential," *BioTechniques*, 1999, 26:112-122 and 124-125.
Fromm et al., "An octopine synthase enhancer element directs tissue-specific expression and binds ASF-1, a factor from tobacco nuclear extracts," *Plant Cell*, 1989, 1:977-984.
Gavilano and Siminszky, "Isolation and Characterization of the Cytochrome P450 Gene *CYP82E5v2* that Mediates Nicotine to Nornicotine Conversion in the Green Leaves of Tobacco," *Plant Cell Physiol.*, 2007, 48(11):1567-1574.
Gavilano et al. "Functional analysis of nicotine demethylase genes reveals insights into the evolution of modern tobacco" *Journal of Biological Chemistry*, 281(1):249-256 (2007).
Gavilano et al. "Genetic engineering of *Nicotiana tabacum* for reduced nornicotine content" *Journal of Agricultural and Food Chemistry*, 2006, 54:9071-9078
Ghosh, "Polyamines and plant alkaloids," *Indian J. Exp. Biol.*, 2000, 38:1086-1091.

Graham-Lorence and Peterson, "P450s: structural similarities and functional differences," *FASEB J.*, 1996, 10:206-214.
Guo et al., "Protein Tolerance to Random Amino Acid Change," *Proc. Natl. Acad. Sci. USA*, 2004, 101(25):9205-9210.
Hao and Yeoman, "Evidence in Favour of an Oxidative N-Demethylation of Nicotine to Nornicotine in Tobacco Cell Cultures," *J. Plant Physiol.*, 1998, 152:420-426.
Hao and Yeoman, "Mechanism of Nicotine N-Demethylation in Tobacco Cell Suspension Cultures," *Phytochemistry*, 1995, 477-482.
Hao and Yeoman, "Nicotine N-Demethylase in Cell-Free Preparations from Tobacco Cell Cultures," *Phytochemistry*, 1996, 42(2):325-329.
Hao et al., "Mechanism of Nicotine N-Demethylation in Tobacco Cell Suspension Cultures," Institute of Cell and Molecular Biology, the University of Edinburgh, 1995.
Haseloff and Gerlach, "Simple RNA enzymes with new and highly specific endoribonuclease activities," *Nature*, 1988, 334:585-591.
Hélène et al., "Control of Gene Expression by Triple Helix-Forming Oligonucleotides," *Ann. N.Y. Acad. Sci.*, 1992, 660:27-36.
Hélène, "The anti-gene strategy: control of gene expression by triplex-forming-oligonucleotides," *Anti-Cancer Drug Des.*, 1991, 6:569-584.
Helliwell et al., Funct. *Plant Biol.* 29:1217-1225 (2002).
Henikoff and Comai, "Single-Nucleotide Mutations for Plant Functional Genomics," *Annu. Rev. Plant Biol.*, 2003, 54:375-401.
Herbik et al., "Isolation, characterization and cDNA cloning of nicotianamine synthase from barley," (1999) *Eur J Biochem* 265(1): 231-9.
Hibino et al., "Increase of Cinnamaldehyde Groups in Lignin of Transgenic Tobacco Plants Carrying an Antisense Gene for Cinnamyl Alcohol Dehydrogenase," (1995) *Biosci. Biotec. Biochem* 59:929-931.
Hildering and Verkerk, "Chimeric Structure of the Tomato Plant After Seed Treatment with EMS and X-Rays," *The Use of Induced Mutations in Plant Breeding*, 1965, Pergamon Press, pp. 317-320.
Hill and Preiss, "Functional analysis of conserved histidines in ADP-glucose pyrophosphorylase from *Escherichia coli*," *Biochem. Biophys. Res. Commun.*, 1998, 244:573-577.
Hoekema et al., "A binary plant vector strategy based on separation of the *vir*- and T-region of the *Agrobacterium tumefaciens* Ti-plasmid," *Nature*, 1983, 303:179-180.
Ingelbrecht et al., "Posttranscriptional silencing of reporter transgenes in tobacco correlates with DNA methylation," *Proc. Natl. Acad. Sci. USA*, 1994, 91:10502-10506.
Isshiki et al., "Nonsense-mediated decay of mutant *waxy* mRNA in rice" *Plant Physiology*, 125:1388-1395 (2001).
Jack et al., "Relative stability of nicotine to nornicotine conversion in three burley cultivars," *Coresta Congress*, 2004, Kyoto, Agro-Phyto groups, Abstract AP2.
Jorgensen et al., "Chalcone synthase cosuppression phenotypes in petunia flowers: comparison of sense vs. antisense constructs and single-copy vs. complex T-DNA sequences," *Plant Mol. Biol.*, 1996, 31:957-973.
Kempin et al., "Targeted disruption in *Arabidopsis*," *Nature*, 1997, 389:802-803.
Keskin et al., "A new, structurally nonredundant, diverse data set of protein-protein interfaces and its implications," *Protein Science*, 2004, 13:1043-1055.
Klahre et al., "High molecular weight RNAs and small interfering RNAs induce systemic posttranscriptional gene silencing in plants," *Proc. Natl. Acad. Sci. USA* 99:11981-11986 (2002).
Klink and Wolniak, "The Efficacy of RNAi in the Study of the Plant Cytoskeleton," *J. Plant Growth Regul.*, 2000, 19:371-384.
Koornneef, "Classical mutagenesis in higher plants," *Mol. Plant Biol.*, 2002, Gilmartin and Bowler, ed., Oxford University Press, pp. 1-11.
Koshinsky et al., "Cre-*lox* site-specific recombination between *Arabidopsis* and tobacco chromosomes," *Plant J.*, 2000, 23(6):715-722.
Kusaba et al., "Low Glutelin content1: A Dominant Mutation That Suppresses the Glutelin Multigene Family via RNA Silencing in Rice," *Plant Cell* 15:1455-1467 (2003).

(56) References Cited

OTHER PUBLICATIONS

Lazar et al., "Transforming Growth Factor α: Mutation of Aspartic Acid 47 and Leucine 48 Results in Different Biological Activities," *Mol. Cell. Biol.*, 1988, 8(3):1247-1252.

Levin et al., "Methods of double-stranded RNA-mediated gene inactivation in *Arabidopsis* and their use to define an essential gene in methionine biosynthesis," *Plant Mol. Biol.* 44:759-775 (2000).

Liu et al., "High-Stearic and High-Oleic Cottonseed Oils Produced by Hairpin RNA-Mediated Post-Transcriptional Gene Silencing," *Plant Physiol.* 129:1732-1743 (2002).

Maher, "DNA Triple-Helix Formation: An Approach to Artificial Gene Repressors?" *BioEssays*, 1992, 14(12):807-815.

Matthew, "RNAi for plant functional genomics," *Comp Funct Genomics*, 2004, 5:240-244.

Maniatis et al., "Regulation of inducible and tissue-specific gene expression," *Science*, 1987, 236:1237-1245.

Maquat., "Nonsense-mediated mRNA decay," *Curr. Biol.*, 2002, 12(6):R196-R197.

McKinney et al., "Sequence-based identification of T-DNA insertion mutations in *Arabidopsis*: actin mutants *act2-1* and *act4-1*," *Plant J.*, 1995, 8(4):613-622.

Mesnard et al., "Evidence for the involvement of tetrahydrofolate in the demethylation of nicotine by *Nicotiana plumbaginifolia* cell-suspension cultures," *Planta*, 2002, 214:911-919.

Mette et al., "Transcriptional silencing and promoter methylation triggered by double-stranded RNA," *EMBO J.*, 2000, 19(19):5194-5201.

Mol et al., "Regulation of plant gene expression by antisense RNA," *FEBS Lett.*, 1990, 268(2):427-430.

Napoli et al., "Introduction of a Chimeric Chalcone Synthase Gene into Petunia Results in Reversible Co-Suppression of Homologous Genes *in trans*," *Plant Cell*, 1990, 2:279-289.

Needleman and Wunsch, "A General Method Applicable to the Search for Similarities in the Amino Acid Sequence of Two Proteins," *J. Mol. Biol.*, 1970, 48:443-453.

Nelson et al., "Comparative Genomics of Rice and *Arabidopsis*. Analysis of 727 Cytochrome P450 Genes and Pseudogenes from a Monocot and a Dicot," *Plant Physiol.*, 2004, 135:756-772.

Nelson et al., "Comparison of cytochrome P450 (*CYP*) genes from the mouse and human genomes, including nomenclature recommendations for genes, pseudogenes and alternative-splice variants," *Pharmacogenetics*, 2004, 14:1-18.

Nishihara et al., "Flavanoid components and flower color change in transgenic tobacco plants by suppression of chalcone isomerase gene," *FEBS Lett.* 579:6074-6078 (2005).

Odell et al., "Identification of DNA sequences required for activity of the cauliflower mosaic virus 35S promoter," *Nature*, 1985, 313:810-812.

Ogita et al., "Application of RNAi to confirm theobromine as the major intermediate for caffeine biosynthesis in coffee plants with potential for construction of decaffeinated varieties," *Plant Mol. Biol.* 54:931-941 (2004).

Ohshima et al., "Nucleotide sequence of the PR-1 gene of *Nicotiana tabacum*," *FEBS Lett.*, 1987, 225:243-246.

Oliver et al., "Inhibition of tobacco NADH-hydroxypyruvate reductase by expression of a heterologous antisense RNA derived from a cucumber cDNA: Implications for the mechanism of action of antisense RNAs," (1993). *Mol Gen Genet* 239(3): 425-34.

Pearson and Lipman, "Improved tools for biological sequence comparison," *Proc. Natl. Acad. Sci. USA*, 1988, 85:2444-2448.

Plant Variety Protection Office (USDA-AMS, Beltsville, MD, http://www.ars-grin.gov/cgi-bin/npgs/html/pvp.pl?Tobbaco, accessed Feb. 2009).

Puchta et al., "Two different but related mechanisms are used in plants for the repair of genomic double-strand breaks by homologous recombination," *Proc. Natl. Acad. Sci. USA*, 1996, 93:5055-5060.

Qin et al., "Cre recombinase-mediated site-specific recombination between plant chromosomes," *Proc. Natl. Acad. Sci. USA*, 1994, 91:1706-1710.

Ralston et al., "Cloning, Heterologous Expression, and Functional Characterization 5-*epi*-Aristolochene-1,3-Dihydroxylase from Tobacco (*Nicotiana tabacum*)," *Arch. Biochem. Biophys.*, 2001, 393(2):222-235.

Reid et al., "Studies on the Fermentation of Tobacco 1. The Microflora of Cured and Fermenting Cigar-leaf Tobacco," Bulletin 356, 1938, Pennsylvania Agricultural Experiment Station, State College, PA, 18 pages.

Rodermel et al., "Nuclear-Organelle Interactions: Nuclear Antisense Gene Inhibits Ribulose Biphosphate Carboxylase Enzyme Levels in Transformed Tobacco Plants," *Cell*, 1988, 55:673-681.

Rohr et al., "Tandem inverted repeat system for selection of effective transgenic RNAi strains of *Chlamydomonas*," *Plant J.*, 2004, 40:611-621.

Salehuzzaman et al., "Isolation and characterization of a cDNA encoding granule-bound starch synthase in cassava (*Manihot esculenta* Crantz) and its antisense expresssion in potato," (1993) *Plant Mol Biol* 23(5):947-62.

Schenk et al., "Coordinated plant defense responses in *Arabidopsis* revealed by microarray analysis," *Proc. Natl. Acad. Sci. USA*, 2000, 97(21):11655-11660.

Schnable et al., "Genetic recombination in plants," *Curr. Opin. Plant Biol.*, 1998, 1:123-129.

Schopfer and Ebel, "Identification of elicitor-induced cytochrome P450s of soybean (*Glycine max* L.) using differential display of mRNA," *Mol. Gen. Genet.*, 1998, 258:315-322.

Shah et al., "Expression of Silent Mutations in Disease Phenotype" Abstract for presentation at 11th International Congress of Human Genetics, 1 page, (2006).

Siminszky et al., "Conversion of nicotine to nornicotine in *Nicotiana tabacum* is mediated by CYP82E4, a Cytochrome P450 monooxygenase," *Proc. Natl. Acad. Sci. USA*, 2005, 102(41):14919-14924.

Siminszky et al., 17.6% identical, found in IDENTITY_NUC Database. Accession No. AEK 08729 from 2005WO-US005665, filed on Feb. 23, 2005.

Skarnes, "Entrapment Vectors: A New Tool for Mammalian Genetics," *Bio/Technology*, 1990, 8:827-831.

Smith and Waterman, "Comparison of Biosequences," *Adv. Appl. Math.*, 1981, 2:482-489.

Smith et al., "Total silencing by intron-spliced hairpin RNAs," *Nature*, 2000, 407:319-320.

Spradling et al., "Gene disruptions using *P* transposable elements: An integral component of the *Drosophila* genome project," *Proc. Natl. Acad. Sci. USA*, 1995, 92:10824-10830.

Stålberg et al., "Deletion analysis of a 2S seed storage protein promoter of *Brassica napus* in transgenic tobacco," *Plant Mol. Biol.*, 1993, 23:671-683.

Sundaresan et al., "Patterns of gene action in plant development revealed by enhancer trap and gene trap transposable elements," *Genes Dev.*, 1995, 9:1797-1810.

Takemoto et al., "Molecular Cloning of a Defense-Response-Related Cytochrome P450 Gene from Tobacco," *Plant Cell Physiol.*, 1999, 40(12):1232-1242.

Tang et al., "Using RNAi to improve plant nutritional value: from mechanism to application," TRENDS in Biotechnology, 22(9):463-69 (2004).

Tavernarakis et al., "Heritable and inducible genetic interference by double-stranded RNA encoded by transgenes," *Nat. Genet.*, 2000, 24:180-183.

Temple et al., "Modulation of glutamine synthetase gene expression in tobacco by the introduction of an alfalfa glutamine synthetase gene in sense and antisense orientation: molecular and biochemical analysis," (1993). *Mol Gen Genet* 236(2-3): 315-25.

Thomas et al., "Size constraints for targeting post-transcriptional gene silencing and for RNA—directed methylation in *Nicotiana benthamiana* using a potato virus X vector," *Plant J.*, 2001, 25(4):417-425.

Thornton et al., "From structure to function: Approaches and limitations," *Nature Structural Biology, Structural Genomics Supplement*, Nov. 2000, pp. 991-994.

Till et al., "Discovery of induced point mutations in maize genes by TILLING" *BMC Plant Biology*, 4:12 (2004).

(56) References Cited

OTHER PUBLICATIONS

Tobacco in the United States, *U.S. Department of Agriculture*, 32 pages, (1979).
Toscano et al. "A silent mutation (2939G>, exon 6; CYP2D6*59) leading to impaired expression and function of CYP2D6" *Pharmacogenet Genomics*, 16(10):767-70 (2006).
Trevanion et al., "NADP-Malate Dehydrogenase in the $C_4$ Plant *Flaveria bidentis*," *Plant Physiol* 113(4): 1153-1165 (1997).
Turner and Schuch, "Post-transcriptional gene-silencing and RNA interference: genetic immunity, mechanisms and applications," *J. Chem. Technol. Biotechnol.*, 2000, 75:869-882.
United States, "Tobacco in the United States," Miscellaneous Publication No. 867, 1979, U.S. Dept. of Agriculture, Agricultural Marketing Service.
Vaistij et al., "Spreading of RNA Targeting and DNA Methylation in RNA Silencing Requires Transcription of the Target Gene and a Putative RNA-Dependent RNA Polymerase," *Plant Cell* 14:857-867 (2002).
Van der Krol et al., "An anti-sense chalcone synthase gene in transgenic plants inhibits flower pigmentation," (1988) *Nature* 333: 866-869.
van der Krol et al., "Antisense genes in plants: an overview," *Gene*, 1988, 72:45-50.
Vaucheret et al., "Post-transcriptional gene silencing in plants," *J. Cell Sci.*, 2001, 114:3083-3091.
Veena et al., "Glyoxalase I from *Brassica juncea*: molecular cloning, regulation and its over-expression confer tolerance in transgenic tobacco under stress," (1999). *Plant Journal* 17(4): 385-395.
Verdaguer et al., "Functional organization of the cassava vein mosaic virus (CsVMV) promoter," *Plant Mol. Biol.*, 1998, 37(6):1055-1067.
Verkerk, "Chimerism of the tomato plant after seed irradiation with fast neutrons," *Neth. J. Agric. Sci.*, 1971, 19:197-203.
Voss et al., "The role of enhancers in the regulation of cell-type-specific transcriptional control," *Trends Biochem. Sci.*, 1986, 11(7):287-289.
Wang et al., "Elucidation of the functions of genes central to diterpene metabolism in tobacco trichomes using posttranscriptional gene silencing" *Planta*, 2003, 216:686-691.

Wang et al., "Isolation and characterization of the *CYP71D16* trichome-specific promoter from *Nicotiana tabacum* L.," *J. Exp. Botany*, 2002, 53(376):1891-1897.
Wang et al., "Suppression of a P450 hydroxylase gene in plant trichome glands enhances natural-product-based aphid resistance," *Nat. Biotechnol.*, 2001, 19:371-374.
Waterhouse et al., "Virus resistance and gene silencing in plants can be induced by simultaneous expression of sense and antisense RNA," *Proc. Natl. Acad. Sci. USA*, 1998, 95:13959-13964.
Weigel and Nilsson, "A developmental switch sufficient for flower initiation in diverse plants," *Nature*, 1995, 377:495-500.
Weising et al., "Foreign Genes in Plants: Transfer, Structure, Expression, and Applications," *Ann. Rev. Genetics*, 1988, 22:421-477.
Werck-Reichhart and Feyereisen, "Cytochromes P450: a success story," *Genome Biology*, 2000, 1(6):reviews3003.1-3003.9.
Werck-Reichhart et al., "Cytochromes P450," *The Arabidopsis Book*, 2002, 28 pages.
Wernsman and Matzinger, "Relative Stability of Alleles at the Nicotine Conversion Locus of Tobacco," *Tobacco Sci.*, 1970, 14:34-36.
Wesley et al., "Construct design for efficient, effective and high-throughput gene silencing in plants," *Plant J.* 27: 581-590 (2001).
Wetmur, "DNA Probes: Applications of the Principles of Nucleic Acid Hybridization," *Crit. Rev. Biol. Mol. Biol.*, 1991, 26:227-259.
Whitbred and Schuler, "Molecular Characterization of *CYP73A9* and *CYP82A1* P450 Genes Involved in Plant Defense in Pea," *Plant Physiol.*, 2000, 124:47-58.
Xiong et al., "Different effects on ACC oxidase gene silencing triggered by RNA interference in transgenic tomato," *Plant Cell* 23:639-646 (2004).
Xu et al., "Biochemical and molecular characterizations of nicotine demethylase in tobacco," *Physiologia Plantarum*, 2007, 129:307-319.
Authorized Officer Nora Lindner, International Preliminary Report on Patentability in PCT/US07/087386 mailed Jun. 25, 2009, 6 pages.
Authorized Officer Y. Keller, International Search Report and Written Opinion of the International Searching Authority in PCT/US2005/013650, mailed Dec. 20, 2006, 7 pages.
Authorized Officer Philippe Becamel, International Preliminary Report on Patentability in PCT?US2005/013650, issued Nov. 1, 2006, 6 pages.

* cited by examiner

```
FEATURES              Location/Qualifiers
    Total             1..6347
    5' Flanking Sequences  1..2009
    CDS               join   (2010..2948,3947..4561)
    Intron            2949..3946
    Product           Cytochrome P450
    3' UTR            4562..6347
    Translation
        MLSPIEAIVGLVTFTFLFFFLWTKKSQKPSKPLPPKIPGGWPVIGHLFHFNDDGDDRPLARKLGDLADKYGPVF
        TFRLGLPLVLVVSSYEAVKDCFSTNDAIFSNRPAFLYGDYLGYNNAMLFLANYGPYWRKNRKLVIQEVLSASRL
        EKFKHVRFARIQASIKNLYTRIDGNSSTINLTDWLEELNFGLIVKMIAGKNYESGKGDEQVERFKKAFKDFMIL
        SMEFVLWDAFPIPLFKWVDFQGHVKAMKRTFKDIDSVFQNWLEEHINKREKMEVNAEGNEQDFIDVVLSKMSNE
        YLGEGYSRDTVIKATVFSLVLDAADTVALHINWGMALLINNQKALTKAQEEIDTKVGKDRWVEESDIKDLVYLQ
        AIVKEVLRLYPPGPLLVPHENVEDCVVSGYHIPKGTRLFANVMKLQRDPKLWSDPDTFDPERFIATDIDFRGQY
        YKYIPFGSGRRSCPGMTYALQVEHLTMAHLIQGFNYRTPNDEPLDMKEGAGITIRKVNPVELIIAPRLAPELY BASE COUNT    2046 a    984 c   1163 g   2154 t 1 TCTCTAAAGT CCCCTTCCAC TTTATCTTAG CTGTGTGATT TCTTTCAGAC AACCTTATTT
   61 TTATTCAGAC TCTTATTTGT ATTATTCTAG AAGCTCGTGT ACTTGTGACA CCAGTTCTGG
  121 GATGGTATTT AGATATCGCT ATTATTTTGG CTTATTCACT TCAGTTCAGA TTTTATTCCA
  181 GTTATTTGAT TTCTTTATTA TTAATCAAAT TGAATTGTTA AAAATGGTTA AAATTACTCC
  241 AATGTTGGCT TTCCTAGTAA GCGAAATATC AGGCGCCATC ACGGTACCCG AAGGTGAGAA
  301 TTTCAGATCG TGACAGCCGC ATCTCAAGGG GTGTGATGTA ACAGTTTAC GATGGTGCAA
  361 GCATTAGTGG CTGCTTCGAC GACTTAAATC CGTAACTTAT AGATCACACG AATACAACTT
  421 TACTATTTTA ACACCCAGCA AATTCCTGAT AAAAACAATT CTAACATAGC ACATCAAAAT
  481 GTAAATGATT GAAGAAAAAG ATGACTTTTA CAACAGAGA AAAAAACAGT TACGTGTGGG
  541 GTTGAATAGA GATTGTGGCT ATGCTATTTC TAATATTGAA ATTCACCGAC TTTTTTAGTT
  601 CAATACGAAA AGAGTAAGTG AAAAGGTCTG AAAAGGAAAA GGACAATGCC TAAAAGGACA
  661 CATTCAGAAC ACATACACTG AATGATTCTA ATTTCTAGTC CGAAGATTTC TAGTTCGAGG
  721 ATAACGTGAG CAATCGGTTA CTTCCCATTA GCAATTGCCA ACTGGATGTT TGACTATTTA
  781 TGTTTCTGGC CAATAGAGGA GAGGAATACT ACGTTACGTA TGGAGTTTGA ACCCTTCACA
  841 TCAACTTATT AAGTGAGTTA TCCCTCAATC ACGATTCAAC TATGATTCCG CTAACTTCAA
  901 AGAATATTGA GTTAATTATT CAAATGATTA GTCCAAAATT ATTTAATAAA GTTATACTAT
  961 TTCTTTTATT TGTAACATAC ATCTTTTGTT TACATATTTA GTTAAATCTT AGCCCAACCC
 1021 TATCGTTGGT TCGACTTTTT TTCTTTTAAT TTTGATTTAT TCTGTTCGGT AATTTCGCTT
 1081 TGTTTGGCTT GAATAATAAC TAGTGCATAA AGTCATATAC TCTAATATTT TTAATTGAAG
 1141 TACTCACAAA TACAAAAATA AAAAACATTC TAAGCTCACA TGATAGTTGA CAAAATCTTT
 1201 ATCCAAAACA AGAGGCGGAG CCAGGATTTG AAACTTATGG GTTCAGAATT CTAAATCTCT
 1261 TAAGTTACTA GGTTCTAAAT TAATAATTTA TACATGTTCA ATGAATTTCT TAAGACAAAT
 1321 ACATAGTTTG AACGAAAGCT ACTGGGTTCG GCCGAATCCG TAAGTTATAC TCTCCCTCCG
 1381 CCCCGGTCCA AAACCAGCTA GTATCAATAG AGAGAGAGAG AGAGAGAGAG AGATAATAAA
 1441 TTTGACCATT GACAATGGCT TATTACTTGC TTAGAGTTAA TTGGTGAACT TAGAGAATAT
 1501 AATAAGGAAT ATTTAAACAG ATACGTCATC AATCCACGAG TAACGAAGTA AGAAATACCC
 1561 TAAAATCGTA GAAACATTGA GTTAAATTGC TTGACAGCCT ATCTAGTAAG AGTCAAAATC
 1621 TACTATCTAT CTTGTTCCGC CATTTTCTTA AAGAAGTACA TGAGCTTTAT CATCCACCTC
 1681 AACATGAATG CAAAAGAAAA TTATTGTGCA ACTTAATATG TTATAATCAA TGATATGTGT
 1741 CTTGTGTAAC AAAGTATATA TTTCGATACG ATATTAATAT GTAGGTGTTA TATTTTTAAA
 1801 TATCAAATAT CATACTTAAC ACCGATTTTT TAAAAACTTA GGCCAATTAC CCTACCAACT
 1861 AAAATACTGT ATATCAAACA CTAATGTTTT CTATTTCGGT ACGACAGTTC TCTATTTACC
 1921 ATATTATGGA ATTATGCCCA TCCTACAGTT ACCTATAAAA AGGAAGTTGC CGATAGTTAT
```

FIGURE 2-1

```
1981 ATTCTCAACT TCTTATCTAA AAATCCATAA TGCTTTCTCC CATAGAAGCC ATTGTAGGAC
2041 TAGTAACCTT CACATTTCTC TTCTTCTTCC TATGGACAAA AAAATCTCAA AAACCTTCAA
2101 AACCCTTACC ACCGAAAATC CCCGGAGGAT GGCCGGTAAT CGGCCATCTT TTCCACTTCA
2161 ATGACGACGG CGACGACCGT CCATTAGCTC GAAAACTCGG AGACTTAGCT GACAAATACG
2221 GCCCCGTTTT CACTTTTCGG CTAGGCCTTC CCCTTGTCTT AGTTGTAAGC AGTTACGAAG
2281 CTGTAAAAGA CTGTTTCTCT ACAAATGACG CCATTTTTTC CAATCGTCCA GCTTTTCTTT
2341 ACGGCGATTA CCTTGGCTAC AATAATGCCA TGCTATTTTT GGCCAATTAC GGACCTTACT
2401 GGCGAAAAAA TCGAAAATTA GTTATTCAGG AAGTTCTCTC CGCTAGTCGT CTCGAAAAAT
2461 TCAAACACGT GAGATTTGCA AGAATTCAAG CGAGCATTAA GAATTTATAT ACTCGAATTG
2521 ATGGAAATTC GAGTACGATA AATTTAACTG ATTGGTTAGA AGAATTGAAT TTTGGTCTGA
2581 TCGTGAAGAT GATCGCTGGA AAAAATTATG AATCCGGTAA AGGAGATGAA CAAGTGGAGA
2641 GATTTAAGAA AGCGTTTAAG GATTTATGA TTTTATCAAT GGAGTTTGTG TTATGGGATG
2701 CATTTCCAAT TCCATTATTT AAATGGGTGG ATTTTCAAGG GCATGTTAAG GCTATGAAAA
2761 GGACTTTTAA AGATATAGAT TCTGTTTTTC AGAATTGGTT AGAGGAACAT ATTAATAAAA
2821 GAGAAAAAAT GGAGGTTAAT GCAGAAGGGA ATGAACAAGA TTTCATTGAT GTGGTGCTTT
2881 CAAAAATGAG TAATCAATAT CTTGGTGAAG GTTACTCTCG TGATACTGTC ATTAAAGCAA
2941 CGGTGTTTGT AAGTTCATCT GTCATTTTTC ATTTATTCAC TTTTATTTTG AGGAGCAGAC
3001 ATGTTAATAA TAATTTGGAG CAACTGTAAA GTTATCTATG TGTACAGGTT CGAGCCTCAG
3061 GTGCAACCAC TAATGCTTGT ATTAGATTAT GTTGTCTGCA TCATACCCCT AATTGGAGTG
3121 TGGCTCTTCC CGAACCCTGC AATGCTGGAT GCTGGATGCT TTATGTATCA GACTGACCTT
3181 TTTGTTAAAC TATCTAAATA CTAAGGATGA TTTAATAAAA ATATAGAATG GTAAACAGAA
3241 AAAGATGAGA TTATTTTGG GGCTATATGG ATTCGCCCGG GCTTTGGGAG GTAAACGGT
3301 ATCTACCAGT TGAGACTTTA CTCCAGAACT TTATCTCGAG AGCTCTGAAT AAAAATGAAA
3361 TAGTATTTAC CACTCCAAAA TCTTTGATGG TAAAAGATG AGATATAACC TCTTATAATT
3421 GATTGAACCA CGTTGATAGA ATAAAACTTC TTTACTCCCA TTCAGCATAA GAAAAATGAA
3481 ACCAAACGGA ATTCTTCTCT TTTTAGGGG GAAATTCCTT AATTGCTTGT TGAATATAGA
3541 TTCATGTCGT TATTCTATTT TTAATAATGA TGAAAATCAA TATAGTCAAA GTTAATACTT
3601 ATGTCATTTG GTTGCGGAC AAGTTATATT GGAACTATAT AATACGTCTA TTATAGAATA
3661 GTGATTATTT AGAGGATATA CATTTTTTTT GGATAAATAT TTGATTTATT GGATTAAAAA
3721 TAGAATATAC AGGTAAGGTC TAAAACGTGT GTTTGCTTTT ACACTAAATA AACTTGACCT
3781 CGTACAATTC TAAGAAAATA TTTGAAATAA ATGAATTATT TTATTGTTAA TCAATTAAAA
3841 AAATCATAGT ATAGATGAGA TGTGTGCATA CTTGACAATA ACTATACTAA CTAAAACAAG
3901 GTATGTGAAT AATTGATATT CCTTTTTTAA TTATTCTTTT TTCCAGAGTT TGGTCTTGGA
3961 TGCAGCAGAC ACAGTTGCTC TTCACATAAA TTGGGGAATG GCATTATTGA TAAACAATCA
4021 AAAGGCCTTG ACGAAAGCAC AAGAAGAGAT AGACACAAAA GTTGGTAAGG ACAGATGGGT
4081 AGAAGAGAGT GATATTAAGG ATTTGGTATA CCTCCAAGCT ATTGTTAAAG AAGTGTTACG
4141 ATTATATCCA CCAGGACCTT TGTTAGTACC ACACGAAAAT GTAGAAGATT GTGTTGTTAG
4201 TGGATATCAC ATTCCTAAAG GGACAAGATT ATTCGCAAAC GTCATGAAAC TGCAACGTGA
4261 TCCTAAACTC TGGTCTGATC CTGATACTTT CGATCCAGAG AGATTCATTG CTACTGATAT
4321 TGACTTTCGT GGTCAGTACT ATAAGTATAT CCCGTTTGGT TCTGGAAGAC GATCTTGTCC
4381 AGGGATGACT TATGCATTGC AAGTGGAACA CTTAACAATG GCACATTTGA TCCAAGGTTT
4441 CAATTACAGA ACTCCAAATG ACGAGCCCTT GGATATGAAG GAAGGTGCAG GCATAACTAT
4501 ACGTAAGGTA AATCCTGTGG AACTGATAAT AGCGCCTCGC CTGGCACCTG AGCTTTATTA
4561 AAACCTAAGA TCTTTCATCT TGGTTGATCA TTGTATAATA CTCCTAAATG GATATTCATT
4621 TACCTTTTAT CAATTAATTG TCAGTACGAG TTTTTCTAAT TTGGTACATT TGTAATAATA
4681 AGTAAAGAAT AATTGTGCTA ATATATAAAG GTTTGTAGAA GATAATTGAC TGGTTGTACC
4741 ACAATCTCCA GTGAAAGTGT TAATTATTTA CTTGATCCAC AGCTTATTCT ATGTTTGAAA
4801 TTTGCCTAGT GTCATGATAT TACTCCATCA AATTCAAGAA ATAATCATTT CCAACTTTTG
4861 CTGGACTGGA CGATCTTTCA ATAATAAAGG ATCTTAATT TGCCAAAGTT GAGATCAAAA
4921 TACTGGTCGC TTTACCAATA AGAATGAAAT GTGATGGAAA TTATGTACGT GGGATAAGG
4981 GAACACAACT ATCAAGGAGA CTAAAGGTA CGTAAAGGAA AAGAAAAAAT TGCCATTGA
5041 TTGCTACTAA GTAACCTAAC AAAATCTTTC AGAAAAGAAT CACTTGTATA AGTCGGGGTT
5101 GAAAGTTTTG GTGTCTCTTT TCTTATGTAT TGTTGTCTTT AGACAGTATT GTACTTAGTT
5161 ATTTCAGAAT TTTATTTTCG TATTAGAGCT CAAGACTCTG TATTTATTAG TTCTGGGAGA
5221 ATTATCATGT ATTTTCAGTC TTTTGTTATT TCTGTAAATT CCGCTATTTT GGTTCTTTAT
5281 TGCTATGTTC GGCTTTCCTA GAAATGTGT TAGGCGCTAT CACGACTGAT TGAGATTTTG
5341 TATCGTGACT GATAATTACA CGGTTTAGTA AATTTTGATA TTTTCAAAAA GAGTTTTTTT
```

FIGURE 2-2

```
5401 AATAAAATAT GCAACTTCAG TCAAAACATA CAACGTTTTG TTGTATAAAT CCGATCAAAA
5461 CATATAACTT ACATAAAACT TGCGTATGAA TTTTTTGTTG TATAAACATT TGGTTAAAAC
5521 ATATAACTTA CATATAATTT GCATACAACT TACATAAAAC TTGCATATAA ACAATTTATT
5581 TATGTCTTTG TTTTTGAGTA TCAATTTGAA ATTCCAACAA AAACAAACTC TAATTTTTAC
5641 CAAACTCTCT CAAAATTGAG TTATAGATTT CAAAAGATAT CCTTAATCGT TTGCAATTGT
5701 AACAATCCGA TCGGCCGTTT TGAGATCTAG CGTGTTGTTT GGCGGTTTGA GACCTTGAGT
5761 AACTTCACTT TATGTTGTAT GACTTGTATA TGTGGTCGGA ATTAAATTTC GGGAAGTTCA
5821 GAGTTGATTC GGATGAAAAA TTCTAATTTC GGAAGTTTTA AGATGGAATG ATTGACTAAG
5881 GATTGACGTT TGAGTAAACG ATCTCGGAAT CGAGATTTGA AGGTTCCAAT AGGTTCGTAT
5941 GATGATTTCA GACTTGAGCG TATGTTTGGG TTGAGTATCG GGTGGTCCGG GAGCATTTCA
6001 ACGCTGATTA TAGAAAATTG GCATCTTAAA GGTTTTAGAA TTTCATAAGT TTGGTTTGAA
6061 GTGGATTTTG ATATTATCGG TGTCCATTTG GAGTTTCGAG CCTTGGAATA GGTTCGTATC
6121 GTAAATTTTG ACTTTAGTGT AAAGTTCGGC GTCATTCCGG AGTGTTTTGA TAAGATTCTG
6181 ATGCGTTCGT CGAAGTTTGG AAGTTTGAAA GTTGAAAAGA AGATTTTTAA TAGGCGATTC
6241 ATGATTTTGA TGTTATTTGT GTCGAGCCTT TGGATAAGTT TGTGTGAGGT ATGGGACTTG
6301 TTGGTATGAA TGGACGAGCT CTACGGGGGC CTCGAGTAAG TTTCGGA
```

Figure 2-3

Tobacco Nicotine Demethylase Gene Coding Sequences

```
BASE COUNT      489 a     275 c     333 g     457 t
       1 ATGCTTTCTC CCATAGAAGC CATTGTAGGA CTAGTAACCT TCACATTTCT CTTCTTCTTC
      61 CTATGGACAA AAAAATCTCA AAAACCTTCA AAACCCTTAC CACCGAAAAT CCCCGGAGGA
     121 TGGCCGGTAA TCGCCATCT TTTCCACTTC AATGACGACG GCGACGACCG TCCATTAGCT
     181 CGAAAACTCG GAGACTTAGC TGACAAATAC GGCCCCGTTT TCACTTTTCG GCTAGGCCTT
     241 CCCCTTGTCT TAGTTGTAAG CAGTTACGAA GCTGTAAAAG ACTGTTTCTC TACAAATGAC
     301 GCCATTTTTT CCAATCGTCC AGCTTTTCTT TACGGCGATT ACCTTGGCTA CAATAATGCC
     361 ATGCTATTTT TGGCCAATTA CGGACCTTAC TGGCGAAAAA ATCGAAAATT AGTTATTCAG
     421 GAAGTTCTCT CCGCTAGTCG TCTCGAAAAA TTCAAACACG TGAGATTTGC AAGAATTCAA
     481 GCGAGCATTA AGAATTTATA TACTCGAATT GATGGAAATT CGAGTACGAT AAATTTAACT
     541 GATTGGTTAG AAGAATTGAA TTTTGGTCTG ATCGTGAAGA TGATCGCTGG AAAAAATTAT
     601 GAATCCGGTA AAGGAGATGA ACAAGTGGAG AGATTTAAGA AAGCGTTTAA GGATTTTATG
     661 ATTTTATCAA TGGAGTTTGT GTTATGGGAT GCATTTCCAA TTCCATTATT TAAATGGGTG
     721 GATTTTCAAG GGCATGTTAA GGCTATGAAA AGGACTTTTA AAGATATAGA TTCTGTTTTT
     781 CAGAATTGGT TAGAGGAACA TATTAATAAA AGAGAAAAAA TGGAGGTTAA TGCAGAAGGG
     841 AATGAACAAG ATTTCATTGA TGTGGTGCTT TCAAAAATGA GTAATGAATA TCTTGGTGAA
     901 GGTTACTCTC GTGATACTGT CATTAAAGCA ACGGTGTTTA GTTTGGTCTT GGATGCAGCA
     961 GACACAGTTG CTCTTCACAT AAATTGGGGA ATGGCATTAT TGATAAACAA TCAAAAGGCC
    1021 TTGACGAAAG CACAAGAAGA GATAGACACA AAAGTTGGTA AGGACAGATG GGTAGAAGAG
    1081 AGTGATATTA AGGATTTGGT ATACCTCCAA GCTATTGTTA AAGAAGTGTT ACGATTATAT
    1141 CCACCAGGAC CTTTGTTAGT ACCACACGAA ATGTAGAAG ATTGTGTTGT TAGTGGATAT
    1201 CACATTCCTA AAGGGACAAG ATTATTCGCA AACGTCATGA AACTGCAACG TGATCCTAAA
    1261 CTCTGGTCTG ATCCTGATAC TTTCGATCCA GAGAGATTCA TTGCTACTGA TATTGACTTT
    1321 CGTGGTCAGT ACTATAAGTA TATCCCGTTT GGTTCTGGAA GACGATCTTG TCCAGGGATG
    1381 ACTTATGCAT TGCAAGTGGA ACACTTAACA ATGGCACATT TGATCCAAGG TTTCAATTAC
    1441 AGAACTCCAA ATGACGAGCC CTTGGATATG AAGGAAGGTG CAGGCATAAC TATACGTAAG
    1501 GTAAATCCTG TGGAACTGAT AATAGCGCCT CGCCTGGCAC CTGAGCTTTA TTAA
```

Tobacco Nicotine Demethylase Gene Deduced Amino Acids

```
       1 MLSPIEAIVG LVTFTFLFFF LWTKKSQKPS KPLPPKIPGG WPVIGHLFHF NDDGDDRPLA
      61 RKLGDLADKY GPVFTFRLGL PLVLVVSSYE AVKDCFSTND AIFSNRPAFL YGDYLGYNNA
     121 MLFLANYGPY WRKNRKLVIQ EVLSASRLEK FKHVRFARIQ ASIKNLYTRI DGNSSTINLT
     181 DWLEELNFGL IVKMIAGKNY ESGKGDEQVE RFKKAFKDFM ILSMEFVLWD AFPIPLFKWV
     241 DFQGHVKAMK RTFKDIDSVF QNWLEEHINK REKMEVNAEG NEQDFIDVVL SKMSNEYLGE
     301 GYSRDTVIKA TVFSLVLDAA DTVALHINWG MALLINNQKA LTKAQEEIDT KVGKDRWVEE

361 SDIKDLVYLQ AIVKEVLRLY PPGPLLVPHE NVEDCVVSGY HIPKGTRLFA NVMKLQRDPK
     421 LWSDPDTFDP ERFIATDIDF RGQYYKYIPF GSGRRSCPGM TYALQVEHLT MAHLIQGFNY
     481 RTPNDEPLDM KEGAGITIRK VNPVELIIAP RLAPELY
```

FIGURE 3

Tobacco Nicotine Demethylase gene intron (998 nt)

```
  1 GTAAGTTCAT CTGTCATTTT TCATTTATTC ACTTTTATTT TGAGGAGCAG ACATGTTAAT
 61 AATAATTTGG AGCAACTGTA AAGTTATCTA TGTGTACAGG TTCGAGCCTC AGGTGCAACC
121 ACTAATGCTT GTATTAGATT ATGTTGTCTG CATCATACCC CTAATTGGAG TGTGGCTCTT
181 CCCGAACCCT GCAATGCTGG ATGCTGGATG CTTTATGTAT CAGACTGACC TTTTTGTTAA
241 ACTATCTAAA TACTAAGGAT GATTTAATAA AAATATAGAA TGGTAAACAG AAAAAGATGA
301 GATTATTTTT GGGGCTATAT GGATTCGCCC GGGCTTTGGG AGGTAAAACG GTATCTACCA
361 GTTGAGACTT TACTCCAGAA CTTTATCTCG AGAGCTCTGA ATAAAAATGA AATAGTATTT
421 ACCACTCCAA AATCTTTGAT GGTAAAAAGA TGAGATATAA CCTCTTATAA TTGATTGAAC
481 CACGTTGATA GAATAAAACT TCTTTACTCC CATTCAGCAT AAGAAAAATG AAACCAAACG
541 GAATTCTTCT CTTTTTTAGG GGGAAATTCC TTAATTGCTT GTTGAATATA GATTCATGTC
601 GTTATTCTAT TTTTAATAAT GATGAAAATC AATATAGTCA AAGTTAATAC TTATGTCATT
661 TGGTTTGCGG ACAAGTTATA TTGAACTAT ATAATACGTC TATTATAGAA TAGTGATTAT
721 TTAGAGGATA TACATTTTTT TTGATAAAT ATTTGATTTA TTGGATTAAA AATAGAATAT
781 ACAGGTAAGG TCTAAAACGT GTGTTTGCTT TTACACTAAA TAAACTTGAC CTCGTACAAT
841 TCTAAGAAAA TATTTGAAAT AAATGAATTA TTTTATTGTT AATCAATTAA AAAAATCATA
901 GTATAGATGA GATGTGTGCA TACTTGACAA TAACTATACT AACTAAAACA AGGTATGTGA
961 ATAATTGATA TTCCTTTTTT AATTATTCTT TTTTCCAG
```

FIGURE 4

Tobacco Nicotine Demethylase gene promoter (2009 nt)

```
   1 TCTCTAAAGT CCCCTTCCAC TTTATCTTAG CTGTGTGATT TCTTTCAGAC AACCTTATTT
  61 TTATTCAGAC TCTTATTTGT ATTATTCTAG AAGCTCGTGT ACTTGTGACA CCAGTTCTGG
 121 GATGGTATTT AGATATCGCT ATTATTTTGG CTTATTCACT TCAGTTCAGA TTTTATTCCA
 181 GTTATTTGAT TTCTTTATTA TTAATCAAAT TGAATTGTTA AAAATGGTTA AAATTACTCC
 241 AATGTTGGCT TTCCTAGTAA GCGAAATATC AGGCGCCATC ACGGTACCCG AAGGTGAGAA
 301 TTTCAGATCG TGACAGCCGC ATCTCAAGGG GTGTGATGTA AACAGTTTAC GATGGTGCAA
 361 GCATTAGTGG CTGCTTCGAC GACTTAAATC CGTAACTTAT AGATCACACG AATACAACTT
 421 TACTATTTTA ACACCCAGCA AATTCCTGAT AAAAACAATT CTAACATAGC ACATCAAAAT
 481 GTAAATGATT GAAGAAAAAG ATGACTTTTA TAGACAGAGA AAAAAACAGT TACGTGTGGG
 541 GTTGAATAGA GATTGTGGCT ATGCTATTTC TAATATTGAA ATTCACCGAC TTTTTTAGTT
 601 CAATACGAAA AGAGTAAGTG AAAAGGTCTG AAAAGGAAAA GGACAATGCC TAAAAGGACA
 661 CATTCAGAAC ACATACACTG AATGATTCTA ATTTCTAGTC CGAAGATTTC TAGTTCGAGG
 721 ATAACGTGAG CAATCGGTTA CTTCCCATTA GCAATTGCCA ACTGGATGTT TGACTATTTA
 781 TGTTTCTGGC CAATAGAGGA GAGGAATACT ACGTTACGTA TGGAGTTTGA ACCCTTCACA
 841 TCAACTTATT AAGTGAGTTA TCCCTCAATC ACGATTCAAC TATGATTCCG CTAACTTCAA
 901 AGAATATTGA GTTAATTATT CAAATGATTA GTCCAAAATT ATTTAATAAA GTTATACTAT
 961 TTCTTTTATT TGTAACATAC ATCTTTTGTT TACATATTTA GTTAAATCTT AGCCCAACCC
1021 TATCGTTGGT TCGACTTTTT TTCTTTTAAT TTTGATTTAT TCTGTTCGGT AATTTCGCTT
1081 TGTTTGGCTT GAATAATAAC TAGTGCATAA AGTCATATAC TCTAATATTT TTAATTGAAG
1141 TACTCACAAA TACAAAAATA AAAAACATTC TAAGCTCACA TGATAGTTGA CAAAATCTTT
1201 ATCCAAAACA AGAGGCGGAG CCAGGATTTG AAACTTATGG GTTCAGAATT CTAAATCTCT
1261 TAAGTTACTA GGTTCTAAAT TAATAATTTA TACATGTTCA ATGAATTTCT TAAGACAAAT
1321 ACATAGTTTG AACGAAAGCT ACTGGGTTCG GCCGAATCCG TAAGTTATAC TCTCCCTCCG
1381 CCCCGGTCCA AAACCAGCTA GTATCAATAG AGAGAGAGAG AGAGAGAGAG AGATAATAAA
1441 TTTGACCATT GACAATGGCT TATTACTTGC TTAGAGTTAA TTGGTGAACT TAGAGAATAT
1501 AATAAGGAAT ATTTAAACAG ATACGTCATC AATCCACGAG TAACGAAGTA AGAAATACCC
1561 TAAAATCGTA GAAACATTAC GTTAAATTGC TTGACAGCCT ATCTAGTAAG AGTCAAAATC
1621 TACTATCTAT CTTGTTCCGC CATTTCTTA AAGAAGTACA TGAGCTTTAT CATCCACCTC
1681 AACATGAATG CAAAAGAAAA TTATTGTGCA ACTTAATATG TTATAATCAA TGATATGTGT
1741 CTTGTGTAAC AAAGTATATA TTTCGATACG ATATTAATAT GTAGGTGTTA TATTTTTAAA
1801 TATCAAATAT CATACTTAAC ACCGATTTTT TAAAAACTTA GGCCAATTAC CCTACCAACT
1861 AAAATACTGT ATATCAAACA CTAATGTTTT CTATTTCGGT ACGACAGTTC TCTATTTACC
1921 ATATTATGGA ATTATGCCCA TCCTACAGTT ACCTATAAAA AGGAAGTTGC CGATAGTTAT
1981 ATTCTCAACT TCTTATCTAA AAATCCATA
```

FIGURE 5

Tobacco Nicotine Demethylase gene 3' UTR

```
   1 AACCTAAGAT CTTTCATCTT GGTTGATCAT TGTATAATAC TCCTAAATGG ATATTCATTT
  61 ACCTTTTATC AATTAATTGT CAGTACGAGT TTTTCTAATT TGGTACATTT GTAATAATAA
 121 GTAAAGAATA ATTGTGCTAA TATATAAAGG TTTGTAGAAG ATAATTGACT GGTTGTACCA
 181 CAATCTCCAG TGAAAGTGTT AATTATTTAC TTGATCCACA GCTTATTCTA TGTTTGAAAT
 241 TTGCCTAGTG TCATGATATT ACTCCATCAA ATTCAAGAAA TAATCATTTC CAACTTTTGC
 301 TGGACTGGAC GATCTTTCAA TAATAAAGGA TCTTTAATTT GCCAAAGTTG AGATCAAAAT
 361 ACTGGTCGCT TTACCAATAA GAATGAAATG TGATGGAAAT TATGTACGTT GGGATAAGGG
 421 AACACAACTA TCAAGGAGAC TAAAAGGTAC GTAAAGGAAA AGAAAAAATT TGCCATTGAT
 481 TGCTACTAAG TAACCTAACA AAATCTTTCA GAAAAGAATC ACTTGTATAA GTCGGGGTTG
 541 AAAGTTTTGG TGTCTCTTTT CTTATGTATT GTTGTCTTTA GACAGTATTG TACTTAGTTA
 601 TTTCAGAATT TTATTTTCGT ATTAGAGCTC AAGACTCTGT ATTTATTAGT TCTGGGAGAA
 661 TTATCATGTA TTTTCAGTCT TTTGTTATTT CTGTAAATTC CGCTATTTTG GTTCTTTATT
 721 GCTATGTTCG GCTTTCCTAG AAAATGTGTT AGGCGCTATC ACGACTGATT GAGATTTTGT
 781 ATCGTGACTG ATAATTACAC GGTTAGTAAA ATTTTGATAT TTTCAAAAAG AGTTTTTTTA
 841 ATAAAATATG CAACTTCAGT CAAAACATAC AACGTTTTGT TGTATAAATC CGATCAAAAC
 901 ATATAACTTA CATAAAACTT GCGTATGAAT TTTTTGTTGT ATAAACATTT GGTTAAAACA
 961 TATAACTTAC ATATAATTTG CATACAACTT ACATAAAACT TGCATATAAA CAATTTATTT
1021 ATGTCTTTGT TTTTGAGTAT CAATTTGAAA TTCCAACAAA AACAAACTCT AATTTTTACC
1081 AAACTCTCTC AAAATTGAGT TATAGATTTC AAAAGATATC CTTAATCGTT TGCAATTGTA
1141 ACAATCCGAT CGGCCGTTTT GAGATCTAGC GTGTTGTTTG GCGGTTTGAG ACCTTGAGTA
1201 ACTTCACTTT ATGTTGTATG ACTTGTATAT GTGGTCGGAA TTAAATTTCG GGAAGTTCAG
1261 AGTTGATTCG GATGAAAAAT TCTAATTTCG GAAGTTTTAA GATGGAATGA TTGACTAAGG
1321 ATTGACGTTT GAGTAAACGA TCTCGGAATC GAGATTTGAA GGTTCCAATA GGTTCGTATG
1381 ATGATTTCAG ACTTGAGCGT ATGTTTGGGT TGAGTATCGG GTGGTCCGGG AGCATTTCAA
1441 CGCTGATTAT AGAAAATTGG CATCTTAAAG GTTTTAGAAT TTCATAAGTT TGGTTTGAAG
1501 TGGATTTTGA TATTATCGGT GTCCATTTGG AGTTTCGAGC CTTGGAATAG GTTCGTATCG
1561 TAAATTTTGA CTTTAGTGTA AAGTTCGGCG TCATTCCGGA GTGTTTGAT AAGATTCTGA
1621 TGCGTTCGTC GAAGTTTGGA AGTTGAAAG TTGAAAAGAA GATTTTAAT AGGCGATTCA
1681 TGATTTTGAT GTTATTTGTG TCGAGCCTTT GGATAAGTTT GTGTGAGGTA TGGGACTTGT
1741 TGGTATGAAT GGACGAGCTC TACGGGGCC TCGAGTAAGT TTCGGA
```

TOBACCO NICOTINE DEMETHYLASE GENOMIC CLONE AND USES THEREOF

CROSS-REFERENCE TO RELATED APPLICATIONS

The present application claims the benefit of U.S. Provisional Application No. 60/665,451, filed Mar. 24, 2005, U.S. Provisional Application No. 60/665,097, filed Mar. 24, 2005, U.S. Provisional Application No. 60/646,764, filed Jan. 25, 2005, U.S. Provisional Application No. 60/607,357, filed Sep. 3, 2004, and U.S. Provisional Application No. 60/566,235, filed Apr. 29, 2004.

The present application is also a divisional of U.S. application Ser. No. 11/110,062, filed Apr. 19, 2005, now U.S. Pat. No. 7,700,851, which is a continuation-in-part of PCT/US2004/034065, filed Oct. 15, 2004, which claims the benefit of U.S. Application No. 60/556,235, filed Apr. 29, 2004, and which is a continuation-in-part of U.S. application Ser. No. 10/934,944, filed Sep. 3, 2004, which, in turn, is a continuation-in-part of U.S. application Ser. No. 10/686,947, filed Oct. 16, 2003. U.S. application Ser. No. 11/110,062, filed Apr. 19, 2005, is also a continuation-in-part of PCT/US2004/034218, filed Oct. 15, 2004, which claims the benefit of U.S. Application No. 60/566,235, filed Apr. 29, 2004, and which is a continuation-in-part of U.S. application Ser. No. 10/943,507, filed Sep. 17, 2004, and which is also a continuation-in-part application of U.S. application Ser. No. 10/934,944 filed, Sep. 3, 2004 and U.S. application Ser. No. 10/943,507, filed Sep. 17, 2004, each of which is a continuation-in-part of U.S. application Ser. No. 10/686,947, filed Oct. 16, 2003, which, in turn, claims the benefit of U.S. Provisional Application No. 60/503,989, filed Sep. 18, 2003, U.S. Provisional Application No. 60/485,368, filed Jul. 8, 2003, and U.S. Provisional Application No. 60/418,933, filed Oct. 16, 2002. U.S. application Ser. No. 10/686,947, filed Oct. 16, 2003 is a continuation-in-part of U.S. application Ser. No. 10/387,346, filed Mar. 12, 2003, which, in turn, is a continuation-in-part of U.S. application Ser. No. 10/340,861, filed Jan. 10, 2003, which, in turn, is a continuation-in-part of U.S. application Ser. No. 10/293,252, filed Nov. 13, 2002, which claims the benefit of U.S. Provisional Application No. 60/363,684, filed Mar. 12, 2002, U.S. Provisional Application No. 60/347,444, filed Jan. 11, 2002, and U.S. Provisional Application No. 60/337,684, filed on Nov. 13, 2001. All of the applications listed are incorporated herein by reference.

BACKGROUND

Cytochrome p450s catalyze enzymatic reactions for a diverse range of chemically dissimilar substrates that include the oxidative, peroxidative, and reductive metabolism of endogenous and xenobiotic substrates. In plants, p450s participate in biochemical pathways that include the synthesis of plant products such as phenylpropanoids, alkaloids, terpenoids, lipids, cyanogenic glycosides, and glucosinolates (Chappell, Annu Rev. Plant Physiol. Plant Mol. Biol. 46:521-547, 1995). Cytochrome p450s, also known as p450 hemethiolate proteins, usually act as terminal oxidases in multicomponent electron transfer chains, called p450-containing monooxygenase systems. Specific reactions catalyzed by these enzyme systems include demethylation, hydroxylation, epoxidation, N-oxidation, sulfooxidation, N-, S-, and 0-dealkylations, desulfation, deamination, and reduction of azo, nitro, and N-oxide groups.

The diverse role of Nicotiana plant p450 enzymes has been implicated in effecting a variety of plant metabolites such as phenylpropanoids, alkaloids, terpenoids, lipids, cyanogenic glycosides, glucosinolates, and a host of other chemical entities. Some p450 enzymes can impact the composition of plant metabolites. For example, it has been long desired to improve the flavor and aroma of certain plants by altering a plant's profile of selected fatty acids through breeding; however very little is known about mechanisms involved in controlling the levels of these leaf constituents. The down regulation or up regulation of p450 enzymes associated with the modification of fatty acids may facilitate accumulation of desired fatty acids that provide more preferred leaf phenotypic qualities.

The function of p450 enzymes and their broadening roles in plant constituents is still being discovered. For instance, a special class of p450 enzymes was found to catalyze the breakdown of fatty acid into volatile C6- and C9-aldehydes and 13-alcohols that are major contributors of "fresh green" odor of fruits and vegetables. The level of other novel targeted p450s may be altered to enhance the qualities of leaf constituents by modifying lipid composition and related breakdown metabolites in Nicotiana leaf. Several of these constituents in leaf are affected by senescence that stimulates the maturation of leaf quality properties. Still other reports have shown that p450s enzymes are play a functional role in altering fatty acids that are involved in plant-pathogen interactions and disease resistance.

In other instances, p450 enzymes have been suggested to be involved in alkaloid biosynthesis. As provided in patent applications by Applicant, from which the present application claims priority, and which are incorporated by reference herein, nornicotine, a minor alkaloid found in Nicotiana tabacum, is produced by the p450-mediated demethylation of nicotine followed by acylation and nitrosation at the N position thereby producing a series of N-acylnornicotines and N-nitrosonornicotines. N-demethylation, catalyzed by a p450 demethylase, is thought to be a primary source of nornicotine biosynthesis in Nicotiana.

There exists a need in the art for reagents and methods for modifying plant phenotypes. In particular, there exists a need for reagents and methods for modifying nicotine demethylase. The present invention provides a number of strategies for modifying expression of a nicotine demethylase.

SUMMARY OF THE INVENTION

The present inventors have identified and characterized a genomic clone of nicotine demethylase from tobacco. Included herein are sequences for the nicotine demethylase protein coding region, the 3' untranslated region ("3' UTR"), a single intron, and the nicotine demethylase gene promoter along with its transcriptional regulatory sequences (FIG. 1). Further described is the use of these sequences to create transgenic plants having altered levels of nornicotine or N'-nitrosonornicotine ("NNN") or both relative to a control plant.

Accordingly, in the first aspect, the invention features an isolated nucleic acid molecule, for example, a DNA sequence, containing a nucleotide sequence encoding a nicotine demethylase. In desirable embodiments, the nucleotide sequence of the first aspect is substantially identical to a nucleotide sequence encoding a tobacco nicotine demethylase, such as a tobacco nicotine demethylase containing a nucleotide sequence that is at least 70% identical to the nucleotide sequence of SEQ ID NO:1 or SEQ ID NO:3, or that contains nucleotides 2010-2949 and/or 3947-4562 of SEQ ID NO:1, or that contains the sequence of SEQ ID NO:1 or SEQ ID NO:3. The isolated nucleic acid molecule of the first aspect of the invention, for example, is operably linked to a promoter functional in a plant cell and desirably is contained in an expression vector. In other desirable embodiments, the expression vector is contained in a cell, e.g., a plant cell. Desirably, the plant cell, such as a tobacco plant cell, is included in a plant. In another desirable embodiment, the invention features a seed, e.g., a tobacco seed, from a plant containing the expression vector, where the seed includes an isolated nucleic acid molecule that hybridizes under stringent conditions to the sequence of SEQ ID NO:3 operably linked to a heterologous promoter sequence. Furthermore, the invention features a plant derived from a germinated seed containing the expression vector, a leaf, either green or cured, from the plant, and an article of manufacture made from the leaf.

In another desirable embodiment, the nucleotide sequence contains a sequence that hybridizes under stringent conditions to the complement of the nucleotide sequence of SEQ ID NO:1 and/or SEQ ID NO:3, or to a fragment of SEQ ID NO:1 or SEQ ID NO:3. Desirably, the nucleotide sequence encodes a nicotine demethylase that is substantially identical to the amino acid sequence of SEQ ID NO:2. In a further desirable embodiment of the first aspect of the invention, the nicotine demethylase has at least 70% amino acid sequence identity to the nicotine demethylase amino acid sequence of SEQ ID NO:2 or to a fragment of a nicotine demethylase having altered (e.g., reduced) enzymatic activity as compared to the full-length polypeptide. Desirably, the nicotine demethylase includes the amino acid sequence of SEQ ID NO:2.

In another aspect, the invention features an isolated nucleic acid molecule containing a promoter that hybridizes under stringent conditions to the sequence of SEQ ID NO:6, or a fragment thereof that drives transcription. Desirably, the promoter (i) is induced following treatment with ethylene or during senescence; and (ii) includes (a) base pairs 1-2009 of SEQ ID NO:1, or (b) at least 200 consecutive base pairs identical to 200 consecutive base pairs of the sequence defined by base pairs 1-2009 of SEQ ID NO:1, or (c) a 20 base pair nucleotide portion identical in sequence to a 20 consecutive base pair portion of the sequence set forth in base pairs 1-2009 of SEQ ID NO:1.

A further aspect of the invention features an isolated nucleic acid promoter containing a nucleotide sequence having 50% or more sequence identity with the sequence of SEQ ID NO:6. Desirably, this isolated nucleic acid promoter is induced following treatment with ethylene or during senescence and, for example, includes the sequence of SEQ ID NO:6. Alternatively, the promoter may include a fragment obtainable from SEQ ID NO:6, where the fragment drives transcription of a heterologous gene or reduces or alters nicotine demethylase enzymatic activity (for example, silences gene expression). In a desirable embodiment the promoter sequence is operably linked to a heterologous nucleic acid sequence, and may, for example be contained in an expression vector. In other desirable embodiments the expression vector is contained in a cell, e.g., a plant cell. Desirably, the plant cell, such as a tobacco plant cell, is included in a plant. In another desirable embodiment, the invention features a seed, e.g., a tobacco seed, from a plant containing the expression vector, where the seed includes an isolated nucleic acid molecule that hybridizes under stringent conditions to the sequence of SEQ ID NO:6 operably linked to a heterologous nucleic acid sequence. Furthermore, the invention features a plant derived from a germinated seed containing the promoter of this aspect of the invention, a leaf, either green or cured, from the plant, and an article of manufacture made from the leaf.

Another aspect of the invention features a method of expressing a heterologous gene in a plant. This method involves (i) introducing into a plant cell a vector containing a promoter sequence having 50% or more sequence identity with the sequence of SEQ ID NO:6 operably linked to a heterologous nucleic acid sequence; and (ii) regenerating a plant from the cell. In addition, this method may involve sexually transmitting the vector to progeny and, further, may include the step of collecting the seed produced by the progeny.

In yet another aspect, the invention features a method of reducing expression of nicotine demethylase in a tobacco plant. This method includes the steps of (i) introducing into the tobacco plant a vector containing the sequence of SEQ ID NO:6 or a fragment obtainable from SEQ ID NO:6 operably linked to a heterologous nucleic acid sequence and (ii) expressing the vector in the tobacco plant. In a desirable embodiment of this method, expression of the nicotine demethylase is silenced. In other desirable embodiment, the vector expresses RNA, such as antisense RNA or an RNA molecule capable of inducing RNA interference (RNAi).

In a further desirable aspect, the invention features an isolated nucleic acid molecule containing an intron that hybridizes under stringent conditions to the sequence of SEQ ID NO:5, or a fragment thereof that reduces or alters nicotine demethylase enzymatic activity (for example, silences gene expression) or can serve as a molecular marker to identify nicotine demethylase nucleic acid sequences. In a desirable embodiment, the intron includes (a) base pairs 2950-3946 of SEQ ID NO:1, or (b) at least 200 consecutive base pairs identical to 200 consecutive base pairs of the sequence defined by base pairs 2950-3946 of SEQ ID NO:1, or (c) a 20 base pair nucleotide portion identical in sequence to a 20 consecutive base pair portion of the sequence set forth in base pairs 2950-3946 of SEQ ID NO:1.

Another desirable aspect of the invention features an isolated nucleic acid intron including a nucleotide sequence having 50% or more sequence identity with the sequence of SEQ ID NO:5, or a fragment thereof that reduces or alters nicotine demethylase enzymatic activity (for example, silences gene expression) or can serve as a molecular marker to identify nicotine demethylase nucleic acid sequences. Silencing gene expression may, for example, involve homologous recombination or a mutation that results in a gene product that does not have nicotine demethylase activity. In particular, the intron may include the sequence of SEQ ID NO:5 or a fragment obtainable from SEQ ID NO:5. Desirably, an isolated nucleic acid molecule including an intron is operably linked to a heterologous nucleic acid sequence and this sequence desirably is included in an expression vector. In another embodiment, the expression vector is contained in a cell, such as a plant cell. In particular, the cell may be a tobacco cell. A plant, e.g., a tobacco plant, including a plant cell plant containing the sequence of SEQ ID NO:5 or a fragment obtainable from SEQ ID NO:5 operably linked to a heterologous nucleic acid sequence in an expression vector is another desirable embodiment of the present invention. Further, a seed, for example, a tobacco seed, from a plant, where the seed contains an intron that hybridizes under stringent conditions to SEQ ID NO:5 operably linked to a heterologous nucleic acid sequence is also desirable. Furthermore, the invention features a plant derived from the germinated seed containing the intron of this aspect of the invention, a leaf, either green or cured, from the plant, and an article of manufacture made from the green or cured leaf.

A further aspect of the invention features a method of expressing an intron in a plant. This method involves (i) introducing into a plant cell an expression vector containing the sequence of SEQ ID NO:5 or a fragment obtainable from SEQ ID NO:5 operably linked to a heterologous nucleic acid sequence; and (ii) regenerating a plant from the cell. In a desirable embodiment, this method also involves (iii) sexually transmitting the vector to progeny, and may include the additional step of collecting the seed produced by the progeny. The method desirably includes, for example, regenerating a plant from the germinated seed, a leaf, either green or cured, from the plant, and a method of making an article of manufacture from the leaf.

In yet another aspect, the invention features a method of reducing expression of nicotine demethylase in a tobacco plant. This method includes the steps of (i) introducing into the tobacco plant a vector containing the sequence of SEQ ID NO:5 or a fragment obtainable from SEQ ID NO:5 operably linked to a heterologous nucleic acid sequence and (ii) expressing the vector in the tobacco plant. In a desirable embodiment of this method, expression of the nicotine demethylase is silenced. In other desirable embodiment, the vector expresses RNA, such as antisense RNA or an RNA molecule capable of inducing RNA interference (RNAi).

In an additional aspect, the invention features an isolated nucleic acid molecule containing an untranslated region that hybridizes under stringent conditions to the sequence of SEQ ID NO:7 or a fragment thereof that can alter the expression pattern of a gene, reduces or alters nicotine demethylase enzymatic activity (for example, silences gene expression), or can be used as a marker to identify nicotine demethylase nucleic acid sequences. In a desirable embodiment of this aspect of the invention, the untranslated region includes (a) base pairs 4563-6347 of SEQ ID NO:1, or (b) at least 200 consecutive base pairs identical to 200 consecutive base pairs of the sequence defined by base pairs 4563-6347 of SEQ ID NO:1, or (c) a 20 base pair nucleotide portion identical in sequence to a 20 consecutive base pair portion of the sequence set forth in base pairs 4563-6347 of SEQ ID NO:1.

An additional desirable aspect of the invention features an isolated nucleic acid untranslated region containing a nucleotide sequence having 50% or more sequence identity with the sequence of SEQ ID NO:7. Desirably, the untranslated region includes the sequence of SEQ ID NO:7 or the untranslated region includes a fragment obtainable from SEQ ID NO:7 that can alter the expression pattern of a gene, reduces or alters nicotine demethylase enzymatic activity (for example, silences gene expression), or can be used as a marker to identify nicotine demethylase nucleic acid sequences. The untranslated region desirably is operably linked to a heterologous nucleic acid sequence and may be contained in an expression vector. Further, this expression vector is desirably contained in a cell, such as a plant cell, e.g., a tobacco cell. Another desirable embodiment of the invention features a plant, such as a tobacco plant, including a plant cell containing a vector that includes an isolated nucleic acid sequence that has 50% or more sequence identity with the sequence of SEQ ID NO:7 and is operably linked to a heterologous nucleic acid sequence.

The invention also features a seed, for example, a tobacco seed, from a plant, where the seed includes an untranslated region that hybridizes under stringent conditions to SEQ ID NO:7 operably linked to a heterologous nucleic acid sequence. Furthermore, the invention features a plant derived from a germinated seed containing the untranslated region of this aspect of the invention, a leaf, either green or cured, from the plant, and an article of manufacture made from the green or cured leaf.

In a further aspect, the invention features a method of expressing an untranslated region in a plant. This method involves (i) introducing into a plant cell a vector containing an isolated nucleic acid sequence that has 50% or more sequence identity with the sequence of SEQ ID NO: 7 and is operably linked to a heterologous nucleic acid sequence; and (ii) regenerating a plant from the cell. In addition, this method may also involve (iii) sexually transmitting the vector to progeny, and desirably, includes the additional step of collecting the seed produced by the progeny. The method desirably includes regenerating a plant from the germinated seed, a leaf, either green or cured, from the plant, and a method of making an article of manufacture made from the green or cured leaf.

Furthermore, the invention features a method of reducing expression or altering the enzymatic activity of nicotine demethylase in a tobacco plant. This method includes the steps of (i) introducing into the tobacco plant a vector containing an isolated nucleic acid sequence that has 50% or more sequence identity with the sequence of SEQ ID NO:7 and is operably linked to a heterologous nucleic acid sequence and (ii) expressing the vector in the tobacco plant. Desirably, expression of the nicotine demethylase is silenced. In other desirable embodiments the vector expresses RNA, e.g., antisense RNA or an RNA molecule capable of inducing RNA interference (RNAi).

Another aspect of the invention features an expression vector including a nucleic acid molecule containing a nucleotide sequence encoding a nicotine demethylase, where the vector is capable of directing expression of the nicotine demethylase encoded by the isolated nucleic acid molecule. Desirably, the vector includes the sequence of SEQ ID NO:1 or SEQ ID NO:3. In other desirable embodiments, the invention features a plant or plant component, e.g., a tobacco plant or plant component (e.g., a tobacco leaf or stem), that includes a nucleic acid molecule containing a nucleotide sequence encoding a polypeptide that demethylates nicotine.

A further aspect of the invention features a cell containing an isolated nucleic acid molecule that includes a nucleotide sequence encoding a nicotine demethylase. Desirably this cell is a plant cell or a bacterial cell, such as an *Agrobacterium*.

Another aspect of the invention features a plant or plant component (e.g., a tobacco leaf or stem) containing an isolated nucleic acid molecule that encodes a nicotine demethylase, where the nucleic acid molecule is expressed in the plant or the plant component. Desirably, the plant or plant component is an angiosperm, a dicot, a solanaceous plant, or a species of *Nicotiana*. Other desirable embodiments of this aspect are a seed or a cell from the plant or plant component, as well as a leaf, either green or cured, derived from the plant and an article of manufacture made therefrom.

In an additional aspect, the invention features a tobacco plant having reduced expression of a nucleic acid sequence encoding a polypeptide, for example, one that includes the sequence of SEQ ID NO:2, and that demethylates nicotine, where the reduced expression (or a reduction in enzymatic activity) reduces the level of nornicotine in the plant. In a desirable embodiment, the tobacco plant is a transgenic plant, such as one that includes a transgene that, when expressed in the transgenic plant, silences gene expression of an endogenous tobacco nicotine demethylase.

In particular, the transgenic plant desirably includes one or more of the following: a transgene that expresses an antisense molecule of a tobacco nicotine demethylase or an RNA molecule capable of inducing RNA interference (RNAi); a transgene that, when expressed in the transgenic plant, co-suppresses expression of a tobacco nicotine demethylase; a transgene that encodes a dominant negative gene product, e.g., a mutated form the amino acid sequence of SEQ ID NO:2; a point mutation in a gene that encodes the amino acid sequence of SEQ ID NO:2; a deletion in a gene that encodes a tobacco nicotine demethylase; and an insertion in a gene that encodes a tobacco nicotine demethylase.

In other desirable embodiments, reduced expression of a nucleic acid sequence encoding a polypeptide occurs at the transcriptional level, at the translational level, or at the post-translational level.

Another aspect of the invention features a tobacco plant containing a recombinant expression cassette stably integrated into the genome thereof, where the cassette is capable of effecting a reduction in nicotine demethylase activity. Seeds of this tobacco plant are featured in a desirable embodiment. Other desirable embodiments include leaf, either green or cured, derived from this plant and an article of manufacture made therefrom.

A further aspect of the invention features a method of expressing a tobacco nicotine demethylase in a plant. This method involves (i) introducing into a plant cell an expression vector including a nucleic acid molecule containing a nucleotide sequence encoding a nicotine demethylase; and (ii) regenerating a plant from the cell. In a desirable embodiment, this method features sexually transmitting the vector to progeny, and desirably also includes the additional step of collecting the seed produced by the progeny. Additional desirable embodiments include a plant derived from the germinated seed, a leaf, either green or cured, from the plant, and an article of manufacture made from the green or cured leaf.

An additional aspect of the invention features a substantially pure tobacco nicotine demethylase. Desirably, this tobacco nicotine demethylase includes an amino acid sequence having at least 70% identity to the amino acid sequence of SEQ ID NO:2 or includes the amino acid sequence of SEQ ID NO:2. In a desirable embodiment, the tobacco nicotine demethylase, upon expression in a plant cell, converts nicotine to nornicotine. In other desirable embodiments, the tobacco nicotine demethylase, upon expression in a plant cell, is predominantly localized in leaves, or the tobacco nicotine demethylase is induced by ethylene or is expressed during plant senescence.

In a further aspect, the invention features a substantially pure antibody that specifically recognizes and binds to a tobacco nicotine demethylase. Desirably, the antibody recognizes and binds to a recombinant tobacco nicotine demethylase, e.g., one containing the sequence of SEQ ID NO:2 or a fragment thereof.

Another aspect of the invention features a method of producing a tobacco nicotine demethylase. This method involves the steps of: (a) providing a cell transformed with an isolated nucleic acid molecule containing a nucleotide sequence encoding a polypeptide that demethylates nicotine; (b) culturing the transformed cell under conditions for expressing the isolated nucleic acid molecule; and (c) recovering the tobacco nicotine demethylase. The invention also features a recombinant tobacco nicotine demethylase produced according to this method.

In an additional aspect, the invention features a method of isolating a tobacco nicotine demethylase or fragment thereof. This method involves the steps of: (a) contacting the nucleic acid molecule of SEQ. ID NOS:1, 3, 5, 6, or 7 or a portion thereof with a nucleic acid preparation from a plant cell under hybridization conditions providing detection of nucleic acid sequences having at least 70% or greater sequence identity to the nucleic acid sequence of SEQ ID NOS:1, 3, 5, 6, or 7; and (b) isolating the hybridizing nucleic acid sequences.

In a further aspect, the invention features another method of isolating a tobacco nicotine demethylase or fragment thereof. This method includes the steps of: (a) providing a sample of plant cell DNA; (b) providing a pair of oligonucleotides having sequence identity to a region of a nucleic acid molecule having the sequence of SEQ ID NOS:1, 3, 5, 6, or 7; (c) contacting the pair of oligonucleotides with the plant cell DNA under conditions suitable for polymerase chain reaction-mediated DNA amplification; and (d) isolating the amplified tobacco nicotine demethylase or fragment thereof. In a desirable embodiment of this aspect, the amplification step is carried out using a sample of cDNA prepared from a plant cell. In another desirable embodiment, the tobacco nicotine demethylase encodes a polypeptide which is at least 70% identical to the amino acid sequence of SEQ ID NO:2.

A further aspect of the invention features a method for reducing the expression of tobacco nicotine demethylase in a plant or plant component. This method involves the steps of: (a) introducing into plant cells a transgene encoding a tobacco nicotine demethylase operably linked to a promoter functional in the plant cells to yield transformed plant cells; and (b) regenerating a plant or plant component from the transformed plant cells, where the tobacco nicotine demethylase is expressed in the cells of the plant or plant component, thereby reducing the expression of tobacco nicotine demethylase in a plant or plant component. In particular embodiments of this aspect of the invention, the transgene encoding the tobacco nicotine demethylase is constitutively expressed or inducibly expressed, for example, in a tissue-specific, cell-specific, or organ-specific manner. In another embodiment of this aspect of the invention, expression of the transgene co-suppresses the expression of an endogenous tobacco nicotine demethylase.

A further aspect of the invention features another method for reducing the expression of tobacco nicotine demethylase in a plant or plant component. This method includes the steps of: (a) introducing into plant cells a transgene encoding an antisense coding sequence of a tobacco nicotine demethylase or an RNA molecule capable of inducing RNA interference (RNAi) operably linked to a promoter functional in the plant cells to yield transformed plant cells; and (b) regenerating a plant or plant component from the transformed plant cells, where the antisense or an RNA molecule capable of inducing RNA interference (RNAi) of the coding sequence of the tobacco nicotine demethylase is expressed in the cells of the plant or plant component, thereby reducing the expression of tobacco nicotine demethylase in a plant or plant component. Desirably, the transgene encoding an antisense sequence or an RNA molecule capable of inducing RNA interference (RNAi) of a tobacco nicotine demethylase is constitutively expressed or is inducibly expressed, for instance in a tissue-specific, cell-specific, or organ-specific manner.

An additional aspect of the invention features yet another method for reducing the expression of tobacco nicotine demethylase in a plant or plant component. This method involving the steps of: (a) introducing into plant cells a transgene encoding a dominant negative gene product of a tobacco nicotine demethylase operably linked to a promoter functional in the plant cells to yield transformed plant cells; and (b) regenerating a plant or plant component from the transformed plant cells, where the dominant negative gene product of the tobacco nicotine demethylase is expressed in the cells of the plant or plant component, thereby reducing the expression of tobacco nicotine demethylase in a plant or plant component. In particular embodiments of this aspect of the invention, the transgene encoding the dominant negative gene product is constitutively expressed or is inducibly expressed, for example, in a tissue-specific, cell-specific, or organ-specific manner.

A further aspect of the invention features an additional method for reducing the expression or the enzymatic activity of tobacco nicotine demethylase in plant cell. This method involves reducing the level of an endogenous tobacco nicotine demethylase, or its enzymatic activity, in the plant cell. Desirably, the plant cell is from a dicot, a solanaceous plant, or a species of *Nicotiana*. In desirable embodiments of this aspect, reducing the level of endogenous tobacco nicotine demethylase involves expressing a transgene encoding an antisense nucleic acid molecule or an RNA molecule capable of inducing RNA interference (RNAi) of a tobacco nicotine demethylase in the plant cell, or involves expressing a transgene encoding a double-stranded RNA molecule of a tobacco nicotine demethylase in the plant cell. Desirably, the double-stranded RNA is an RNA sequence corresponding to the sequence of SEQ ID NO:1, SEQ ID NO:3, SEQ ID NO:5, SEQ ID NO:6, or SEQ ID NO:7, or a fragment thereof. In an additional embodiment, reducing the level of endogenous tobacco nicotine demethylase involves co-suppression of the endogenous tobacco nicotine demethylase in the plant cell or involves expressing a dominant negative gene product in the plant cell. In particular, the dominant negative gene product may include a gene that encodes a mutated form the amino acid sequence of SEQ ID NO:2.

In other desirable embodiments of this aspect of the invention, the endogenous tobacco nicotine demethylase includes a point mutation in a gene that encodes the amino acid sequence of SEQ ID NO:2. In other desirable embodiments reducing the level of expression of an endogenous tobacco nicotine demethylase involves a deletion in a gene that encodes a tobacco nicotine demethylase or involves an insertion in a gene that encodes a tobacco nicotine demethylase. The reduced expression may occur at the transcriptional level, at the translational level, or at the post-translational level.

A further aspect of the invention features a method for identifying a compound which alters the expression of a tobacco nicotine demethylase in a cell. This method involves the steps of: (a) providing a cell containing a gene encoding a tobacco nicotine demethylase; (b) applying a candidate compound to the cell; and (c) measuring expression of the gene encoding the tobacco nicotine demethylase, where an increase or decrease in expression relative to an untreated control sample is an indication that the compound alters expression of the tobacco nicotine demethylase.

In a desirable embodiment of this method, the gene of part (a) encodes a tobacco nicotine demethylase having at least 70% identity to the amino acid sequence of SEQ ID NO:2. Desirably, the compound decreases or increases expression of the gene that encodes the tobacco nicotine demethylase.

In another aspect, the invention features another method for identifying a compound which alters the activity of a tobacco nicotine demethylase in a cell. This method involves the steps of: (a) providing a cell expressing a gene encoding a tobacco nicotine demethylase; (b) applying a candidate compound to the cell; and (c) measuring the activity of the tobacco nicotine demethylase, where an increase or decrease in activity relative to an untreated control sample is an indication that the compound alters activity of the tobacco nicotine demethylase. In a desirable embodiment of this aspect of the invention, the gene of step (a) encodes a tobacco nicotine demethylase having at least 70% identity to the amino acid sequence of SEQ ID NO:2. Desirably, the compound decreases or increases the activity of the tobacco nicotine demethylase.

A further aspect of the invention features a cured tobacco plant or plant component containing (i) a reduced levels of nicotine demethylase or (ii) a nicotine demethylase having an altered enzymatic activity and a reduced amount of a nitrosamine. Desirably, the plant component is a tobacco leaf or tobacco stem. In a desirable embodiment, the nitrosamine is nornicotine, and the content of nornicotine desirably is less than 5 mg/g, 4.5 mg/g, 4.0 mg/g, 3.5 mg/g, 3.0 mg/g, more desirably less than 2.5 mg/g, 2.0 mg/g, 1.5 mg/g, 1.0 mg/g, more desirably less than 750 µg/g, 500 µg/g, 250 µg/g, 100 µg/g, even more desirably less than 75 µg/g, 50 µg/g, 25 µg/g, 10 µg/g, 7.0 µg/g, 5.0 µg/g, 4.0 µg/g, and even more desirably less than 2.0 µg/g, 1.0 µg/g, 0.5 µg/g, 0.4 µg/g, 0.2 µg/g, 0.1 µg/g, 0.05 µg/g, or 0.01 µg/g or wherein the percentage of secondary alkaloids relative to total alkaloid content therein is less than 90%, 70%, 50%, 30%, 10%, desirably less than 5%, 4%, 3%, 2%, 1.5%, 1%, and more desirably less than 0.75%, 0.5%, 0.25%, or 0.1%. In another desirable embodiment, the nitrosamine is N'-nitrosonornicotine (NNN), and the content of N'-NNN desirably is less than 5 mg/g, 4.5 mg/g, 4.0 mg/g, 3.5 mg/g, 3.0 mg/g, more desirably less than 2.5 mg/g, 2.0 mg/g, 1.5 mg/g, 1.0 mg/g, more desirably less than 750 µg/g, 500 µg/g, 250 µg/g, 100 µg/g, even more desirably less than 75 µg/g, 50 µg/g, 25 µg/g, 10 µg/g, 7.0 µg/g, 5.0 µg/g, 4.0 µg/g, and even more desirably less than 2.0 µg/g, 1.0 µg/g, 0.5 µg/g, 0.4 µg/g, 0.2 µg/g, 0.1 µg/g, 0.05 µg/g, or 0.01 µg/g or wherein the percentage of secondary alkaloids relative to total alkaloid content contained therein is less than 90%, 70%, 50%, 30%, 10%, desirably less than 5%, 4%, 3%, 2%, 1.5%, 1%, and more desirably less than 0.75%, 0.5%, 0.25%, or 0.1%. In additional desirable embodiments of this aspect of the invention, the cured tobacco plant or plant component is a dark tobacco, Burley tobacco, flue-cured tobacco, air-cured tobacco, or oriental tobacco.

Further, the cured tobacco plant or plant component of the invention desirably includes a recombinant nicotine demethylase gene, e.g., one containing the sequence of SEQ ID NO:1 or SEQ ID NO:3, or a fragment thereof. Desirably, the expression of an endogenous nicotine demethylase gene in the cured tobacco plant or plant component is silenced.

Another aspect of the invention features a tobacco product containing a cured tobacco plant or plant component that includes (i) reduced expression of a nicotine demethylase or (ii) a nicotine demethylase having altered activity, and a reduced amount of a nitrosamine. Desirably, the tobacco product is smokeless tobacco, moist or dry snuff, a chewing tobacco, cigarette, cigar, cigarillo, pipe tobacco, or bidis. In particular, the tobacco product of this aspect of the invention may contain dark tobacco, milled tobacco, or include a flavoring component.

The invention also features a method of making a tobacco product, e.g., a smokeless tobacco product, containing (i) reduced expression of a nicotine demethylase or (ii) a nicotine demethylase having altered (e.g., reduced) enzymatic activity, and a reduced amount of a nitrosamine. This method involves providing a cured tobacco plant or plant component containing (i) a reduced level of nicotine demethylase or (ii) a nicotine demethylase having an altered enzymatic activity and a reduced amount of a nitrosamine and preparing the tobacco product from the cured tobacco plant or plant component.

DEFINITIONS

"Enzymatic activity" is meant to include but is not limited to demethylation, hydroxylation, epoxidation, N-oxidation, sulfooxidation, N-, S-, and 0-dealkylations, desulfation, deamination, and reduction of azo, nitro, N-oxide, and other such enzymatically reactive chemical groups. Altered enzymatic activity refers to a decrease in enzymatic activity (for example, of a tobacco nicotine demethylase) by at least 10-20%, preferably by at least 25-50%, and more preferably by at least 55-95% or greater relative to the activity of a control enzyme (for example, a wild-type tobacco plant nicotine demethylase). The activity of a tobacco nicotine demethylase may be assayed using methods standard in the art, such as by measuring the demethylation of radioactive nicotine by yeast-expressed microsomes, as described herein.

The term "nucleic acid" refers to a deoxyribonucleotide or ribonucleotide polymer in either single- or double-stranded form, or sense or anti-sense, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof. The terms "operably linked," "in operable combination," and "in operable order" refer to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, expresses the nucleic acid or expresses a peptide, heterologous peptide, or protein encoded by a heterologous nucleic acid. Recombinant cells can express genes or gene fragments in either the sense or antisense form or an RNA molecule capable of inducing RNA interference (RNAi) that are not found within the native (non-recombinant) form of the cell. Recombinant cells can also express genes that are found in the native form of the cell, but wherein the genes are modified and re-introduced into the cell by artificial means.

A "structural gene" is that portion of a gene comprising a DNA segment encoding a protein, polypeptide or a portion thereof, and excluding, for example, the 5' sequence which drives the initiation of transcription or the 3'UTR. The structural gene may alternatively encode a nontranslatable product. The structural gene may be one which is normally found in the cell or one which is not normally found in the cell or cellular location wherein it is introduced, in which case it is termed a "heterologous gene." A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications that could affect biological activity or its characteristics, the biological activity or the chemical structure of the expression product, the rate of expression or the manner of expression control. Such modifications include, but are not limited to, mutations, insertions, deletions and substitutions of one or more nucleotides.

The structural gene may constitute an uninterrupted coding sequence or it may include one or more introns, bounded by the appropriate splice junctions. The structural gene may be translatable or non-translatable, including an antisense or an RNA molecule capable of inducing RNA interference (RNAi). The structural gene may be a composite of segments derived from a plurality of sources and from a plurality of gene sequences (naturally occurring or synthetic, where synthetic refers to DNA that is chemically synthesized).

An "exon" as used herein in reference to a nucleic acid sequence is meant a portion of the nucleic acid sequence of a gene, where the nucleic acid sequence of the exon encodes at least one amino acid of the gene product. An exon is typically adjacent to a noncoding DNA segment such as an intron. Desirably, an exon encodes a portion of the tobacco nicotine demethylase amino acid sequence of SEQ ID NO:2, such as amino acids 1-313 and/or 314-517 of the sequence of SEQ ID NO:2.

An "intron" as used herein in reference to a nucleic acid sequence is meant a non-coding region of a gene that is flanked by coding regions. An intron is typically a noncoding region of a gene that is transcribed into an RNA molecule but is then excised by RNA splicing during production of the messenger RNA or other functional structural RNA. Desirably, an intron includes the sequence of SEQ ID NO:5, or a fragment thereof.

A "3'UTR" as used herein in reference to a nucleic acid sequence is meant a non-coding nucleic acid sequence proximal to a stop codon of an exon. Desirably, a 3'UTR includes the sequence of SEQ ID NO:7, or a fragment thereof.

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

"Chemically synthesized," as related to a sequence of DNA, means that portions of the component nucleotides were assembled in vitro. Manual chemical synthesis of DNA may be accomplished using well-established procedures (Caruthers, *Methodology of DNA and RNA Sequencing*, (1983), Weissman (ed.), Praeger Publishers, New York, Chapter 1); automated chemical synthesis can be performed using one of a number of commercially available machines.

Optimal alignment of sequences for comparison may be conducted, for example, by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The NCBI Basic Local Alignment Search Tool (BLAST) (Altschul et al., 1990) is available from several sources, including the National Center for Biological Information (NCBI, Bethesda, Md.) and on the internet, for use in connection with the sequence analysis programs blastp, blastn, blastx, tblastn, and tblastx. It can be accessed at http://www.ncbi.nlm.nih.gov/BLAST/. A description of how to determine sequence identity using this program is available at http://www.ncbi.nlm.nih.gov/BLAST/blast help.html.

The terms "substantial amino acid identity" or "substantial amino acid sequence identity" as applied to amino acid sequences and as used herein denote a characteristic of a polypeptide, wherein the peptide comprises a sequence that has at least 70 percent sequence identity, preferably 80 percent amino acid sequence identity, more preferably 90 percent amino acid sequence identity, and most preferably at least 99 to 100 percent sequence identity as compared to the protein sequence of SEQ ID NOS:2 and/or 4. Desirably, for a nicotine demethylase, sequence comparison is desirably compared for a region following the cytochrome p450 motif (GXRXCX(G/A); SEQ ID NO:29) to the stop codon of the translated peptide.

The terms "substantial nucleic acid identity" or "substantial nucleic acid sequence identity" as applied to nucleic acid sequences and as used herein denote a characteristic of a polynucleotide sequence, wherein the polynucleotide comprises a sequence that has at least 50 percent, preferably 60, 65, 70, or 75 percent sequence identity, more preferably 81 or 91 percent nucleic acid sequence identity, and most preferably at least 95, 99, or even 100 percent sequence identity as compared to SEQ ID NOS:1, 3, 5, 6, and/or 7. Desirably, for a nicotine demethylase nucleic acid sequence, comparison is desirably compared for a sequence encoding a region following the cytochrome p450 motif (GXRXCX(G/A); SEQ ID NO:29) to the stop codon of the translated peptide.

Another indication that nucleotide sequences are substantially identical is if two molecules hybridize to each other under stringent conditions. Stringent conditions are sequence-dependent and will be different in different circumstances. Generally, stringent conditions are selected to be about 5° C. to about 20° C., usually about 10° C. to about 15° C., lower than the thermal melting point (Tm) for the specific sequence at a defined ionic strength and pH. The Tm is the temperature (under defined ionic strength and pH) at which 50% of the target sequence hybridizes to a matched probe. Typically, stringent conditions will be those in which the salt concentration is about 0.02 molar at pH 7 and the temperature is at least about 60° C. For instance in a standard Southern hybridization procedure, stringent conditions will include an initial wash in 6×SSC at 42° C. followed by one or more additional washes in 0.2×SSC at a temperature of at least about 55° C., typically about 60° C., and often about 65° C.

Nucleotide sequences are also substantially identical for purposes of this invention when said nucleotide sequences encode polypeptides and/or proteins which are substantially identical. Thus, where one nucleic acid sequence encodes essentially the same polypeptide as a second nucleic acid sequence, the two nucleic acid sequences are substantially identical even if they would not hybridize under stringent conditions due to degeneracy permitted by the genetic code (see, Darnell et al. (1990) Molecular Cell Biology, Second Edition Scientific American Books W. H. Freeman and Company New York for an explanation of codon degeneracy and the genetic code). Protein purity or homogeneity can be indicated by a number of means well known in the art, such as polyacrylamide gel electrophoresis of a protein sample, followed by visualization upon staining. For certain purposes high resolution may be needed and HPLC or a similar means for purification may be used.

By an antibody that "specifically binds" or "specifically recognizes" a tobacco nicotine demethylase is meant an increased affinity of the antibody for a tobacco nicotine demethylase relative to an equal amount of any other protein. For example, an antibody that specifically binds to a tobacco nicotine demethylase containing the amino acid sequence of SEQ ID NO:2 desirably has an affinity for its antigen that is least 2-fold, 5-fold, 10-fold, 30-fold, or 100-fold greater than for an equal amount of any other antigen, including related antigens. Binding of an antibody to an antigen, e.g., tobacco nicotine demethylase, may be determined by any number of standard methods in the art, e.g., Western analysis, ELISA, or co-immunoprecipitation.

As used herein, the term "vector" is used in reference to nucleic acid molecules that transfer DNA segment(s) into a cell. A vector may act to replicate DNA and may reproduce independently in a host cell. The term "vehicle" is sometimes used interchangeably with "vector." The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Desirably, the promoter includes the sequence of SEQ ID NO:6, or a fragment thereof that drives transcription. Also desirable are promoter sequences that have at least 50%, 60%, 75%, 80%, 90%, 95%, or even 99% sequence identity to the sequence of SEQ ID NO:6 and that drive transcription. Eucaryotic cells are known to utilize promoters, enhancers, and termination and polyadenylation signals, such as the 3'UTR sequence of SEQ ID NO:7. In some instances, it has been observed that plant expression vectors require the presence of plant derived introns, such as the intron having the sequence of SEQ ID NO:5, to have stable expression. As such, the sequence of SEQ ID NO:5, or any other intron having an appropriate RNA splice junction may be used as further described herein.

For the purpose of regenerating complete genetically engineered plants with roots, a nucleic acid may be inserted into plant cells, for example, by any technique such as in vivo inoculation or by any of the known in vitro tissue culture techniques to produce transformed plant cells that can be regenerated into complete plants. Thus, for example, the insertion into plant cells may be by in vitro inoculation by pathogenic or non-pathogenic *A. tumefaciens*. Other such tissue culture techniques may also be employed.

"Plant tissue," "plant component" or "plant cell" includes differentiated and undifferentiated tissues of plants, including, but not limited to, roots, shoots, leaves, pollen, seeds, tumor tissue and various forms of cells in culture, such as single cells, protoplasts, embryos and callus tissue. The plant tissue may be in planta or in organ, tissue or cell culture.

"Plant cell" as used herein includes plant cells in planta and plant cells and protoplasts in culture. "cDNA" or "complementary DNA" generally refers to a single stranded DNA molecule with a nucleotide sequence that is complementary to an unprocessed RNA molecule containing an intron, or a processed mRNA lacking introns. cDNA is formed by the action of the enzyme reverse transcriptase on an RNA template.

"Tobacco" as used herein includes flue-cured, Virginia, Burley, dark, oriental, and other types of plant within the genus *Nicotiana*. Seed of the genus *Nicotiana* is readily available commercially in the form of *Nicotiana tabacum*.

"Articles of manufacture" or "tobacco products" include products such as moist and dry snuff, chewing tobaccos, cigarettes, cigars, cigarillos, pipe tobaccos, bidis, and similar tobacco-derived products.

By "gene silencing" is meant a decrease in the level of gene expression (for example, expression of a gene encoding a tobacco nicotine demethylase) by at least 30-50%, preferably by at least 50-80%, and more preferably by at least 80-95% or greater relative to the level in a control plant (for example, a wild-type tobacco plant). Reduction of such expression levels may be accomplished by employing standard methods which are known in the art including, without limitation, RNA interference, triple strand interference, ribozymes, homologous recombination, virus-induced gene silencing, antisense and co-suppression technologies, expression of a dominant negative gene product, or through the generation of mutated genes using standard mutagenesis techniques, such as those described herein. Levels of a tobacco nicotine demethylase polypeptide or transcript, or both, are monitored according to any standard technique including, but not limited to, Northern blotting, RNase protection, or immunoblotting.

By a "tobacco nicotine demethylase" or "nicotine demethylase" as used herein, is meant a polypeptide that is substantially identical to the sequence of SEQ ID NO:2. Desirably, a tobacco nicotine demethylase is capable of converting nicotine ($C_{10}H_{12}N_2$, also referred to as 341-Methyl-2-pyrrolidinyl)pyridine) to nornicotine ($C_9H_{12}N_2$). The activity of a tobacco nicotine demethylase may be assayed using methods standard in the art, such as by measuring the demethylation of radioactive nicotine by yeast-expressed microsomes, as described herein.

By a "fragment" or "portion" of a tobacco nicotine demethylase amino acid sequence is meant at least e.g., 20, 15, 30, 50, 75, 100, 250, 300, 400, or 500 contiguous amino acids of the amino acid sequence of SEQ ID NO:2. Exemplary desirable fragments are amino acids 1-313 of the sequence of SEQ ID NO:2 and amino acids 314-517 of the sequence of SEQ ID NO:2. In addition, with respect to a fragment or portion of a tobacco nicotine demethylase nucleic acid sequence, desirable fragments include at least 100, 250, 500, 750, 1000, or 1500 contiguous nucleic acids of the nucleic acid sequence of SEQ ID NO:1. Exemplary desirable fragments are nucleic acids 1-2009, 2010-2949, 2950-3946, 3947-4562, 4563-6347, and 4731-6347 of the sequence of SEQ ID NO:1. Other desirable fragments include nucleic acids 1-100, 101-250, 251-500, 501-750, and 751-998 of SEQ ID NO:5, nucleic acids 1-398, 1-1400, 1401-2009, 1840-2009, 1940-2009, 399-1240, and 1241-2009 of SEQ ID NO:6, and nucleic acids 1-100, 101-250, 251-500, 501-750, 751-1000, 1001-1250, 1251-1500, and 1501-1786 of SEQ ID NO:7.

By a "substantially pure polypeptide" is meant a tobacco nicotine demethylase that has been separated from most components which naturally accompany it; however, other proteins found in the microsomal fraction associated with a preparation having a nicotine demethylase activity of at least 8.3 pKat/mg protein, 9 pKat/mg protein, 9.5 pKat/mg protein, 10 pKat/mg protein, 10.5 pKat/mg, or 10.8 pKat/mg protein are also considered to be a substantially pure polypeptide. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a tobacco nicotine demethylase. A substantially pure tobacco nicotine demethylase may be obtained, for example, by extraction from a natural source (for example, a tobacco plant cell); by expression of a recombinant nucleic acid encoding a tobacco nicotine demethylase; or by chemically synthesizing the protein. Purity can be measured by any appropriate method, for example, column chromatography, polyacrylamide gel electrophoresis, or by HPLC analysis.

By "isolated nucleic acid molecule" is meant a nucleic acid sequence free from the nucleic acid sequences that naturally flank the sequence of the nucleic acid molecule in the genome of an organism.

By "transformed cell" is meant a cell into which (or into an ancestor of which) has been introduced, by means of recombinant DNA techniques, a DNA molecule, for example, a DNA molecule encoding a tobacco nicotine demethylase.

As provided herein, the terms "cytochrome p450" and "p450" are used interchangeably.

BRIEF DESCRIPTION OF THE DRAWINGS

FIGS. 2-1 to 2-3 is the genomic tobacco nicotine demethylase nucleic acid sequence (SEQ ID NO:1) and its translation product (SEQ ID NO:2).

FIG. 3 is the nucleic acid sequence of the tobacco nicotine demethylase coding region (SEQ ID NO:3) (also referred to as D121-AA8) and its translation product (SEQ ID NO:4).

FIG. 4 is the nucleic acid sequence of an intron (SEQ ID NO:5) present in the tobacco nicotine demethylase genomic sequence.

FIG. 5 is the nucleic acid sequence of the tobacco nicotine demethylase promoter region (SEQ ID NO:6).

FIG. 6 is the nucleic acid sequence of the 3'UTR of the tobacco nicotine demethylase gene (SEQ ID NO:7).

DETAILED DESCRIPTION

Figure 1:
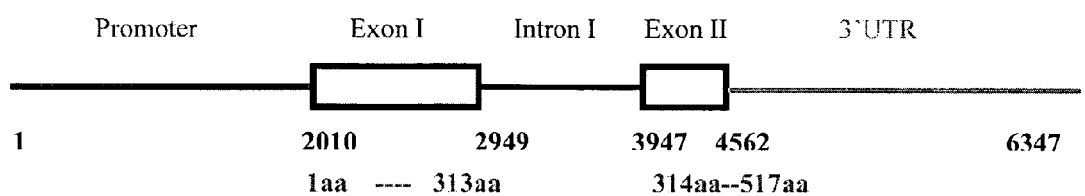
FIG. 1 is a schematic diagram of the genomic structure of the tobacco nicotine demethylase gene.

Identifying a Genomic Clone Encoding a Tobacco Nicotine Demethylase

In accordance with the present invention, RNA was extracted from *Nicotiana* tissue of converter and non-converter *Nicotiana* lines. The extracted RNA was then used to create cDNA. Nucleic acid sequences of the present invention were then generated using two strategies.

In the first strategy, the poly A enriched RNA was extracted from plant tissue and cDNA was made by reverse transcription PCR. The single strand cDNA was then used to create p450 specific PCR populations using degenerate primers plus a oligo d(T) reverse primer. The primer design was based on the highly conserved motifs of other plant cytochrome p450 gene sequences. Examples of specific degenerate primers are set forth in FIG. 1 of the US 2004/0103449 A1 and US 2004/0111759 A1 patent application publications, which are hereby incorporated by reference. The sequence of fragments from plasmids containing appropriate size inserts was further analyzed. These size inserts typically ranged from about 300 to about 800 nucleotides depending on which primers were used.

In a second strategy, a cDNA library was initially constructed. The cDNA in the plasmids was used to create p450 specific PCR populations using degenerate primers plus T7 primer on plasmid as reverse primer. As in the first strategy, the sequence of fragments from plasmids containing appropriate size inserts was further analyzed.

*Nicotiana* plant lines known to produce high levels of nornicotine (converter) and plant lines having low levels of nornicotine may be used as starting materials. Leaves can then be removed from plants and treated with ethylene to activate p450 enzymatic activities defined herein. Total RNA is extracted using techniques known in the art. cDNA fragments can then be generated using PCR(RT-PCR) with the oligo d(T) primer. The cDNA library can then be constructed as more fully described in examples herein.

The conserved region of p450 type enzymes was used as a template for degenerate primers. Using degenerate primers, p450 specific bands were amplified by PCR. Bands indicative for p450-like enzymes were identified by DNA sequencing. PCR fragments were characterized using BLAST search, alignment or other tools to identify appropriate candidates.

Sequence information from identified fragments was used to develop PCR primers. These primers in combination with plasmid primers in cDNA library were used to clone full-length p450 genes. Large-scale Southern reverse analysis was conducted to examine the differential expression for all fragment clones obtained and in some cases full-length clones. In this aspect of the invention, these large-scale reverse Southern assays can be conducted using labeled total cDNAs from different tissues as a probe to hybridize with cloned DNA fragments in order to screen all cloned inserts. Nonradioactive and radioactive (P32) Northern blotting assays were also used to characterize cloned p450 fragments and full-length clones.

Peptide specific antibodies were made by deriving their amino acid sequence and selecting peptide regions that were antigenic and unique relative to other clones. Rabbit antibodies were made to synthetic peptides conjugated to a carrier protein. Western blotting analyses or other immunological methods were performed on plant tissue using these antibodies. In addition, peptide specific antibodies were made for several full-length clones by deriving their amino acid sequence and selecting peptide regions that were potentially antigenic and were unique relative to other clones. Rabbit antibodies were made to synthetic peptides conjugated to a carrier protein. Western blotting analyses were performed using these antibodies.

Downregulating Tobacco Nicotine Demethylase

Plants having decreased expression of a tobacco nicotine demethylase are generated according to standard gene silencing methods. (For reviews, see Arndt and Rank, Genome 40:785-797, 1997; Turner and Schuch, *Journal of Chemical Technology and Biotechnology* 75:869-882, 2000; and Klink and Wolniak, *Journal of Plant Growth Regulation* 19(4):371-384, 2000.) In particular, the tobacco nicotine demethylase gene promoter (e.g., SEQ ID NO:6), structural gene (SEQ ID NO:3), intron (SEQ ID NO:5), or 3' UTR (SEQ ID NO:7) or the entire genomic clone (SEQ ID NO:1) can be used to alter tobacco phenotypes or tobacco metabolites, for example, nornicotine in any *Nicotiana* species. Decreased expression of a tobacco nicotine demethylase gene may be achieved using, for example, RNA interference (RNAi) (Smith et al., *Nature* 407:319-320, 2000; Fire et al., *Nature* 391:306-311, 1998; Waterhouse et al., *PNAS* 95:13959-13964, 1998; Stalberg et al., *Plant Molecular Biology* 23:671-683, 1993; Brignetti et al., EMBO J. 17:6739-6746, 1998; Allen et al., *Nature Biotechnology* 22: 1559-1566, 2004); virus-induced gene silencing ("VIGS") (Baulcombe, *Current Opinions in Plant Biology*, 2:109-113, 1999; Cogoni and Macino, Genes Dev 10: 638-643, 2000; Ngelbrecht et al., PNAS 91:10502-10506, 1994); silencing the target gene by transferring a plant endogenous gene in the sense orientation (Jorgensen et al., *Plant Mol Biol* 31: 957-973, 1996); expression of antisense gene; homologous recombination (Ohl et al., Homologous Recombination and Gene Silencing in Plants (Kluwer, Dordrecht, The Netherlands, 1994); Cre/lox systems (Qin et al., PNAS 91: 1706-1710, 1994; Koshinsky et al., *The Plant Journal* 23: 715-722, 2000; Chou, et al., *Plant and Animal Genome VII Conference Abstracts*. San Diego, Calif., 17-21 Jan. 1999); gene trapping and T-DNA tagging (Burns et al., Genes Dev. 8: 1087-1105, 1994; Spradling, et al., PNAS 92:10824-10830, 1995; Skarnes et al., *Bio/Technology* 8, 827-831, 1990; Sundaresan, et al., *Genes Dev.* 9: 1797-1810, 1995); and any of the other possible gene silencing systems that are available in the science areas that result in the downregulation of expression of a tobacco nicotine demethylase or in a reduction in its enzymatic activity. Exemplary methods are described in more detail below.

RNA Interference

RNA interference ("RNAi") is a generally applicable process for inducing potent and specific post-translational gene silencing in many organisms including plants (see, e.g., Bosher et al., *Nat. Cell Biol.* 2:E31-36, 2000; and Tavernarakis et al., *Nat. Genetics* 24:180-183, 2000). RNAi involves introduction of RNA with partial or fully double-stranded character into the cell or into the extracellular environment. Inhibition is specific in that a nucleotide sequence from a portion of the target gene (e.g., a tobacco nicotine demethylase) is chosen to produce inhibitory. RNA. The chosen portion generally encompasses exons of the target gene, but the chosen portion may also include untranslated regions (UTRs), as well as introns (e.g., the sequences of SEQ ID NO:5 or 7).

For example, to construct transformation vectors that produce RNAs capable of duplex formation, two tobacco nicotine demethylase nucleic acid sequences, one in the sense and the other in the antisense orientation, may be operably linked, and placed under the control of a strong viral promoter, such as CaMV 35S or the promoter isolated from cassava brown streak virus (CBSV). However, use of the endogenous promoter, such as the tobacco nicotine demethylase promoter having the sequence of SEQ ID NO:6, or a fragment thereof that drives transcription, may also be desirable. The length of the tobacco nicotine demethylase nucleic acid sequences included in such a construct is desirably at least 25 nucleotides, but may encompass a sequence that includes up to the full-length tobacco nicotine demethylase gene.

Constructs that produce RNAs capable of duplex formation may be introduced into the genome of a plant, such as a tobacco plant, by *Agrobacterium*-mediated transformation (Chuang et al., *Proc. Natl. Acad. Sci.* USA 97:4985-4990, 2000), causing specific and heritable genetic interference in a tobacco nicotine demethylase. The double-stranded RNA may also be directly introduced into the cell (i.e., intracellularly) or introduced extracellularly, for example, by bathing a seed, seedling, or plant in a solution containing the double-stranded RNA.

Depending on the dose of double-stranded RNA material delivered, the RNAi may provide partial or complete loss of function for the target gene. A reduction or loss of gene expression in at least 99% of targeted cells may be obtained. In general, lower doses of injected material and longer times after administration of dsRNA result in inhibition in a smaller fraction of cells.

The RNA used in RNAi may comprise one or more strands of polymerized ribonucleotide; it may include modifications to either the phosphate-sugar backbone or the nucleoside. The double-stranded structure may be formed by a single self-complementary RNA strand or by two complementary RNA strands and RNA duplex formation may be initiated either inside or outside the cell. The RNA may be introduced in an amount which allows delivery of at least one copy per cell. However, higher doses (e.g., at least 5, 10, 100, 500 or 1000 copies per cell) of double-stranded material may yield more effective inhibition. Inhibition is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence may also be effective for inhibition. Thus, sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

In addition, the RNA used for RNAi may be synthesized either in vivo or in vitro. For example, endogenous RNA polymerase in the cell may mediate transcription in vivo, or cloned RNA polymerase can be used for transcription in vivo or in vitro. For transcription from a transgene in vivo or an expression construct, a regulatory region may be used to transcribe the RNA strand (or strands).

Triple Strand Interference

Endogenous tobacco nicotine demethylase gene expression may also be downregulated by targeting deoxyribonucleotide sequences complementary to the regulatory region of a tobacco nicotine demethylase gene (e.g., promoter or enhancer regions) to form triple helical structures that prevent transcription of the tobacco nicotine demethylase gene in target cells. (See generally, Helene, *Anticancer Drug Des.*

6:569-584, 1991; Helene et al., *Ann. N.Y. Acad. Sci.* 660:27-36, 1992; and Maher, *Bioassays* 14:807-815, 1992.)

Nucleic acid molecules used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Ribozymes

Ribozymes are RNA molecules that act as enzymes and can be engineered to cleave other RNA molecules. A ribozyme may be designed to specifically pair with virtually any target RNA and cleave the phosphodiester backbone at a specific location, thereby functionally inactivating the target RNA. The ribozyme itself is not consumed in this process and can act catalytically to cleave multiple copies of mRNA target molecules. Accordingly, ribozymes may also be used as a means to downregulate expression of a tobacco nicotine demethylase. The design and use of target RNA-specific ribozymes is described in Haseloff et al. (*Nature* 334:585-591, 1988). Preferably, the ribozyme includes at least about 20 continuous nucleotides complementary to the target sequence (e.g., a tobacco nicotine demethylase) on each side of the active site of the ribozyme.

In addition, ribozyme sequences may also be included within an antisense RNA to confer RNA-cleaving activity upon the antisense RNA and, thereby, increasing the effectiveness of the antisense construct.

Homologous Recombination

Gene replacement technology is another desirable method for downregulating expression of a given gene, e.g., a tobacco nicotine demethylase. Gene replacement technology is based upon homologous recombination (see, Schnable et al., *Curr. Opinions Plant Biol.* 1:123-129, 1998). The nucleic acid sequence of the enzyme of interest such as a tobacco nicotine demethylase can be manipulated by mutagenesis (e.g., insertions, deletions, duplications or replacements) to decrease enzymatic function. The altered sequence can then be introduced into the genome to replace the existing, e.g., wild-type, gene via homologous recombination (Puchta et al., *Proc. Natl. Acad. Sci. USA* 93:5055-5060, 1996; and Kempin et al., *Nature* 389:802-803, 1997).

Co-Suppression

A further desirable method of silencing gene expression is co-suppression (also referred to as sense suppression). This technique, which involves introduction of a nucleic acid configured in the sense orientation, has been shown to effectively block the transcription of target genes (see, for example, Napoli et al., *Plant Cell*, 2:279-289, 1990 and Jorgensen et al., U.S. Pat. No. 5,034,323).

Generally, sense suppression involves transcription of the introduced sequence. However, co-suppression may also occur where the introduced sequence contains no coding sequence per se, but only intron (e.g., the sequence of SEQ ID NO:5) or untranslated sequences such as the sequence of SEQ ID NO:7 or other such sequences substantially identical to sequences present in the primary transcript of the endogenous gene to be repressed. The introduced sequence generally will be substantially identical to the endogenous gene targeted for repression. Such identity is typically greater than about 50%, but higher identities (for example, 80% or even 95%) are preferred because they result in more effective repression. The effect of co-suppression may also be applied to other proteins within a similar family of genes exhibiting homology or substantial homology. Segments from a gene from one plant can be used directly, for example, to inhibit expression of homologous genes in different plant species.

In sense suppression, the introduced sequence, requiring less than absolute identity, need not be full length, relative to either the primary transcription product or to fully processed mRNA. A higher degree of sequence identity in a shorter than full-length sequence compensates for a longer sequence of lesser identity. Furthermore, the introduced sequence need not have the same intron or exon pattern, and identity of non-coding segments may be equally effective. Sequences of at least 50 base pairs are preferred, with introduced sequences of greater length being more preferred (see, for example, those methods described by Jorgensen et al., U.S. Pat. No. 5,034,323).

Antisense Suppression

In antisense technology, a nucleic acid segment from the desired plant gene, such as that found in SEQ ID NOS:1, 3, 5, 6, or 7, is cloned and operably linked to an expression control region such that the antisense strand of RNA is synthesized. The construct is then transformed into plants and the antisense strand of RNA is produced. In plant cells, it has been shown that antisense RNA inhibits gene expression.

The nucleic acid segment to be introduced in antisense suppression is generally substantially identical to at least a portion of the endogenous gene or genes to be repressed, but need not be identical. The nucleic acid sequences of the tobacco nicotine demethylase disclosed herein may be included in vectors designed such that the inhibitory effect applies to other proteins within a family of genes exhibiting homology or substantial homology to the target gene. Segments from a gene from one plant can be used, for example, directly to inhibit expression of homologous genes in different tobacco varieties.

The introduced sequence also need not be full length relative to either the primary transcription product or to fully processed mRNA. Generally, higher homology can be used to compensate for the use of a shorter sequence. Moreover, the introduced sequence need not have the same intron or exon pattern, and homology of non-coding segments will be equally effective. In general, such an antisense sequence will usually be at least 15 base pairs, preferably about 15-200 base pairs, and more preferably 200-2,000 base pairs in length or greater. The antisense sequence may be complementary to all or a portion of the gene to be suppressed (for example, a tobacco nicotine demethylase promoter (SEQ ID NO:6), exon, intron (SEQ ID NO:5), or UTR (SEQ ID NO:7), and, as appreciated by those skilled in the art, the particular site or sites to which the antisense sequence binds as well as the length of the antisense sequence will vary, depending upon the degree of inhibition desired and the uniqueness of the antisense sequence. A transcriptional construct expressing a plant negative regulator antisense nucleotide sequence includes, in the direction of transcription, a promoter, the sequence coding for the antisense RNA on the sense strand, and a transcriptional termination region. Antisense sequences may be constructed and expressed as described, for example, in van der Krol et al. (*Gene* 72: 45-50, 1988); Rodermel et al. (*Cell* 55: 673-681, 1988); Mol et al. (*FEBS Lett.* 268: 427-430, 1990); Weigel and Nilsson (*Nature* 377: 495-500, 1995); Cheung et al., (*Cell* 82: 383-393, 1995); and Shewmaker et al. (U.S. Pat. No. 5,107,065).

Dominant Negatives

Transgenic plants expressing a transgene encoding a dominant negative gene product of a tobacco nicotine demethylase may be assayed in artificial environments or in the field to demonstrate that the transgene confers downregulates a tobacco nicotine demethylase in the transgenic plant. Dominant negative transgenes are constructed according to methods known in the art. Typically, a dominant negative gene encodes a mutant negative regulator polypeptide of a tobacco nicotine demethylase which, when overexpressed, disrupts the activity of the wild-type enzyme.

Mutants

Plants having decreased expression or enzymatic activity of a tobacco nicotine demethylase may also be generated using standard mutagenesis methodologies. Such mutagenesis methods include, without limitation, treatment of seeds with ethyl methylsulfate (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, New York (3.sup.rd ed), 1987), use of transposons (Fedoroff et al., 1984; U.S. Pat. No. 4,732,856 and U.S. Pat. No. 5,013,658), as well as T-DNA insertion methodologies (Hoekema et al., 1983; U.S. Pat. No. 5,149,645). The types of mutations that may be present in a tobacco nicotine demethylase gene include, for example, point mutations, deletions, insertions, duplications, and inversions. Such mutations desirably are present in the coding region of a tobacco nicotine demethylase gene; however mutations in the promoter region, and intron, or an untranslated region of a tobacco nicotine demethylase gene may also be desirable.

For instance, T-DNA insertional mutagenesis may be used to generate insertional mutations in a tobacco nicotine demethylase gene to downregulate the expression of the gene. Theoretically, about 100,000 independent T-DNA insertions are required for a 95% probability of getting an insertion in any given gene (McKinnet, *Plant J.* 8: 613-622, 1995; and Forsthoefel et al., *Aust. J. Plant Physiol.* 19:353-366, 1992). T-DNA tagged lines of plants may be screened using polymerase chain reaction (PCR) analysis. For example, a primer can be designed for one end of the T-DNA and another primer can be designed for the gene of interest and both primers can be used in the PCR analysis. If no PCR product is obtained, then there is no insertion in the gene of interest. In contrast, if a PCR product is obtained, then there is an insertion in the gene of interest.

Expression of a mutated tobacco nicotine demethylase may be evaluated according to standard procedures (for example, those described herein) and, optionally, may be compared to expression of the non-mutated enzyme. When compared to non-mutated plants, mutated plants having decreased expression of a gene encoding a tobacco nicotine demethylase are desirable embodiments of the present invention.

Plant Promoters

An example of a useful plant promoter according to the invention is the nicotine demethylase promoter having the sequence of SEQ ID NO:6, or a fragment thereof that drives transcription. Another desirable promoter is a caulimovirus promoter, for instance, a cauliflower mosaic virus (CaMV) promoter or the cassava vein mosaic virus (CsVMV) promoter. These promoters confer high levels of expression in most plant tissues, and the activity of these promoters is not dependent on virally encoded proteins. CaMV is a source for both the 35S and 19S promoters. Examples of plant expression constructs using these promoters are known in the art. In most tissues of transgenic plants, the CaMV 35S promoter is a strong promoter. The CaMV promoter is also highly active in monocots. Moreover, activity of this promoter can be further increased (i.e., between 2-10 fold) by duplication of the CaMV 35S promoter.

Other useful plant promoters include, without limitation, the nopaline synthase (NOS) promoter, the octopine synthase promoter, figwort mosiac virus (FMV) promoter, the rice actin promoter, and the ubiquitin promoter system.

Exemplary monocot promoters include, without limitation, commelina yellow mottle virus promoter, sugar cane badna virus promoter, rice tungro bacilliform virus promoter, maize streak virus element, and wheat dwarf virus promoter.

For certain applications, it may be desirable to produce a tobacco nicotine demethylase, such as a dominant negative mutant tobacco nicotine demethylase, in an appropriate tissue, at an appropriate level, or at an appropriate developmental time. For this purpose, there are assortments of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression, light-regulated gene expression (for example, the pea rbcS-3A; the maize rbcS promoter; the chlorophyll a/b-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunI), organ-specific gene expression (for example, of the tuber-specific storage protein gene; the 23-kDa zein gene from maize described by; or the French bean β-phaseolin gene), or pathogen-inducible promoters (for example, the PR-1, prp-1, or (β-1,3 glucanase promoters, the fungal-inducible wirla promoter of wheat, and the nematode inducible promoters, TobRB7-5A and Hmg-1, of tobacco and parsley, respectively).

Plant Expression Vectors

Typically, plant expression vectors include (1) a cloned plant gene (e.g., a tobacco nicotine demethylase gene) under the transcriptional control of 5' and 3' regulatory sequences (e.g., the tobacco nicotine demethyase promoter (SEQ ID NO:6) and 3'UTR regions (SEQ ID NO:7)) and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Plant expression vectors may also optionally include RNA processing signals, e.g, introns, which have been shown to be important for efficient RNA synthesis and accumulation. The location of the RNA splice sequences can dramatically influence the level of transgene expression in plants. In view of this fact, an intron may be positioned upstream or downstream of a tobacco nicotine demethylase coding sequence in the transgene to alter levels of gene expression.

In addition to the aforementioned 5' regulatory control sequences, the expression vectors may also include regulatory control regions which are generally present in the 3' regions of plant genes. For example, the 3' terminator region (e.g., the sequence of SEQ ID NO:7) may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include the aminoglycoside phosphotransferase gene of transposon Tn5 (Aph II), genes encoding antibiotic resistance genes, for example, those encoding resistance to hygromycin, kanamycin, bleomycin, neomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad-spectrum herbicide Basta® (Bayer Cropscience Deutschland GmbH, Langenfeld, Germany). Other selectable markers include genes that provide resistance to other such herbicides such as glyphosate and the like, and imidazolinones, sulfonylureas, triazolopyrimidine herbicides, such as chlorosulfuron, bromoxynil, dalapon, and the like. Furthermore, genes encoding dihydrofolate reductase may be used in combination with molecules such as methotrexate.

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, for example, 20-100 µg/ml (kanamycin), 20-50 µg/ml (hygromycin), or 5-10 µg/ml (bleomycin). A useful strategy for selection of transformants for herbicide resistance is described, for example, by Vasil (*Cell Culture and Somatic Cell Genetics of Plants*, Vol I, II, III Laboratory Procedures and Their Applications Academic Press, New York, 1984).

In addition to a selectable marker, it may be desirable to use a reporter gene. In some instances a reporter gene may be used without a selectable marker. Reporter genes are genes which are typically not present or expressed in the recipient organism or tissue. The reporter gene typically encodes for a protein which provide for some phenotypic change or enzymatic property. Examples of such genes are provided in Weising et al. (*Ann. Rev. Genetics* 22:421, 1988), which is incorporated herein by reference. Preferred reporter genes include without limitation glucuronidase (GUS) gene and GFP genes.

Upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*) (see, for example, Lichtenstein and Fuller In: Genetic Engineering, vol 6, P W J Rigby, ed, London, Academic Press, 1987; and Lichtenstein, C. P., and Draper, J., In: *DNA Cloning*, Vol II, D. M. Glover, ed, Oxford, IRI Press, 1985; U.S. Pat. Nos. 4,693,976, 4,762,785, 4,940,838, 5,004,863, 5,104,310, 5,149,645, 5,159,135, 5,177,010, 5,231,019, 5,463,174, 5,469,976, and 5,464,763; and European Patent Application Numbers 0131624B1, 0159418B1, 0120516, 0176112, 0116718, 0267159, 0290799, 0292435, 0320500, 0604622, and 0627752), (2) the particle delivery system (see, for example, U.S. Pat. Nos. 4,945,050 and 5,141,131), (3) microinjection protocols, (4) polyethylene glycol (PEG) procedures, (5) liposome-mediated DNA uptake, (6) electroporation protocols (see, for example, WO 87/06614, WO 92/09696, and WO 93/21335; and U.S. Pat. Nos. 5,384,253 and 5,472,869, (7) the vortexing method, or (8) the so-called whiskers methodology (see, for example, Coffee et al., U.S. Pat. Nos. 5,302,523 and 5,464,765). The type of plant tissue that may be transformed with an expression vector includes embryonic tissue, callus tissue type I and II, hypocotyls, meristem, and the like.

Once introduced into the plant tissue, the expression of the structural gene may be assayed by any means known to the art, and expression may be measured as mRNA transcribed, protein synthesized, or the amount of gene silencing that occurs as determined by metabolite monitoring via chemical analysis of secondary alkaloids in tobacco (as described herein; see also U.S. Pat. No. 5,583,021 which is hereby incorporated by reference). Techniques are known for the in vitro culture of plant tissue, and in a number of cases, for regeneration into whole plants (see, e.g., U.S. Pat. Nos. 5,595,733 and 5,766,900). Procedures for transferring the introduced expression complex to commercially useful cultivars are known to those skilled in the art.

Once plant cells expressing the desired level of nicotine demethylase (or nornicotine or NNN or both) are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

Transgenic tobacco plants may incorporate a nucleic acid of any portion of the genomic gene in different orientations for either down-regulation, for example, antisense orientation or in a form to induce RNAi, or over-expression, for example, sense orientation. Over-expression of the nucleic acid sequence that encodes the entire or a functional part of an amino acid sequence of a full-length tobacco nicotine demethylase gene is desirable for increasing the expression of nicotine demethylase within *Nicotiana* lines.

Determination of Transcriptional or Translational Levels of a Tobacco Nicotine Demthylase Tobacco nicotine demethylase expression may be measured, for example, by standard Northern blot analysis (Ausubel et al., *Current Protocols in Molecular Biology*, John Wiley & Sons, New York, N.Y., (2001), and Sambrook et al., *Molecular Cloning: A Laboratory Manual*, Cold Spring Harbor Laboratory, N.Y., (1989)) using a tobacco nicotine demethylase (or cDNA fragment) as a hybridization probe. Determination of RNA expression levels may also be aided by reverse transcription PCR (rtPCR), including quantitative rtPCR (see, e.g., Kawasaki et al., in PCR Technology: Principles and Applications of DNA Amplification (H. A. Erlich, Ed.) Stockton Press (1989); Wang et al. in PCR Protocols: A Guide to Methods and Applications (M. A. Innis, et al., Eds.) Academic Press (1990); and Freeman et al., *Biotechniques* 26:112-122 and 124-125, 1999). Additional well-known techniques for determining expression of a tobacco nicotine demethylase gene include in situ hybridization, and fluorescent in situ hybridization (see, e.g., Ausubel et al., *Current Protocols in Molecular Biology*, John Wiley & Sons, New York, N.Y., (2001)). The above standard techniques are also useful to compare the expression level between plants, for example, between a plant having a mutation in a tobacco nicotine demethylase gene and a control plant.

If desired, expression of a tobacco nicotine demethylase gene may be measured at the level of tobacco nicotine demethylase protein production using the same general approach and standard protein analysis techniques including Bradford assays, spectrophotometric assays, and immunological detection techniques, such as Western blotting or immunoprecipitation with a tobacco nicotine demethylase-specific antibody (Ausubel et al., *Current Protocols in Molecular Biology*, John Wiley & Sons, New York, N.Y., (2001), and Sambrook et al., *Molecular Cloning: A Laboratory Manual*, Cold Spring Harbor Laboratory, N.Y., (1989)).

Identification of Modulators of a Tobacco Nicotine Demethylase

Isolation of a tobacco nicotine demethylase cDNA also facilitates the identification of molecules that increase or decrease expression a tobacco nicotine demethylase. According to one approach, candidate molecules are added at varying concentrations to a culture medium of cells (for example, prokaryotic cells such as *E. coli* or eukaryotic cells such as yeast, mammalian, insect, or plant cells) expressing a tobacco nicotine demethylase mRNA. Tobacco nicotine demethylase expression is then measured in the presence and absence of a candidate molecule using standard methods such as those set forth herein.

Candidate modulators may be purified (or substantially purified) molecules or may be one component of a mixture of compounds. In a mixed compound assay, tobacco nicotine demethylase expression is tested against progressively smaller subsets of the candidate compound pool (for example, produced by standard purification techniques, for example, HPLC) until a single compound or minimal compound mixture is demonstrated to alter tobacco nicotine demethylase gene expression. A molecule that promotes a decrease in tobacco nicotine demethylase expression is considered particularly useful in the invention. Modulators found to be effective at the level of tobacco nicotine demethylase expression or activity may be confirmed as useful in planta.

For agricultural uses, the molecules, compounds, or agents identified using the methods disclosed herein may be used as chemicals applied as sprays or dusts on the foliage of plants. The molecules, compounds, or agents may also be applied to plants in combination with another molecule which affords some benefit to the plant.

Uses of the Nicotine Demethylase Gene Promoter and Non-Translated Regions

The promoter region of the nicotine demethylase gene described herein is ethylene inducible or related to plant senescence. Accordingly, this promoter could be used to drive the expression of any desirable gene products to improve crop quality or enhance specific traits. As the tobacco nicotine demethylase promoter (e.g., SEQ ID NO:6) is inducible and expressed during a particular period of the plant's life cycle, constructs containing this promoter can be introduced to the plant to express unique genes involved in the biosynthesis of flavor and aroma products that result from secondary metabolites. Examples of such compounds are compounds in the terpenoid pathway, other alkaloids, plant hormones, flavonoids, or sugar-containing moieties. A tobacco nicotine demethylase promoter may also be used to increase or modify the expression of structural carbohydrates or proteins that affect end-use properties. Further, a tobacco nicotine demethylase promoter could also be combined with heterologous genes that include genes involved in the biosynthesis of nutritional products, pharmaceutical agents, or industrial materials. The promoter may be used to drive the down-regulation of genes endogenous to tobacco including nicotine demethylase or other genes involved in alkaloid biosynthesis and or in other pathways.

Moreover, the promoter region (e.g., SEQ ID NO:6) of a tobacco nicotine demethylase genes or the 3' UTR (e.g., SEQ ID NO:7) of a tobacco nicotine demethylase gene may also be used in any site-directed gene silencing methods such as T-DNA tagging, gene trapping and homologous recombination to alter the expression pattern of a target gene, as described herein. Promoter motifs, which can readily be identified in a promoter sequence, such as the sequence of SEQ ID NO:6 using standard methods in the art, may also be used to identify factors that associate with or regulate the expression of a tobacco nicotine demethylase. Desirably, a tobacco nicotine demethylase promoter region or other transcriptional regulatory region is used to alter chemical properties such as nornicotine content and nitrosamine levels in a plant.

Furthermore, any portion of a tobacco nicotine demethylase gene can be used as a genetic marker to isolate related genes, promoters or regulatory regions, or for screening for the demethylase gene in other tobacco or *Nicotiana* species.

Products

Tobacco products having a reduced amount of nitrosamine content are manufactured using any of the tobacco plant material described herein according to standard methods known in the art. In one embodiment, tobacco products are manufactured using plant material obtained from a genetically modified cured tobacco having a reduced amount of nornicotine or NNN of less than about 5 mg/g, 4.5 mg/g, 4.0 mg/g, 3.5 mg/g, 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 7.0 µg/g, 5.0 µg/g, 4.0 µg/g, 2.0 µg/g, 1.0 µg/g, 0.5 µg/g, 0.4 µg/g, 0.2 µg/g, 0.1 µg/g, 0.05 µg/g, or 0.01 µg/g or wherein the percentage of secondary alkaloids relative to total alkaloid content contained therein is less than 90%, 70%, 50%, 30%, 10%, 5%, 4%, 3%, 2%, 1.5%, 1%, 0.75%, 0.5%, 0.25%, or 0.1%. That is, the cured tobacco is made from a genetically modified tobacco plant. The phrase "a reduced amount" is intended to refer to an amount of nornicotine or NNN or both in a transgenic tobacco plant, tobacco or a tobacco product that is less than what would be found in a naturally-occurring tobacco plant, tobacco or a tobacco product from the same variety of tobacco, processed in the same manner, which was not made transgenic material for reduced nornicotine or NNN. Thus, in some contexts, a naturally-occurring tobacco of the same variety that has been processed in the same manner is used as a control by which to measure whether a reduction of nornicotine or NNN has been obtained by the methods described herein. Levels of nornicotine and NNN are measured according to methods well known in the tobacco art.

The following examples illustrate methods for carrying out the invention and should be understood to be illustrative of, but not limiting upon, the scope of the invention which is defined in the appended claims.

Example 1

Development of Plant Tissue and Ethylene Treatment

Plant Growth

Plants were seeded in pots and grown in a greenhouse for 4 weeks. The 4-week old seedlings were transplanted into individual pots and grown in the greenhouse for 2 months. The plants were watered 2 times a day with water containing 150 ppm NPK fertilizer during growth. The expanded green leaves were detached from plants to do the ethylene treatment described below.

Cell Line 78379

Tobacco line 78379, which is a burley tobacco line released by the University of Kentucky was used as a source of plant material. One hundred plants were cultured as standard in the an of growing tobacco, transplanted, and tagged with a distinctive number (1-100). Fertilization and field management were conducted as recommended.

Three quarters of the 100 plants converted between 20 and 100% of the nicotine to nornicotine. One quarter of the 100 plants converted less than 5% of the nicotine to nornicotine. Plant number 87 had the least conversion (2%) while plant number 21 had 100% conversion. Plants converting less than 3% were classified as non-converters. Self-pollinated seed of plant number 87 and plant number 21, as well as crossed (21×87 and 87×21) seeds were made to study genetic and phenotypic differences. Plants from selfed 21 were converters, and 99% of selfs from 87 were non-converters. The other 1% of the plants from 87 showed low conversion (5-15%). Plants from reciprocal crosses were all converters.

Cell Line 4407

*Nicotiana* line 4407, which is a burley line, was used as a source of plant material. Uniform and representative plants (100) were selected and tagged. Of the 100 plants 97 were non-converters and three were converters. Plant number 56 had the least amount of conversion (1.2%) and plant number 58 had the highest level of conversion (96%). Self-pollinated seeds and crossed seeds were made with these two plants.

Plants from selfed-58 segregated with 3:1 converter to non-converter ratio. Plants 58-33 and 58-25 were identified as homozygous converter and nonconverter plant lines, respectively. The stable conversion of 58-33 was confirmed by analysis of its progeny.

Cell Line PBLB01

PBLB01 is a burley line developed by ProfiGen, Inc. and was used as a source of plant material. The converter plant was selected from foundation seeds of PBLB01.

Ethylene Treatment Procedures

Green leaves were detached from 2-3 month greenhouse grown plants and sprayed with 0.3% ethylene solution (Prep brand Ethephon (Rhone-Poulenc)). Each sprayed leaf was hung in a curing rack equipped with humidifier and covered with plastic. During the treatment, the sample leaves were periodically sprayed with the ethylene solution. Approximately 24-48 hour post ethylene treatment, leaves were collected for RNA extraction. Another sub-sample was taken for metabolic constituent analysis to determine the concentration of leaf metabolites and more specific constituents of interest such as a variety of alkaloids.

As an example, alkaloids analysis could be performed as follows. Samples (0.1 g) were shaken at 150 rpm with 0.5 ml 2N NaOH, and a 5 ml extraction solution which contained quinoline as an internal standard and methyl t-butyl ether. Samples were analyzed on a HP 6890 GC equipped with a FID detector. A temperature of 250° C. was used for the detector and injector. An HP column (30 m-0.32 nm-1 mm) consisting of fused silica crosslinked with 5% phenol and 95% methyl silicon was used at a temperature gradient of 110-185° C. at 10° C. per minute. The column was operated at 100° C. with a flow rate of 1.7 cm$^3$ min$^{-1}$ with a split ratio of 40:1 with a 2:1 injection volume using helium as the carrier gas.

Example 2

RNA Isolation

For RNA extractions, middle leaves from two-month old greenhouse grown plants were treated with ethylene as described above. The 0 and 24-48 hours samples were used for RNA extraction. In some cases, leaf samples under the senescence process were taken from the plants 10 days post flower-head removal. These samples were also used for extraction. Total RNA was isolated using Rneasy Plant Mini Kit® (Qiagen, Inc., Valencia, Calif.) according to the manufacturer's protocol.

The tissue sample was ground under liquid nitrogen to a fine powder using a DEPC treated mortar and pestle. Approximately 100 milligrams of ground tissue were transferred to a sterile 1.5 ml Eppendorf tube. This sample tube was placed in liquid nitrogen until all samples were collected. Then, 45 µl of Buffer RLT as provided in the kit (with the addition of Mercaptoethanol) was added to each individual tube. The sample was vortexed vigorously and incubated at 56° C. for 3 minutes. The lysate was then applied to the QIAshredder® spin column sitting in a 2 ml collection tube, and centrifuged for 2 minutes at maximum speed. The flow through was collected and 0.5 volume of ethanol was added to the cleared lysate. The sample was mixed well and transferred to an Rneasy® mini spin column sitting in a 2 ml collection tube. The sample was centrifuged for 1 minute at 10,000 rpm. Next, 70 µl of buffer RW1 was pipetted onto the Rneasy® column and centrifuged for 1 minute at 10,000 rpm. Buffer RPE was pipetted onto the Rneasy® column in a new collection tube and centrifuged for 1 minute at 10,000 rpm. Buffer RPE was again, added to the Rneasy® spin column and centrifuged for 2 minutes at maximum speed to dry the membrane. To eliminate any ethanol carry over, the membrane was placed in a separate collection tube and centrifuged for an additional 1 minute at maximum speed. The Rneasy® column was transferred into a new 1.5 ml collection tube, and 40 µl of Rnase-free water was pipetted directly onto the Rneasy® membrane. This final elute tube was centrifuged for 1 minute at 10,000 rpm. Quality and quantity of total RNA was analyzed by denatured formaldehyde gel and spectrophotometer.

Poly(A)RNA was isolated using Oligotex® poly A+ RNA purification kit (Qiagen Inc.) following the manufacture's protocol. About 200 µg total RNA in 250 µl maximum volume was used. A volume of 250 µl of Buffer OBB and 15 µl of Oligotex® suspension was added to the 250 µl of total RNA. The contents were mixed thoroughly by pipetting and incubated for 3 minutes at 70° C. on a heating block. The sample was then placed at room temperature for approximately 20 minutes. The Oligotex®: mRNA complex was pelleted by centrifugation for 2 minutes at maximum speed. All but 50 µl of the supernatant was removed from the microcentrifuge tube. The sample was treated further by OBB buffer. The Oligotex®: mRNA pellet was resuspended in 400 µl of Buffer OW2 by vortexing. This mix was transferred onto a small spin column placed in a new tube and centrifuged for 1 minute at maximum speed. The spin column was transferred to a new tube and an additional 400 µl of Buffer OW2 was added to the column. The tube was then centrifuged for 1 minute at maximum speed. The spin column was transferred to a final 1.5 ml microcentrifuge tube. The sample was eluted with 60 µl of hot (70° C.) Buffer OEB. Poly A product was analyzed by denatured formaldehyde gels and spectrophotometric analysis.

Example 3

Reverse-Transcription-PCR

First strand cDNA was produced using SuperScript reverse transcriptase following the manufacturer's protocol (Invitrogen, Carlsbad, Calif.). The poly A+ enriched RNA/oligo dT primer mix consisted of less than 5 μg of total RNA, 1 μl of 10 mM dNTP mix, 1 μl of Oligo d(T)$_{12\_18}$ (0.5 μg/μl), and up to 10 μl of DEPC-treated water. Each sample was incubated at 65° C. for 5 minutes, then placed on ice for at least 1 minute. A reaction mixture was prepared by adding each of the following components in order: 2 μl 10×RT buffer, 4 μl of 25 mM MgCl$_2$, 2 μl of 0.1 M DTT, and 1 μl of RNase OUT Recombinant RNase Inhibitor. An addition of 9 μl of reaction mixture was pipetted to each RNA/primer mixture and gently mixed. It was incubated at 42° C. for 2 minutes and 1 μl of Super Script II RT was added to each tube. The tube was incubated for 50 minutes at 42° C. The reaction was terminated at 70° C. for 15 minutes and chilled on ice. The sample was collected by centrifugation and 1 μl of RNase H was added to each tube and incubated for 20 minutes at 37° C. The second PCR was carried out with 200 pmoles of forward primer and 100 pmoles reverse primer (mix of 18 nt oligo d(T) followed by 1 random base).

Reaction conditions were 94° C. for 2 minutes and then 40 cycles of PCR at 94° C. for 1 minute, 45° C. to 60° C. for 2 minutes, 72° C. for 3 minutes, with a 72° C. extension for an extra 10 min. Ten microliters of the amplified sample were analyzed by electrophoresis using a 1% agarose gel. The correct size fragments were purified from agarose gel.

Example 4

Generation of PCR Fragment Populations

PCR fragments from Example 3 were ligated into a pGEM-T Easy Vector (Promega, Madison, Wis.) following the manufacturer's instructions. The ligated product was transformed into JM 109 competent cells and plated on LB media plates for blue/white selection. Colonies were selected and grown in a 96 well plate with 1.2 ml of LB media overnight at 37° C. Frozen stock was generated for all selected colonies. Plasmid DNA was purified from plates using Beckman's Biomeck 2000 miniprep robotics with Wizard SV Miniprep kit (Promega). Plasmid DNA was eluted with 100 μl water and stored in a 96 well plate. Plasmids were digested by EcoR1 and were analyzed using 1% agarose gel to confirm the DNA quantity and size of inserts. Plasmids containing a 400-600 bp insert were sequenced using a CEQ 2000 sequencer (Beckman, Fullerton, Calif.). The sequences were aligned with GenBank database by BLAST search. The p450 related fragments were identified and further analyzed. Alternatively, p450 fragments were isolated from subtraction libraries. These fragments were also analyzed as described above.

Example 5 cDNA Library Construction

A cDNA library was constructed by preparing total RNA from ethylene treated leaves as follows. First, total RNA was extracted from ethylene treated leaves of tobacco line 58-33 using a modified acid phenol and chloroform extraction protocol. The protocol was modified to use one gram of tissue that was ground and subsequently vortexed in 5 ml of extraction buffer (100 mM Tris-HCl, pH 8.5; 200 mM NaCl; 10 mM EDTA; 0.5% SDS) to which 5 ml phenol (pH5.5) and 5 ml chloroform was added. The extracted sample was centrifuged and the supernatant was saved. This extraction step was repeated 2-3 times until the supernatant appeared clear. Approximately 5 ml of chloroform was added to remove trace amounts of phenol. RNA was precipitated from the combined supernatant fractions by adding a 3-fold volume of ethanol and ¹⁄₁₀ volume of 3M NaOAc (pH5.2) and storing at −20° C. for 1 hour. After transfer to a Corex glass container the RNA fraction was centrifuged at 9,000 RPM for 45 minutes at 4° C. The pellet was washed with 70% ethanol and spun for 5 minutes at 9,000 RPM at 4° C. After drying the pellet, the pelleted RNA was dissolved in 0.5 ml RNase free water. The quality and quantity of total RNA was analyzed by denatured formaldehyde gel and spectrophotometer, respectively.

The resultant total RNA was used to isolate poly A+ RNA using an Oligo(dT) cellulose protocol (Invitrogen) and microcentrifuge spin columns (Invitrogen) by the following protocol. Approximately twenty mg of total RNA was twice subjected to purification to obtain high quality poly A+ RNA. Poly A+ RNA product was analyzed by performing denatured formaldehyde gel and subsequent RT-PCR of known full-length genes to ensure high quality of mRNA.

Next, poly A+ RNA was used as template to produce a cDNA library employing cDNA synthesis kit, ZAP-cDNA synthesis kit, and ZAP-cDNA Gigapack III gold cloning kit (Stratagene, La Jolla, Calif.). The method involved following the manufacture's protocol as specified. Approximately 8 μg of poly A+ RNA was used to construct cDNA library. Analysis of the primary library revealed about $2.5 \times 10^6$-$1 \times 10^7$ pfu. A quality background test of the library was completed by complementation assays using IPTG and X-gal, where recombinant plaques was expressed at more than 100-fold above the background reaction.

A more quantitative analysis of the library by random PCR showed that average size of insert cDNA was approximately 1.2 kb. The method used a two-step PCR method. For the first step, reverse primers were designed based on the preliminary sequence information obtained from p450 fragments. The designed reverse primers and T3 (forward) primers were used to amplify corresponding genes from the cDNA library. PCR reactions were subjected to agarose electrophoresis and the corresponding bands of high molecular weight were excised, purified, cloned and sequenced. In the second step, new primers designed from 5'UTR or the start coding region of p450 as the forward primers together with the reverse primers (designed from 3'UTR of p450) were used in the subsequent PCR to obtain full-length p450 clones.

The p450 fragments were generated by PCR amplification from the constructed cDNA library as described in Example 3 with the exception of the reverse primer. The T7 primer located on the plasmid downstream of cDNA inserts was used as a reverse primer. PCR fragments were isolated, cloned and sequenced as described in Example 4.

Full-length p450 genes were isolated by this PCR method from constructed cDNA library. Gene specific reverse primers (designed from the downstream sequence of p450 fragments) and a forward primer (T3 on library plasmid) were used to clone the full-length genes. PCR fragments were isolated, cloned and sequenced. If necessary, a second PCR step was applied. In the second step, new forward primers designed from 5'UTR of cloned p450s together with the reverse primers designed from 3'UTR of p450 clones were used in the subsequent PCR reactions to obtain full-length p450 clones. The clones were subsequently sequenced.

Example 6

Characterization of Cloned Fragments

Reverse Southern Blotting Analysis

Nonradioactive large-scale reverse Southern blotting assays were performed on all p450 clones identified in above examples to detect the differential expression. It was observed that the level of expression among different p450 clusters was very different. Further real time detection was conducted on those with high expression.

Nonradioactive Southern blotting procedures were conducted as follows.

1) Total RNA was extracted from ethylene treated and nontreated converter (58-33) and nonconverter (58-25) leaves using the Qiagen Rnaeasy kit as described in Example 2.

2) A probe was produced by biotin-tail labeling a single strand cDNA derived from poly A+ enriched RNA generated in above step. This labeled single strand cDNA was generated by RT-PCR of the converter and nonconverter total RNA (Invitrogen) as described in Example 3 with the exception of using biotinylated oligo dT as a primer (Promega). These were used as a probe to hybridize with cloned DNA.

3) Plasmid DNA was digested with restriction enzyme EcoR1 and run on agarose gels. Gels were simultaneously dried and transferred to two nylon membranes (Biodyne B). One membrane was hybridized with converter probe and the other with nonconverter probe. Membranes were UV-crosslinked (auto crosslink setting, 254 nm, Stratagene, Stratalinker) before hybridization.

Alternatively, the inserts were PCR amplified from each plasmid using the sequences located on both arms of p-GEM plasmid, T3 and SP6, as primers. The PCR products were analyzed by running on a 96 well Ready-to-run agarose gels. The confirmed inserts were dotted on two nylon membranes. One membrane was hybridized with converter probe and the other with nonconverter probe.

4) The membranes were hybridized and washed following the manufacture's instructions with the modification of washing stringency (Enzo MaxSence kit, Enzo Diagnostics, Inc, Farmingdale, N.Y.). The membranes were prehybridized with hybridization buffer (2×SSC buffered formamide, containing detergent and hybridization enhancers) at 42° C. for 30 min and hybridized with 10 µl denatured probe overnight at 42° C. The membranes then were washed in 1× hybridization wash buffer 1 time at room temperature for 10 min and 4 times at 68° C. for 15 min. The membranes were ready for the detection procedure.

5) The washed membranes were detected by alkaline phosphatase labeling followed by NBT/BCIP colometric detection as described in manufacture's detection procedure (Enzo Diagnostics, Inc.). The membranes were blocked for one hour at room temperature with 1× blocking solution, washed 3 times with 1× detection reagents for 10 min, washed 2 times with 1× predevelopment reaction buffer for 5 min and then developed the blots in developing solution for 30-45 min until the dots appear. All reagents were provided by the manufacturer (Enzo Diagnostics, Inc). In addition, large-scale reverse Southern assay was also performed using KPL Southern hybridization and detection kit following the manufacturer's instructions (KPL, Gaithersburg, Md.).

Example 7

Characterization of Clones

Northern Blot Analysis

As an alternative to Southern blot analysis, some membranes were hybridized and detected as described in the example of Northern blotting assays. Northern hybridization was used to detect mRNA differentially expressed in *Nicotiana* as follows.

A random priming method was used to prepare probes from cloned p450 (Megaprime DNA Labelling Systems, Amersham Biosciences). The following components were mixed: 25 ng denatured DNA template; 4 ul of each unlabeled dTTP, dGTP and dCTP; 5 ul of reaction buffer; $P^{32}$-labelled dATP and 2 ul of Klenow I; and H20, to bring the reaction to 5 µl. The mixture was incubated in 37° C. for 1-4 hours, and stopped with 2 µl of 0.5 M EDTA. The probe was denatured by incubation at 95° C. for 5 minutes before use.

RNA samples were prepared from ethylene treated and non-treated fresh leaves of several pairs of tobacco lines. In some cases poly A+ enriched RNA was used. Approximately 15 µg total RNA or 1.8 µg mRNA (methods of RNA and mRNA extraction as described in Example 5) were brought to equal volume with DEPC H2O (5-10 µl). The same volume of loading buffer (1×MOPS; 18.5% Formaldehyde; 50% Formamide; 4% Ficol1400; Bromophenolblue) and 0.5 µl EtBr (0.5 µg/µl) were added. The samples were subsequently denatured in preparation for separation of the RNA by electrophoresis.

Samples were subjected to electrophoresis on a formaldehyde gel (1% Agarose, 1×MOPS, 0.6 M Formaldehyde) with 1×MOP buffer (0.4 M Morpholinopropanesulfonic acid; 0.1 M Na-acetate-3×H2O; 10 mM EDTA; adjust to pH 7.2 with NaOH). RNA was transferred to a Hybond-N+ membrane (Nylon, Amersham Pharmacia Biotech) by capillary method in 10×SSC buffer (1.5 M NaCl; 0.15 M Na-citrate) for 24 hours. Membranes with RNA samples were UV-crosslinked (auto crosslink setting, 254 nm, Stratagene, Stratalinker) before hybridization.

The membrane was prehybridized for 1-4 hours at 42° C. with 5-10 ml prehybridization buffer (5×SSC; 50% Formamide; 5×Denhardt's-solution; 1% SDS; 1001·tg/ml heat-denatured sheared non-homologous DNA). Old prehybridization buffer was discarded, and new prehybridization buffer and probe were added. The hybridization was carried out overnight at 42° C. The membrane was washed for 15 minutes with 2×SSC at room temperature, followed by a wash with 2×SSC.

Northern analysis was performed using full-length clones on tobacco tissue obtained from converter and nonconverter burley lines that were induced by ethylene treatment. The purpose was to identify those full-length clones that showed elevated expression in ethylene induced converter lines relative to ethylene induced converter lines relative to ethylene induced nonconverter burley lines. By so doing, the functionality relationship of full-length clones may be determined by comparing biochemical differences in leaf constituents between converter and nonconverter lines.

Example 8

Immunodetection of p450s Encoded by the Cloned Genes

Peptide regions corresponding to 20-22 amino acids in length from three p450 clones were selected for 1) having lower or no homology to other clones and 2) having good hydrophilicity and antigenicity. The amino acid sequences of the peptide regions selected from the respective p450 clones are listed below. The synthesized peptides were conjugated with KHL and then injected into rabbits. Antisera were collected 2 and 4 weeks after the 4' h injection (Alpha Diagnostic Intl. Inc. San Antonio, Tex.).

```
D234-AD1    DIDGSKSKLVKAHRKIDEILG    (SEQ ID NO: 8)
D90a-BB3    RDAFREKETFDENDVEELNY    (SEQ ID NO: 9)
D89-AB 1    FKNNGDEDRHFSQKLGDLADKY  (SEQ ID NO: 10)
```

Antisera were examined for crossreactivity to target proteins from tobacco plant tissue by Western Blot analysis. Crude protein extracts were obtained from ethylene treated (0 to 40 hours) middle leaves of converter and nonconverter lines. Protein concentrations of the extracts were determined using RC DC Protein Assay Kit (BIO-RAD) following the manufacturer's protocol.

Two micrograms of protein were loaded onto each lane and the proteins were separated on 10%-20% gradient gels using the Laemmli SDS-PAGE system. The proteins were transferred from gels to PROTRAN Nitrocellulose Transfer Membranes (Schleicher & Schuell) with the Trans-Blot Semi-Dry cell (BIO-RAD). Target p450 proteins were detected and visualized with the ECL Advance Western Blotting Detection Kit (Amersham Biosciences). Primary antibodies against the synthetic-KLH conjugates were made in rabbits. Secondary antibody against rabbit IgG, coupled with peroxidase, was purchased from Sigma. Both primary and secondary antibodies were used at 1:1000 dilutions. Antibodies showed strong reactivity to a single band on the Western Blots indicating that the antisera were monospecific to the target peptide of interest. Antisera were also crossreactive with synthetic peptides conjugated to KLH.

Example 9

Nucleic Acid Identity and Structure Relatedness of Isolated Nucleic Acid Fragments Over 100 cloned p450 fragments were sequenced in conjunction with Northern blot analysis to determine their structural relatedness. The approach used forward primers based either of two common p450 motifs located near the carboxyl-terminus of the p450 genes. The forward primers corresponded to cytochrome p450 motifs FXPERF (SEQ ID NO:11) or GRRXCP(A/G) (SEQ ID NO:12). The reverse primers used standard primers from either the plasmid, SP6 or T7 located on both arms of pGEM plasmid, or a poly A tail. The protocol used is described below.

Spectrophotometry was used to estimate the concentration of starting double stranded DNA following the manufacturer's protocol (Beckman Coulter). The template was diluted with water to the appropriate concentration, denatured by heating at 95° C. for 2 minutes, and subsequently placed on ice. The sequencing reaction was prepared on ice using 0.5 to 10 µl of denatured DNA template, 2 µl of 1.6 pmole of the forward primer, 8 µl of DTCS Quick Start Master Mix and the total volume brought to 20 µl with water. The thermocycling program consisted of 30 cycles of the follow cycle: 96° C. for 20 seconds, 50° C. for 20 seconds, and 60° C. for 4 minutes followed by holding at 4° C.

The sequencing reaction was stopped by adding 5 µl of stop buffer (equal volume of 3M NaOAc and 100 mM EDTA and 1 µl of 20 mg/ml glycogen). The sample was precipitated with 60 µl of cold 95% ethanol and centrifuged at 6000×g for 6 minutes. Ethanol was discarded. The pellet was 2 washes with 200 µl of cold 70% ethanol. After the pellet was dry, 40 µl of SLS solution was added and the pellet was resuspended. A layer of mineral oil was over laid. The sample was then, placed on the CEQ 8000 Automated Sequencer for further analysis.

In order to verify nucleic acid sequences, nucleic acid sequence was re-sequenced in both directions using forward primers to the FXPERF (SEQ ID NO:11) or GRRXCP(A/G) (SEQ ID NO:12) region of the p450 gene or reverse primers to either the plasmid or poly A tail. All sequencing was performed at least twice in both directions.

The nucleic acid sequences of cytochrome p450 fragments were compared to each other from the coding region corresponding to the first nucleic acid after the region encoding the GRRXCP(AIG) (SEQ ID NO:12) motif through to the stop codon. This region was selected as an indicator of genetic diversity among p450 proteins. A large number of genetically distinct p450 genes, in excess of 70 genes, were observed, similar to that of other plant species. Upon comparison of nucleic acid sequences, it was found that the genes could be placed into distinct sequences groups based on their sequence identity. It was found that the best unique grouping of p450 members was determined to be those sequences with 75% nucleic acid identity or greater. (See e.g., Table 1 of the US 2004/0162420 patent application publication, which is incorporated herein by reference.) Reducing the percentage identity resulted in significantly larger groups. A preferred grouping was observed for those sequences with 81% nucleic acid identity or greater, a more preferred grouping 91% nucleic acid identity or greater, and a most preferred grouping for those sequences 99% nucleic acid identity of greater. Most of the groups contained at least two members and frequently three or more members. Others were not repeatedly discovered suggesting that approach taken was able to isolated both low and high expressing mRNA in the tissue used.

Using GeneChip technology to identify genes that are differentially expressed in converter versus non-converter tobacco lines, it was determined that D121-AA8 had reproducible induction in ethylene-treated converter lines. Based on these results, the D121-AA8 gene (the cDNA sequence of which is the sequence of SEQ ID NO:3; FIG. 3) was identified as the tobacco nicotine demethylase gene of interest.

In view of the p450 nomenclature rule, the tobacco nicotine demethylase gene is novel and belongs to CYP82E class (The *Arabidopsis* Genome Initiative (AGI) and The *Arabidopsis* Information Resource (TAIR); Frank, *Plant Physiol.* 110: 1035-1046, 1996; Whitbred et al., *Plant Physiol.* 124:47-58, 2000); Schopfer and Ebel, *Mol. Gen. Genet.* 258:315-322, 1998; and Takemoto et al., *Plant Cell Physiol.* 40:1232-1242, 1999).

Example 10

Biochemical Analysis of the Tobacco Nicotine Demethylase

Biochemical analysis, for example, as described in previously filed applications that are incorporated herein by reference, determined that the sequence of SEQ ID NO:3 encodes a tobacco nicotine demethylase (SEQ ID NO:4; FIG. 3).

In particular, the function of the candidate clone (D121-AA8), was confirmed as the coding gene for nicotine demethylase, by assaying enzyme activity of heterologously expressed p450 in yeast cells as follows.

1. Construction of Yeast Expression Vector

The putative protein-coding sequence of the tobacco nicotine demethylase-encoding cDNA (D 121 AA8), was cloned into the yeast expression vector pYeDP60. Appropriate BamHI and Mfel sites (underlined below) were introduced via PCR primers containing these sequences either upstream of the translation start codon (ATG) or downstream of the stop codon (TAA). The Mfel on the amplified PCR product is compatible with the EcoRI site on the vector. The primers used to amplify the cDNA were 5'-TAGCTACGCGGATC-CATGCTTTCTCCCATAGAAGCC-3' (SEQ ID NO:27) and 5'-CTGGATCACAATTGTTAGTGATGGT-GATGGTGATGCGATCCTCTATAAAGCTCAGGT GCCAGGC-3' (SEQ ID NO:28). A segment of sequence coding nine extra amino acids at the C-terminus of the protein, including six histidines, was incorporated into the reverse primer to facilitate expression of 6-His tagged p450 upon induction. PCR products were ligated into pYeDP60 vector after enzyme digestions in the sense orientation with reference to the GAL10-CYC 1 promoter. Proper construction of the yeast expression vectors was verified by restriction enzyme analysis and DNA sequencing.

2. Yeast Transformation

The WAT11 yeast line, modified to express *Arabidopsis* NADPH-cytochrome p450 reductase ATR1, was transformed with the pYeDP60-p450 cDNA plasmids. Fifty micro-liters of WAT11 yeast cell suspension was mixed with ~1 μg plasmid DNA in a cuvette with 0.2 cm electrode gap. One pulse at 2.0 kV was applied by an Eppendorf electroporator (Model 2510). Cells were spread onto SGI plates (5 g/L bactocasamino acids, 6.7 g/L yeast nitrogen base without amino acids, 20 g/L glucose, 40 mg/L DL-tryptophan, 20 g/L agar). Transformants were confirmed by PCR analysis performed directly on randomly selected colonies.

3. p450 Expression in Transformed Yeast Cells

Single yeast colonies were used to inoculate 30 mL SGI media (5 g/L bactocasamino acids, 6.7 g/L yeast nitrogen base without amino acids, 20 g/L glucose, 40 mg/L DL-tryptophan) and grown at 30° C. for about 24 hours. An aliquot of this culture was diluted 1:50 into 1000 mL of YPGE media (10 g/L yeast extract, 20 g/L bacto peptone, 5 g/L glucose, 30 ml/L ethanol) and grown until glucose was completely consumed as indicated by the colorimetric change of a Diastix urinalysis reagent strip (Bayer, Elkhart, Ind.). Induction of cloned P450 was initiated by adding DL-galactose to a final concentration of 2%. The cultures were grown for an additional 20 hours before used for in vivo activity assay or for microsome preparation.

WATT 1 yeast cells expressing pYeDP60-CYP71D20 (a p450 catalyzing the hydroxylation of 5-epi-aristolochene and 1-deoxycapsidiol in *Nicotiana tabacum*) were used as control for the p450 expression and enzyme activity assays.

To evaluate the effectiveness of the yeast expression of the p450 in great detail, reduced CO difference spectroscopy was performed. The reduced CO spectrum exhibited a peak at 450 nm proteins from all four p450 transformed yeast lines. No similar peaks were observed in the microsomes of the control yeast or the vector control yeast. The results indicated that p450 proteins were expressed effectively in yeast lines harboring the pYeDP60-CYP 450. Concentrations of expressed p450 protein in yeast microsome ranged from 45 to 68 nmole/mg of total protein.

4. In Vivo Enzyme Assay

The nicotine demethylase activity in the transformed yeast cells were assayed by feeding of yeast culture with DL-Nicotine (Pyrrolidine-2-$^{14}$C). 14C labeled nicotine (54 mCi/mmol) was added to 75 μl of the galactose-induced culture for a final concentration of 55 μM. The assay culture was incubated with shaking in 14 ml polypropylene tubes for 6 hours and was extracted with 900 μl methanol. After spinning, 20 μl of the methanol extract was separated with an rp-HPLC and the nornicotine fraction was quantitated by LSC.

The control culture of WAT11 (pYeDP60-CYP71D20) did not convert nicotine to nornicotine, showing that the WAT11 yeast strain does not contain endogenous enzyme activities that can catalyze the step of nicotine bioconversion to nornicotine. In contrast, yeast expressing the tobacco nicotine demethylase gene produced detectable amount of nornicotine, indicating the nicotine demethylase activity of the translation product of SEQ ID NO:3.

5. Yeast Microsome Preparation

After induction by galactose for 20 hours, yeast cells were collected by centrifugation and washed twice with TES-M buffer (50 mM Tris-HCl, pH 7.5, 1 mM EDTA, 0.6 M sorbitol, 10 mM 2-mercaptoethanol). The pellet was resuspended in extraction buffer (50 mM Tris-HCl, pH 7.5, 1 mM EDTA, 0.6 M sorbitol, 2 mM 2-mercaptoethanol, 1% bovine serum album, Protease Inhibitor Cocktail (Roche) at 1 tablet/50 ml). Cells were then broken with glass beads (0.5 mm in diameter, Sigma) and the cell extract was centrifuged for 20 min at 20,000×g to remove cellular debris. The supernatant was subjected to ultracentrifugation at 100,000×g for 60 min and the resultant pellet contained the microsomal fraction. The microsomal fraction was suspended in TEG-M buffer (50 mM Tris-HCl, pH 7.5, 1 mM EDTA, 20% glycerol and 1.5 mM 2-mercaptoethanol) at protein concentration of 1 mg/mL. Microsomal preparations were stored in a liquid nitrogen freezer until use.

6. Enzyme Activity Assay in Yeast Microsomal Preparations

Nicotine demethylase activity assays with yeast microsomal preparations were performed. In particular, DL-Nicotine (Pyrrolidine-2-$^{14}$C) was obtained from Moravek Biochemicals and had a specific activity of 54 mCi/mmol. Chlorpromazine (CPZ) and oxidized cytochrome c (cyt. C), both P450 inhibitors, were purchased from Sigma. The reduced form of nicotinamide adenine dinucleotide phosphate (NADPH) is the typical electron donor for cytochrome P450 via the NADPH:cytochrome P450 reductase. NADPH was omitted for control incubation. The routine enzyme assay included microsomal proteins (around 1 mg/ml), 6 mM NADPH, and 55 μM $^{14}$C labeled nicotine. The concentration of CPZ and Cyt. C, when used, was 1 mM and 100 μM, respectively. The reaction was carried at 25° C. for 1 hour and was stopped with the addition of 300 μl methanol to each 25 μl reaction mixture. After centrifugation, 20 μl of the methanol extract was separated with a reverse-phase High Performance Liquid Chromatography (HPLC) system (Agilent) using an Inertsil ODS-3 3μ (150×4.6 mm) chromatography column from Varian. The isocratic mobile phase was the mixture of methanol and 50 mM potassium phosphate buffer, pH 6.25, with ratio of 60:40 (v/v) and the flow rate was 1 ml/min. The nornicotine peak, as determined by comparison with authentic non-labeled nornicotine, was collected and subjected to 2900 tri-carb Liquid Scintillation Counter (LSC) (Perkin Elmer) for quantification. The activity of nicotine demethylase is calculated based on the production of $^{14}$C labeled nornicotine over 1 hour incubation.

Microsomal preparations from control yeast cells expressing CYP71D20 did not have any detectable microsomal nicotine demethylase activity. In contrast, microsomal samples obtained from yeast cells expressing the tobacco nicotine demethylase gene showed significant levels of nicotine demethylase activity. The nicotine demethylase activity required NADPH and was shown to be inhibited by p450 specific inhibitors, consistent with tobacco nicotine demethylase being a p450. The enzyme activity for tobacco nicotine demethylase (D121-AA8) was approximately 10.8 pKat/mg protein as calculated by radioactive intensity and protein concentrations. A typical set of enzyme assay results obtained for the yeast cells is shown in the Table 1.

TABLE 1

DEMETHYLASE ACTIVITY IN MICROSOMES OF YEAST CELLS EXPRESSING D121-AA8 AND CONTROL P450

| Sample | Microsomes | Microsomes + 1 mM chlorpromazine | Microsomes + 100 μM cytochrome C | Microsomes − NADPH |
|---|---|---|---|---|
| D121-AA8 | 10.8 ± 1.2* pkat/mg protein | 1.4 ± 1.3 pkat/mg protein | 2.4 ± 0.7 pkat/mg protein | 0.4 ± 0.1 pkat/mg protein |
| Control | Not Detected | Not Detected | Not Detected | Not Detected |

*Average results of 3 replicates.

Together these experiments demonstrated that the cloned full-length tobacco nicotine demethylase (SEQ ID NO:3; D121-AA8) encodes a cytochrome p450 protein that catalyzes the conversion of nicotine to nornicotine when expressed in yeast.

Example 11

Related Amino Acid Sequence Identity of Isolated Nucleic Acid Fragments

The amino acid sequences of nucleic acid sequences obtained for cytochrome p450 fragments from Example 8 were deduced. The deduced region corresponded to the amino acid immediately after the GXRXCP(A/G) (SEQ ID NO:13) sequence motif to the end of the carboxyl-terminus, or stop codon. Upon comparison of sequence identity of the fragments, a unique grouping was observed for those sequences with 70% amino acid identity or greater. A preferred grouping was observed for those sequences with 80% amino acid identity or greater, more preferred with 90% amino acid identity or greater, and a most preferred grouping for those sequences 99% amino acid identity of greater. Several of the unique nucleic acid sequences were found to have complete amino acid identity to other fragments and therefore only one member with the identical amino acid was reported.

At least one member of each amino acid identity group was selected for gene cloning and functional studies using plants. In addition, group members that are differentially affected by ethylene treatment or other biological differences as assessed by Northern and Southern analysis were selected for gene cloning and functional studies. To assist in gene cloning, expression studies and whole plant evaluations, peptide specific antibodies can be prepared based on sequence identity and differential sequence.

Example 12

Related Amino Acid Sequence Identity of Full-Length Clones

The nucleic acid sequence of full-length *Nicotiana* genes cloned in Example 5 were deduced for their entire amino acid sequence. Cytochrome p450 genes were identified by the presence of three conserved p450 domain motifs, which corresponded to UXXRXXZ (SEQ ID NO:14), PXRFXF (SEQ ID NO:15) or GXRXC (SEQ ID NO:16) at the carboxyl-terminus where U is E or K, X is any amino acid and Z is P, T, S or M. All p450 genes were characterized for amino acid identity using a BLAST program comparing their full-length sequences to each other and to known tobacco genes. The program used the NCBI special BLAST tool (Align two sequences (bl2seq), http://www.ncbi.nlm.nih.gov/blast/bl2seq/bl2.html). Two sequences were aligned under BLASTN without filter for nucleic acid sequences and BLASTP for amino acid sequences. Based on their percentage amino acid identity, each sequence was grouped into identity groups where the grouping contained members that shared at least 85% identity with another member. A preferred grouping was observed for those sequences with 90% amino acid identity or greater, a more preferred grouping had 95% amino acid identity or greater, and a most preferred grouping had those sequences 99% amino acid identity or greater. The amino acid sequence of the full-length nicotine demethylase gene was deduced to have the sequence provided in SEQ ID NO:4 (FIG. 3).

Example 13

*Nicotiana* Cytochrome P450 Clones Lacking One or More of the Tobacco P450 Specific Domains Four clones had high nucleic acid homology, ranging 90% to 99% nucleic acid homology. However, due to a nucleotide frameshift these genes did not contain one or more of three C-terminus cytochrome p450 domains and were excluded from identity groups.

Example 14

Use of *Nicotiana* Cytochrome P450 Fragments and Clones in Altered Regulation of Tobacco Qualities The use of tobacco p450 nucleic acid fragments or whole genes are useful in identifying and selecting those plants that have altered tobacco phenotypes or tobacco constituents and, more importantly, altered metabolites. Transgenic tobacco plants are generated by a variety of transformation systems that incorporate nucleic acid fragments or full-length genes, selected from those reported herein, in orientations for either down-regulation, for example anti-sense orientation, or over-expression for example, sense orientation and the like. For over-expression to full-length genes, any nucleic acid sequence that encodes the entire or a functional part or amino acid sequence of the full-length genes described in this invention is desirable. Such nucleic acid sequences desirably are effective for increasing the expression of a certain enzyme and thus resulting in phenotypic effect within *Nicotiana*. *Nicotiana* lines that are homozygous are obtained through a series of backcrossing and assessed for phenotypic changes including, but not limited to, analysis of endogenous p450 RNA, transcripts, p450 expressed peptides and concentrations of plant metabolites using techniques commonly available to one having ordinary skill in the art. The changes exhibited in the tobacco plants provide information on the functional role of the selected gene of interest or are of use as preferred *Nicotiana* plant species.

Example 15

Cloning of the Genomic Tobacco Nicotine Demethylase from Converter Burley Tobacco Genomic DNA was extracted from converter Burley tobacco plant line 4407-33 (a *Nicotiana tabacum* variety 4407 line) using Qiagen Plant Easy kit as described in above Examples (see also the manufacturer's procedure).

The primers were designed based on the 5' promoter and 3' UTR region cloned in previous examples. The forward primers were 5'-GGC TCT AGA TAA ATC TCT TAA GTT ACT AGG TTC TAA-3' (SEQ ID NO:17) and 5'-TCT CTA AAG TCC CCT TCC-3' (SEQ ID NO:25) and the reverse primers were 5'-GGC TCT AGA AGT CAA TTA TCT TCT ACA AAC CTT TAT ATA TTA GC-3' (SEQ ID NO:18), and 5'-CCA GCA TTC CTC AAT TTC-3' (SEQ ID NO:26). PCR was applied to the 4407-33 genomic DNA with 100 µl of reaction mix. Pfx high fidelity enzyme was used for PCR amplification. The PCR product was visualized on 1% agarose gel after electrophoresis. A single band with molecular weight of approximately 3.5 kb was observed and excised from the gel. The resulting band was purified using a gel purification kit (Qiagen; based on manufacturer's procedure). The purified DNA was digested by enzyme Xba I (NEB; used according to the manufacturer's instructions). The pBluescript plasmid was digested by Xba I using same procedure. The fragment was gel purified and ligated to pBluescript plasmid. The ligation mix was transformed into competent cell GMIO9 and plated onto LB plate containing 100 mg/l of ampicillin with blue/white selection. The white colonies were picked and grown into 10 ml LB liquid media containing ampicillin. The DNA was extracted by miniprep. The plasmid DNA containing the insert was sequenced using a CEQ 2000 sequencer (Beckman, Fullerton, Calif.) based on the manufacturer's procedure. The T3 and T7 primers and 8 other internal primers were used for sequencing. The sequence was assembled and analyzed, thus providing the genomic sequence (SEQ ID NO:1; FIGS. 2-1 to 2-3).

Comparison of the sequence of SEQ ID NO:1 with the sequence of SEQ ID NO:3 allowed the determination of a single intron within the coding portion of the gene (identified as the sequence of SEQ ID NO:5; FIG. 4). As shown in FIG. 1, the genomic structure of the tobacco nicotine demethylase includes two exons flanking a single intron. The first exon spans nucleotides 2010 to 2949 of SEQ ID NO:1, which encode amino acids 1-313 of SEQ ID NO:2, and the second exon spans nucleotides 3947 to 4562 of SEQ ID NO:1, which encode amino acids 314-517 of SEQ ID NO:2. Accordingly, the intron spans nucleotides 2950-3946 of SEQ ID NO:1. The intron sequence is provided in FIG. 4 and is that of SEQ ID NO:5. The translation product of the genomic DNA sequence is provided in FIG. 2-1 as the sequence of SEQ ID NO:2. The tobacco nicotine demethylase amino acid sequence contains an endoplasmic reticulum membrane anchoring motif.

Example 16

Cloning 5' Flanking Sequences (SEQ ID NO:6) and 3'UTR (SEQ ID NO:7) from Converter Tobacco A. Isolation of Total DNA from Converter Tobacco Leaves Tissue Genomic DNA was isolated from leaves of converter tobacco 4407-33. The isolation of DNA was performed using a DNeasy Plant Mini Kit from the company Qiagen, Inc. (Valencia, Calif.) according to the manufacturer's protocol. The manufacturer's manual Dneasy' Plant Mini and DNeasy Plant Maxi Handbook, Qiagen January 2004 is incorporated hereby as reference. The procedure for DNA preparation included the following steps: Tobacco leaf tissue (approximately 20 mg dry weight) was ground to a fine powder under liquid nitrogen for 1 minute. The tissue powder was transferred into a 1.5 ml tube. Buffer AP1 (400 µl) and 4 µl of RNase stock solution (100 mg/ml) were added to a maximum of 100 mg of ground leaf tissue and vortexed vigorously. The mixture was incubated for 10 min at 65° C. and mixed 2-3 times during incubation by inverting tube. Buffer AP2 (130 µl) was then added to the lysate. The mixture was mixed and incubated for 5 min on ice. The lysate was applied to a QIAshredder Mini Spin Column and centrifuged for 2 min (14,000 rpm). The flow-through fraction was transferred to a new tube without disturbing the cell-debris pellet. Buffer AP3/E (1.5 volumes) was then added to the cleared lysate and mixed by pipetting. The mixture (650 µl) from the preceding step including any precipitate was applied to a DNeasy Mini Spin Column. The mixture was centrifuged for 1 min at >6000×g (>8000 rpm) and the flow-through was discarded. This was repeated with the remaining sample and the flow-through and collection tube were discarded. DNeasy Mini Spin Column was placed in a new 2 ml collection tube. Then buffer AW (500 µl) was added to the DNeasy column and centrifuged for 1 min (>8000 rpm). The flow-through was discarded. The collection tube was reused in the next step. Buffer AW (500 µl) was then added to the DNeasy column and centrifuged for 2 min (>14,000 rpm) in order to dry the membrane. The DNeasy column was transferred to a 1.5 ml tube. Then Buffer AE (100 pi) was pipetted onto the DNeasy membrane. The mixture was incubated for 5 min at room temperature (15-25° C.) and then centrifuged for 1 min (>8000 rpm) to elute.

The quality and quantity of the DNA was estimated by running samples on an agarose gel.

B. Cloning of 5' Flanking Sequences of the Structural Gene

A modified inverse PCR method was used to clone 750 nucleotides of the 5' flanking sequences of the structural gene from SEQ ID NO:1. First, appropriate restriction enzymes were selected based on the restriction site in the known sequence fragment and the restriction sites distance downstream of the 5' flanking sequences. Two primers were designed based on this known fragment. The forward primer was located downstream of the reverse primer. The reverse primer was located in the 3' portion of the known fragment.

The cloning procedure included the following steps:

The purified genomic DNA (5 µg) was digested with 20-40 units of the appropriate restriction enzyme (EcoRI and SpeI) in a 50 µl reaction mixture. An agarose gel electrophoresis with a 1/10 volume of the reaction mixture was performed to determine if the DNA was digested to completion. A direct ligation was performed after thorough digestion by ligating overnight at 4° C. A reaction mixture of 200 µl containing 10 µl of digested DNA and 0.2 µl of T4 DNA ligase (NEB) was ligated overnight at 4° C. PCR on the ligation reaction was performed after an artificial small circular genome was obtained. PCR was performed with 10 µl of ligation reaction and 2 primers from known fragments in two different directions in 50 µl reaction mixture. A gradient PCR program with annealing temperatures of 45-56° C. was applied.

Agarose gel electrophoresis was performed to check the PCR reaction. The desired band was cut from the gel and a QIAquick gel purification Kit from QIAGEN was used to purify the band. The purified PCR fragments were ligated into a pGEM-T Easy Vector (Promega, Madison, Wis.) following manufacturer's instructions. The transformed DNA plasmids were extracted by miniprep using SV Miniprep kit (Promega, Madison, Wis.) following the manufacturer's instructions. Plasmid DNA containing the insert was sequenced using a CEQ 2000 sequencer (Beckman, Fullerton, Calif.). Approximately 758 nt (nucleotides 1241-2009 of SEQ ID NO:1) of the 5' flanking sequence were cloned by the method described above.

C. Cloning of the Longer 5' Flanking Sequences (SEQ ID NO:6; FIG. 5) of the Structural Gene BD GenomeWalker Universal Kit (Clontech laboratories, Inc., PaloAlto, Calif.) was used for cloning additional 5' flanking sequence of the structural gene, D121-AA8 according to the manufacturer's user manual. The manufacturer's manual BD GenomeWalker August, 2004 is incorporated hereby as reference. The size and purity of tobacco genomic DNA were tested by running samples on a 0.5% agarose gel. A total of 4 blunt-end reactions (DRA I, STU I, ECOR V, PVU II) were set up for tobacco 33 library genome walking construction. After purification of the digested DNAs, the digested genomic DNAs were ligated to the genome walker adaptor. Primary PCR reactions were applied to the four digested DNAs by using adaptor primer API and the gene specific primer from D121-AA8 (CTCTATTGATAC-TAGCTGGTTTTGGAC; SEQ ID NO:19). The primary PCR products were used directly as templates for the nested PCR. The adaptor nested primer provided by the kit and the nested primer from the known clone D121-AA8 (SEQ ID NO:3) (GGAGGGAGAGTATAACTTACGGATTC; SEQ ID NO:20) were used in the PCR reaction. PCR products were checked by running gel electrophoreses. The desired bands were sliced out from the gel, and the PCR fragments were purified using QlAquick gel purification Kit from QIAGEN. The purified PCR fragments were ligated into a pGEM-T Easy Vector (Promega, Madison, Wis.) following manufacturer's instructions. The transformed DNA plasmids were extracted by miniprep using the SV Miniprep kit (Promega, Madison, Wis.) and following the manufacturer's instructions. Plasmid DNA containing the insert was sequenced using a CEQ 2000 sequencer (Beckman, Fullerton, Calif.). Another approximately 853 nt of the 5' flanking sequence, including nucleotides 399-1240 of SEQ ID NO:1, were cloned by the method described above.

A second round of the genome walking was performed according to the same method with the difference that the following primers GWR1A (5'-AGTAACCGATTGCT-CACGTTATCCTC-3') (SEQ ID NO:21) and GWR2A (5'-CTCTATTCAACCCCACACGTAACTG-3') (SEQ ID NO:22) were used. Another approximately 398 nt of flanking sequence, including nucleotides 1-398 of SEQ ID NO:1, were cloned by this method.

A search for regulatory elements revealed that, in addition to "TATA" box, "CAAT" boxes, and "GAGA" boxes, several MYB-like recognition sites and organ specificity elements are present in the tobacco nicotine demethylase promoter region. Putative elicitor responsive elements and nitrogen-regulated elements, identified using standard methods, are also present in the promoter region.

D. Cloning of 3' Flanking Sequences of the Structural Gene

BD GenomeWalker Universal Kit (Clontech laboratories, Inc., PaloAlto, Calif.) was used for cloning of 3' flanking sequence of the structural gene, D121-AA8 according to the manufacturer's user manual. The cloning procedure is the same as describes in the preceding Section C of this example, except for the gene specific primers. The first primer was designed from close to the end of D121-AA8 structural gene (5'-CTA AAC TCT GGT CTG ATC CTG ATA CTT-3') (SEQ ID NO:23). The nested primer was designed further downstream of primer 1 of the D121-AA8 structural gene (CTA TAC GTA AGG TAA ATC CTG TGG AAC) (SEQ ID NO:24). The final PCR products were checked by gel electrophoreses. The desired bands were excised from the gel. The PCR fragments were purified using QlAquick gel purification Kit from QIAGEN. The purified PCR fragments were ligated into a pGEM-T Easy Vector (Promega, Madison, Wis.) following manufacturer's instructions. The transformed DNA plasmids were extracted by miniprep using SV Miniprep kit (Promega, Madison, Wis.) following manufacturer's instructions. Plasmid DNA containing the insert was sequenced using a CEQ 2000 sequencer (Beckman, Fullerton, Calif.). Approximately 1617 nucleotides of additional 3' flanking sequence (nucleotides 4731-6347 of SEQ ID NO:1) were cloned by the method described above. The nucleic acid sequence of the 3'UTR region is shown in FIG. 6.

WO 03/078577, WO 2004/035745, PCT/US/2004/034218, and PCT/US/2004/034065, and all other references, patents, patent application publications, and patent applications referred to herein are incorporated by reference herein to the same extent as if each of these references, patents, patent application publications, and patent applications were separately incorporated by reference herein.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A tobacco leaf from a transgenic tobacco plant comprising a vector, said vector comprising a nucleotide sequence having 100% sequence identity to 25 or more contiguous nucleotides of SEQ ID NO:1, wherein the transgenic tobacco plant exhibits reduced expression of the nicotine demethylase polypeptide encoded by SEQ ID NO:1 relative to a non-transgenic tobacco plant.

2. The tobacco leaf of claim 1, said nucleotide sequence having at least 91% sequence identity to 100 or more contiguous nucleotides of SEQ ID NO:1.

3. The tobacco leaf of claim 2, said nucleotide sequence having at least 91% sequence identity to 250 or more contiguous nucleotides of SEQ ID NO:1.

4. The tobacco leaf of claim 3, said nucleotide sequence having at least 91% sequence identity to 500 or more contiguous nucleotides of SEQ ID NO:1.

5. The tobacco leaf of claim 1, said nucleotide sequence having at least 91% sequence identity to 50 or more contiguous nucleotides of nucleotides 3947-4562 of SEQ ID NO:1.

6. The tobacco leaf of claim 5, said nucleotide sequence having 100% sequence identity to 50 or more contiguous nucleotides of nucleotides 3947-4562 of SEQ ID NO:1.

7. The tobacco leaf of claim 5, said nucleotide sequence having 91% sequence identity to 100 or more contiguous nucleotides of nucleotides 3947-4562 of SEQ ID NO:1.

8. The tobacco leaf of claim 7, said nucleotide sequence having 100% sequence identity to 100 or more contiguous nucleotides of nucleotides 3947-4562 of SEQ ID NO:1.

9. The tobacco leaf of claim 8, said nucleotide sequence having 100% sequence identity to 250 or more contiguous nucleotides of nucleotides 3947-4562 of SEQ ID NO:1.

10. The tobacco leaf of claim 1, said nucleotide sequence having 91% sequence identity to 50 or more contiguous nucleotides of nucleotides 2010-2949 of SEQ ID NO:1.

11. The tobacco leaf of claim 10, said nucleotide sequence having 100% sequence identity to 50 or more contiguous nucleotides of nucleotides 2010-2949 of SEQ ID NO:1.

12. The tobacco leaf of claim 10, said nucleotide sequence having 91% sequence identity to 100 or more contiguous nucleotides of nucleotides 2010-2949 of SEQ ID NO:1.

13. The tobacco leaf of claim 12, said nucleotide sequence having 100% sequence identity to 100 or more contiguous nucleotides of nucleotides 2010-2949 of SEQ ID NO:1.

14. The tobacco leaf of claim 13, said nucleotide sequence having 100% sequence identity to 250 or more contiguous nucleotides of nucleotides 2010-2949 of SEQ ID NO:1.

15. The tobacco leaf of claim 1, wherein said leaf is a cured leaf.

16. A cured tobacco plant component from a transgenic tobacco plant comprising a vector, said vector comprising a nucleotide sequence having 100% sequence identity to 25 or more contiguous nucleotides of SEQ ID NO:1, said cured tobacco plant component exhibiting a reduced amount of the nicotine demethylase polypeptide encoded by SEQ ID NO:1 relative to the amount in a corresponding cured tobacco plant component obtained from a wild-type non-converter tobacco plant.

17. The cured tobacco plant component of claim 16, wherein said cured tobacco plant component is a tobacco leaf.

18. The cured tobacco plant component of claim 17, wherein said cured tobacco plant component has a reduced level of nornicotine relative to the level in a cured tobacco plant component obtained from a wild-type non-converter tobacco plant.

19. The cured tobacco plant component of claim 17, wherein said cured tobacco plant component is from a dark tobacco, Burley tobacco, flue-cured tobacco, air-cured tobacco, or oriental tobacco plant.

20. A tobacco product comprising the cured tobacco plant component of claim 17.

21. The tobacco product of claim 20, wherein said tobacco product is smokeless tobacco.

22. The tobacco product of claim 21, wherein said tobacco product is a moist or dry snuff.

23. The tobacco product of claim 21, wherein said tobacco product is a chewing tobacco.

24. The tobacco product of claim 20, wherein said tobacco product is a cigarette.

25. The tobacco product of claim 20, wherein said tobacco product is a cigar or cigarillo.

* * * * *

UNITED STATES PATENT AND TRADEMARK OFFICE
CERTIFICATE OF CORRECTION

PATENT NO. : 8,592,663 B2  
APPLICATION NO. : 12/760905  
DATED : November 26, 2013  
INVENTOR(S) : Dongmei Xu Page 1 of 1

It is certified that error appears in the above-identified patent and that said Letters Patent is hereby corrected as shown below:

Title Page, Column 1 (Related U.S. Application Data (60)), please delete "Provisional Application No. 60/556,235, filed on March 24, 2004, and insert --U.S. Provisional Application No. 60/665,451, filed March 24, 2005, U.S. Provisional Application No. 60/665,097, filed March 24, 2005, U.S. Provisional Application No. 60/646,764, filed January 25, 2005, U.S. Provisional Application No. 60/607,357, filed September 3, 2004, and U.S. Provisional Application No. 60/566,235, filed April 29, 2004,-- therefor.

In the Specification

Column 1, Line 18, please delete "60/556,235" and insert --60/566,235-- therefor.

Signed and Sealed this  
Sixth Day of May, 2014

Michelle K. Lee  
*Deputy Director of the United States Patent and Trademark Office*

SEQUENCE LISTING

<160> NUMBER OF SEQ ID NOS: 29

<210> SEQ ID NO 1
<211> LENGTH: 6347
<212> TYPE: DNA
<213> ORGANISM: Nicotiana tabacum

<400> SEQUENCE: 1

```
tctctaaagt cccctccac tttatcttag ctgtgtgatt tctttcagac aaccttattt     60
ttattcagac tcttatttgt attattctag aagctcgtgt acttgtgaca ccagttctgg    120
gatggtattt agatatcgct attattttgg cttattcact tcagttcaga ttttattcca    180
gttatttgat ttctttatta ttaatcaaat tgaattgtta aaaatggtta aaattactcc    240
aatgttggct ttcctagtaa gcgaaatatc aggcgccatc acggtacccg aaggtgagaa    300
tttcagatcg tgacagccgc atctcaaggg gtgtgatgta aacagtttac gatggtgcaa    360
```

```
gcattagtgg ctgcttcgac gacttaaatc cgtaacttat agatcacacg aatacaactt      420
tactatttta acacccagca aattcctgat aaaaacaatt ctaacatagc acatcaaaat      480
gtaaatgatt gaagaaaaag atgacttta tagacagaga aaaaaacagt tacgtgtggg       540
gttgaataga gattgtggct atgctatttc taatattgaa attcaccgac ttttttagtt     600
caatacgaaa agagtaagtg aaaaggtctg aaaaggaaaa ggacaatgcc taaaaggaca      660
cattcagaac acatacactg aatgattcta atttctagtc cgaagatttc tagttcgagg     720
ataacgtgag caatcggtta cttcccatta gcaattgcca actggatgtt tgactattta    780
tgtttctggc caatagagga gaggaatact acgttacgta tggagtttga acccttcaca    840
tcaacttatt aagtgagtta tccctcaatc acgattcaac tatgattccg ctaacttcaa    900
agaatattga gttaattatt caaatgatta gtccaaaatt atttaataaa gttatactat    960 ttctttatt tgtaacatac atcttttgtt tacatattta gttaaatctt agcccaaccc    1020
tatcgttggt tcgactttt ttcttttaat tttgatttat tctgttcggt aatttcgctt    1080
tgtttggctt gaataataac tagtgcataa agtcatatac tctaatattt ttaattgaag    1140
tactcacaaa tacaaaaata aaaaacattc taagctcaca tgatagttga caaatctt     1200 atccaaaaca agaggcggag ccaggatttg aaacttatgg gttcagaatt ctaaatctct    1260
taagttacta ggttctaaat taataattta tacatgttca atgaatttct taagacaaat    1320 acatagttg aacgaaagct actgggttcg gccgaatccg taagttatac tctccctccg    1380
ccccggtcca aaaccagcta gtatcaatag agagagagag agagagagag agataataaa    1440
tttgaccatt gacaatggct tattacttgc ttagagttaa ttggtgaact tagagaatat    1500
aataaggaat atttaaacag atacgtcatc aatccacgag taacgaagta agaaataccc    1560
taaaatcgta gaaacattac gttaaattgc ttgacagcct atctagtaag agtcaaaatc    1620
tactatctat cttgttccgc cattttctta aagaagtaca tgagcttat catccacctc    1680 aacatgaatg caaaagaaaa ttattgtgca acttaatatg ttataatcaa tgatatgtgt    1740
cttgtgtaac aaagtatata tttcgatacg atattaatat gtaggtgtta tattttaaa    1800 tatcaaatat catacttaac accgattttt taaaaactta ggccaattac cctaccaact    1860
aaaatactgt atatcaaaca ctaatgtttt ctatttcggt acgacagttc tctatttacc    1920
atattatgga attatgccca tcctacagtt acctataaaa aggaagttgc cgatagttat    1980
attctcaact tcttatctaa aaatccataa tgctttctcc catagaagcc attgtaggac    2040
tagtaacctt cacatttctc ttcttcttcc tatggacaaa aaatctcaa aaaccttcaa     2100 aacccttacc accgaaaatc cccggaggat ggccggtaat cggccatctt ttccacttca    2160
atgacgacgg cgacgaccgt ccattagctc gaaaactcgg agacttagct gacaaatacg    2220
gccccgtttt cacttttcgg ctaggccttc cccttgtctt agttgtaagc agttacgaag    2280
ctgtaaaaga ctgtttctct acaaatgacg ccatttttc caatcgtcca gcttttcttt     2340
acggcgatta ccttggctac aataatgcca tgctattttt ggccaattac ggaccttact    2400
ggcgaaaaaa tcgaaaatta gttattcagg aagttctctc cgctagtcgt ctcgaaaaat    2460
tcaaacacgt gagatttgca agaattcaag cgagcattaa gaatttatat actcgaattg    2520
atggaaattc gagtacgata aatttaactg attggttaga agaattgaat tttggtctga    2580
tcgtgaagat gatcgctgga aaaaattatg aatccggtaa aggagatgaa caagtggaga    2640
gatttaagaa agcgtttaag gatttttatga ttttatcaat ggagttttgtg ttatgggatg    2700 catttccaat tccattattt aaatgggtgg atttttcaagg gcatgttaag gctatgaaaa    2760
```

```
ggacttttaa agatatagat tctgttttc agaattggtt agaggaacat attaataaaa      2820 gagaaaaat ggaggttaat gcagaaggga atgaacaaga tttcattgat gtggtgcttt      2880
caaaaatgag taatgaatat cttggtgaag gttactctcg tgatactgtc attaaagcaa     2940
cggtgtttgt aagttcatct gtcattttc atttattcac ttttatttg aggagcagac       3000 atgttaataa taatttggag caactgtaaa gttatctatg tgtacaggtt cgagcctcag     3060
gtgcaaccac taatgcttgt attagattat gttgtctgca tcatacccct aattggagtg    3120
tggctcttcc cgaaccctgc aatgctggat gctggatgct ttatgtatca gactgacctt    3180
tttgttaaac tatctaaata ctaaggatga tttaataaaa atatagaatg gtaaacagaa    3240
aaagatgaga ttattttgg ggctatatgg attcgcccgg gctttgggag gtaaaacggt     3300
atctaccagt tgagacttta ctccagaact ttatctcgag agctctgaat aaaaatgaaa    3360
tagtatttac cactccaaaa tctttgatgg taaaaagatg agatataacc tcttataatt    3420
gattgaacca cgttgataga ataaaacttc tttactccca ttcagcataa gaaaaatgaa    3480
accaaacgga attcttctct tttttagggg gaaattcctt aattgcttgt tgaatataga   3540
ttcatgtcgt tattctattt ttaataatga tgaaaatcaa tatagtcaaa gttaatactt    3600
atgtcatttg gtttgcggac aagttatatt ggaactatat aatacgtcta ttatagaata   3660
gtgattattt agaggatata cattttttt ggataaaat ttgatttatt ggattaaaaa      3720
tagaatatac aggtaaggtc taaaacgtgt gtttgctttt acactaaata aacttgacct    3780
cgtacaattc taagaaaata tttgaaataa atgaattatt ttattgttaa tcaattaaaa   3840
aaatcatagt atagatgaga tgtgtgcata cttgacaata actatactaa ctaaaacaag   3900
gtatgtgaat aattgatatt ccttttttaa ttattctttt ttccagagtt tggtcttgga   3960
tgcagcagac acagttgctc ttcacataaa ttggggaatg gcattattga taaacaatca   4020
aaaggccttg acgaaagcac aagaagagat agacacaaaa gttggtaagg acagatgggt   4080
agaagagagt gatattaagg atttggtata cctccaagct attgttaaag aagtgttacg    4140
attatatcca ccaggaccttt tgttagtacc acacgaaaat gtagaagatt gtgttgttag   4200
tggatatcac attcctaaag ggacaagatt attcgcaaac gtcatgaaac tgcaacgtga   4260
tcctaaactc tggtctgatc ctgatacttt cgatccagag agattcattg ctactgatat   4320
tgactttcgt ggtcagtact ataagtatat cccgtttggt tctggaagac gatcttgtcc   4380
agggatgact tatgcattgc aagtggaaca cttaacaatg gcacatttga tccaaggttt   4440
caattacaga actccaaatg acgagccctt ggatatgaag gaaggtgcag gcataactat   4500
acgtaaggta atcctgtgg aactgataat agcgcctcgc ctggcacctg agctttatta    4560
aaacctaaga tctttcatct tggttgatca ttgtataata ctcctaaatg gatattcatt   4620 tacctttat caattaattg tcagtacgag ttttctaat ttggtacatt tgtaataata     4680
agtaaagaat aattgtgcta atatataaag gtttgtagaa gataattgac tggttgtacc    4740
acaatctcca gtgaaagtgt taattattta cttgatccac agcttattct atgtttgaaa   4800
tttgcctagt gtcatgatat tactccatca aattcaagaa ataatcattt ccaacttttg   4860
ctggactgga cgatctttca ataataaagg atctttaatt tgccaaagtt gagatcaaaa   4920
tactggtcgc tttaccaata agaatgaaat gtgatgaaa ttatgtacgt tgggataagg    4980
gaacacaact atcaaggaga ctaaaaggta cgtaaaggaa agaaaaaat ttgccattga    5040 ttgctactaa gtaacctaac aaaatctttc agaaaagaat cacttgtata agtcggggtt   5100
gaaagttttg gtgtctcttt tcttatgtat tgttgtcttt agacagtatt gtacttagtt   5160
```

```
atttcagaat tttatttcg tattagagct caagactctg tatttattag ttctgggaga    5220
attatcatgt attttcagtc ttttgttatt tctgtaaatt ccgctatttt ggttctttat    5280
tgctatgttc ggcttccta gaaaatgtgt taggcgctat cacgactgat tgagattttg    5340
tatcgtgact gataattaca cggtttagta aattttgata ttttcaaaaa gagttttttt    5400
aataaaatat gcaacttcag tcaaaacata caacgttttg ttgtataaat ccgatcaaaa    5460
catataactt acataaaact tgcgtatgaa ttttttgttg tataaacatt tggttaaaac    5520
atataactta catataattt gcatacaact tacataaaac ttgcatataa acaatttatt    5580
tatgtctttg ttttgagta tcaattgaa attccaacaa aaacaaactc taatttttac    5640
caaactctct caaaattgag ttatagattt caaaagatat ccttaatcgt ttgcaattgt    5700
aacaatccga tcggccgttt tgagatctag cgtgttgttt ggcggtttga gaccttgagt    5760
aacttcactt tatgttgtat gacttgtata tgtggtcgga attaaatttc gggaagttca    5820
gagttgattc ggatgaaaaa ttctaatttc ggaagttta agatggaatg attgactaag    5880
gattgacgtt tgagtaaacg atctcggaat cgagatttga aggttccaat aggttcgtat    5940
gatgatttca gacttgagcg tatgtttggg ttgagtatcg ggtggtccgg gagcatttca    6000
acgctgatta tagaaaattg gcatcttaaa ggttttagaa tttcataagt ttggtttgaa    6060
gtggattttg atattatcgg tgtccatttg gagtttcgag ccttggaata ggttcgtatc    6120
gtaaattttg actttagtgt aaagttcggc gtcattccgg agtgttttga taagattctg    6180
atgcgttcgt cgaagtttgg aagtttgaaa gttgaaaaga agattttttaa taggcgattc    6240 atgattttga tgttatttgt gtcgagcctt tggataagtt tgtgtgaggt atgggacttg    6300
ttggtatgaa tggacgagct ctacgggggc ctcgagtaag tttcgga               6347

<210> SEQ ID NO 2
<211> LENGTH: 517
<212> TYPE: PRT
<213> ORGANISM: Nicotiana tabacum

<400> SEQUENCE: 2

Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

His Phe Asn Asp Asp Gly Asp Asp Arg Pro Leu Ala Arg Lys Leu Gly
         50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
```

```
                    165                 170                 175
Ile Asn Leu Thr Asp Trp Leu Glu Glu Leu Asn Phe Gly Leu Ile Val
                180                 185                 190

Lys Met Ile Ala Gly Lys Asn Tyr Glu Ser Lys Gly Asp Glu Gln
        195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
        260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
        340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
        420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
        500                 505                 510

Ala Pro Glu Leu Tyr
        515

<210> SEQ ID NO 3
<211> LENGTH: 1554
<212> TYPE: DNA
<213> ORGANISM: Tobacco Nicotine Demethylase Gene Coding Sequence

<400> SEQUENCE: 3
atgctttctc ccatagaagc cattgtagga ctagtaacct tcacatttct cttcttcttc      60
ctatggacaa aaaatctca aaaaccttca aaacccttac caccgaaaat ccccggagga     120
```

-continued

```
tggccggtaa tcggccatct tttccacttc aatgacgacg gcgacgaccg tccattagct    180
cgaaaactcg gagacttagc tgacaaatac ggccccgttt tcactttcg gctaggcctt    240
ccccttgtct tagttgtaag cagttacgaa gctgtaaaag actgtttctc tacaaatgac    300
gccatttttt ccaatcgtcc agcttttctt tacggcgatt accttggcta caataatgcc    360
atgctatttt tggccaatta cggaccttac tggcgaaaaa atcgaaaatt agttattcag    420
gaagttctct ccgctagtcg tctcgaaaaa ttcaaacacg tgagatttgc aagaattcaa    480
gcgagcatta agaatttata tactcgaatt gatggaaatt cgagtacgat aaatttaact    540
gattggttag aagaattgaa ttttggtctg atcgtgaaga tgatcgctgg aaaaaattat    600
gaatccggta aaggagatga acaagtggag agatttaaga aagcgtttaa ggattttatg    660
attttatcaa tggagtttgt gttatgggat gcatttccaa ttccattatt aaatgggtg    720
gattttcaag ggcatgttaa ggctatgaaa aggacttta aagatataga ttctgttttt    780
cagaattggt tagaggaaca tattaataaa agagaaaaaa tggaggttaa tgcagaaggg    840
aatgaacaag atttcattga tgtggtgctt tcaaaaatga gtaatgaata tcttggtgaa    900
ggttactctc gtgatactgt cattaaagca acggtgttta gtttggtctt ggatgcagca    960
gacacagttg ctcttcacat aaattgggga atggcattat tgataaacaa tcaaaaggcc   1020
ttgacgaaag cacaagaaga gatagacaca aaagttggta aggacagatg ggtagaagag   1080
agtgatatta aggatttggt atacctccaa gctattgtta agaagtgtt acgattatat   1140
ccaccaggac ctttgttagt accacacgaa aatgtagaag attgtgttgt tagtggatat   1200
cacattccta aagggacaag attattcgca aacgtcatga aactgcaacg tgatcctaaa   1260
ctctggtctg atcctgatac tttcgatcca gagagattca ttgctactga tattgacttt   1320
cgtggtcagt actataagta tatcccgttt ggttctggaa gacgatcttg tccagggatg   1380
acttatgcat tgcaagtgga acacttaaca atggcacatt tgatccaagg tttcaattac   1440
agaactccaa atgacgagcc cttggatatg aaggaaggtg caggcataac tatacgtaag   1500
gtaaatcctg tggaactgat aatagcgcct cgcctggcac ctgagctta ttaa           1554
```

<210> SEQ ID NO 4
<211> LENGTH: 517
<212> TYPE: PRT
<213> ORGANISM: Tobacco Nicotine Demethylase Gene

<400> SEQUENCE: 4

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125
```

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 5
<211> LENGTH: 998
<212> TYPE: DNA
<213> ORGANISM: Tobacco Nicotine Demethylase gene intron

<400> SEQUENCE: 5

```
gtaagttcat ctgtcatttt tcatttattc acttttattt tgaggagcag acatgttaat    60
aataatttgg agcaactgta aagttatcta tgtgtacagg ttcgagcctc aggtgcaacc   120
actaatgctt gtattagatt atgttgtctg catcataccc ctaattggag tgtggctctt   180
cccgaaccct gcaatgctgg atgctggatg ctttatgtat cagactgacc ttttgttaa    240
actatctaaa tactaaggat gatttaataa aaatatagaa tggtaaacag aaaaagatga   300
gattattttt ggggctatat ggattcgccc gggctttggg aggtaaaacg gtatctacca   360
gttgagactt tactccagaa ctttatctcg agagctctga ataaaaatga aatagtattt   420
accactccaa atctttgat ggtaaaaaga tgagatataa cctcttataa ttgattgaac    480
cacgttgata gaataaaact tctttactcc cattcagcat aagaaaaatg aaaccaaacg   540
gaattcttct cttttttagg gggaaattcc ttaattgctt gttgaatata gattcatgtc   600
gttattctat ttttaataat gatgaaaatc aatatagtca aagttaatac ttatgtcatt   660
tggtttgcgg acaagttata ttggaactat ataatcgtc tattatagaa tagtgattat    720
ttagaggata tacatttttt ttggataaat atttgattta ttggattaaa aatagaatat   780
acaggtaagg tctaaaacgt gtgtttgctt ttacactaaa taaacttgac ctcgtacaat   840
tctaagaaaa tatttgaaat aaatgaatta ttttattgtt aatcaattaa aaaaatcata   900
gtatagatga gatgtgtgca tacttgacaa taactatact aactaaaaca aggtatgtga   960
ataattgata ttccttttt aattattctt ttttccag                            998
```

<210> SEQ ID NO 6
<211> LENGTH: 2009
<212> TYPE: DNA
<213> ORGANISM: Tobacco Nicotine Demethylase gene promoter

<400> SEQUENCE: 6

```
tctctaaagt cccttccac tttatcttag ctgtgtgatt tctttcagac aaccttattt    60
ttattcagac tcttattgt attattctag aagctcgtgt acttgtgaca ccagttctgg   120
gatggtattt agatatcgct attatttgg cttattcact tcagttcaga ttttattcca   180
gttatttgat ttcttattta ttaatcaaat tgaattgtta aaaatggtta aaattactcc   240
aatgttggct ttcctagtaa gcgaaatatc aggcgccatc acggtacccg aaggtgagaa   300
tttcagatcg tgacagccgc atctcaaggg gtgtgatgta aacagtttac gatggtgcaa   360
gcattagtgg ctgcttcgac gacttaaatc cgtaacttat agatcacacg aatacaactt   420
tactatttta acacccagca aattcctgat aaaaacaatt ctaacatagc acatcaaaat   480
gtaaatgatt gaagaaaaag atgactttta tagacagaga aaaaacagt tacgtgtggg    540
gttgaataga gattgtggct atgctatttc taatattgaa attcaccgac ttttttagtt   600
caatacgaaa agagtaagtg aaaggtctg aaaggaaaa ggacaatgcc taaaaggaca    660
cattcagaac acatacactg aatgattcta atttctagtc cgaagatttc tagttcgagg   720
ataacgtgag caatcggtta cttcccatta gcaattgcca actggatgtt tgactattta   780
tgtttctggc caatagagga gaggaatact acgttacgta tggagtttga acccttcaca   840
tcaacttatt aagtgagtta tccctcaatc acgattcaac tatgattccg ctaacttcaa   900
agaatattga gttaattatt caaatgatta gtccaaaatt atttaataaa gttatactat   960
ttctttttatt tgtaacatac atctttttgtt tacatattta gttaaatctt agcccaaccc  1020
tatcgttggt tcgactttt ttcttttaat tttgatttat tctgttcggt aatttcgctt   1080
```

```
tgtttggctt gaataataac tagtgcataa agtcatatac tctaatattt ttaattgaag    1140
tactcacaaa tacaaaaata aaaaacattc taagctcaca tgatagttga caaaatcttt    1200
atccaaaaca agaggcggag ccaggatttg aaacttatgg gttcagaatt ctaaatctct    1260
taagttacta ggttctaaat taataattta tacatgttca atgaatttct taagacaaat    1320
acatagtttg aacgaaagct actgggttcg gccgaatccg taagttatac tctccctccg    1380
ccccggtcca aaaccagcta gtatcaatag agagagagag agagagagag agataataaa    1440
tttgaccatt gacaatggct tattacttgc ttagagttaa ttggtgaact tagagaatat    1500
aataaggaat atttaaacag atacgtcatc aatccacgag taacgaagta agaaatacccc    1560 taaaatcgta gaaacattac gttaaattgc ttgacagcct atctagtaag agtcaaaatc    1620
tactatctat cttgttccgc cattttctta aagaagtaca tgagctttat catccacctc    1680
aacatgaatg caaagaaaaa ttattgtgca acttaatatg ttataatcaa tgatatgtgt    1740
cttgtgtaac aaagtatata tttcgatacg atattaatat gtaggtgtta tattttaaa    1800 tatcaaatat catacttaac accgattttt taaaaactta ggccaattac cctaccaact    1860
aaaatactgt atatcaaaca ctaatgtttt ctatttcggt acgacagttc tctatttacc    1920
atattatgga attatgccca tcctacagtt acctataaaa aggaagttgc cgatagttat    1980
attctcaact tcttatctaa aaatccata                                      2009

<210> SEQ ID NO 7
<211> LENGTH: 1786
<212> TYPE: DNA
<213> ORGANISM: Tobacco Nicotine Demethylase gene 3' UTR

<400> SEQUENCE: 7
aacctaagat ctttcatctt ggttgatcat tgtataatac tcctaaatgg atattcattt     60
accttttatc aattaattgt cagtacgagt ttttctaatt tggtacattt gtaataataa    120
gtaaagaata attgtgctaa tatataaagg tttgtagaag ataattgact ggttgtacca    180
caatctccag tgaaagtgtt aattatttac ttgatccaca gcttattcta tgtttgaaat    240
ttgcctagtg tcatgatatt actccatcaa attcaagaaa taatcatttc caacttttgc    300
tggactggac gatcttttcaa taataaagga tcttaattt gccaaagttg agatcaaaat    360
actggtcgct ttaccaataa gaatgaaatg tgatggaaat tatgtacgtt gggataaggg    420
aacacaacta tcaaggagac taaaaggtac gtaaaggaaa agaaaaaatt tgccattgat    480
tgctactaag taacctaaca aaatctttca gaaaagaatc acttgtataa gtcggggttg    540
aaagttttgg tgtctctttt cttatgtatt gttgtctta gacagtattg tacttagtta    600
tttcagaatt ttattttcgt attagagctc aagactctgt atttattagt tctgggagaa    660
ttatcatgta ttttcagtct tttgttattt ctgtaaattc cgctattttg gttctttatt    720
gctatgttcg gctttcctag aaaatgtgtt aggcgctatc acgactgatt gagattttgt    780
atcgtgactg ataattacac ggtttagtaa atttgtgatat ttttcaaaaag agtttttta    840 ataaaatatg caacttcagt caaaacatac aacgttttgt tgtataaatc cgatcaaaac    900
atataactta cataaaactt gcgtatgaat tttttgttgt ataaacattt ggttaaaaca    960
tataacttac atataatttg catacaactt acataaaact tgcatataaa caattttattt   1020 atgtctttgt tttgagtat caatttgaaa ttccaacaaa aacaaactct aatttttacc    1080
aaactctctc aaaattgagt tatagatttc aaaagatatc cttaatcgtt tgcaattgta    1140
acaatccgat cggccgtttt gagatctagc gtgttgtttg gcggtttgag accttgagta    1200
```

```
acttcactttt  atgttgtatg  acttgtatat  gtggtcggaa  ttaaatttcg  ggaagttcag      1260
agttgattcg  gatgaaaaat  tctaatttcg  gaagttttaa  gatggaatga  ttgactaagg      1320
attgacgttt  gagtaaacga  tctcggaatc  gagatttgaa  ggttccaata  ggttcgtatg      1380
atgatttcag  acttgagcgt  atgtttgggt  tgagtatcgg  gtggtccggg  agcatttcaa      1440
cgctgattat  agaaaattgg  catcttaaag  gttttagaat  tcataagttt  tggtttgaag      1500 tggatttttga  tattatcggt  gtccatttgg  agtttcgagc  cttggaatag  gttcgtatcg      1560
taaattttga  ctttagtgta  aagttcggcg  tcattccgga  gtgttttgat  aagattctga      1620
tgcgttcgtc  gaagtttgga  agtttgaaag  ttgaaaagaa  gatttttaat  aggcgattca      1680 tgatttttgat  gttatttgtg  tcgagccttt  ggataagttt  gtgtgaggta  tgggacttgt      1740
tggtatgaat  ggacgagctc  tacgggggcc  tcgagtaagt  ttcgga                      1786
```

<210> SEQ ID NO 8
<211> LENGTH: 21
<212> TYPE: PRT
<213> ORGANISM: Artificial Sequence
<220> FEATURE:
<223> OTHER INFORMATION: Synthesized peptide

<400> SEQUENCE: 8

Asp Ile Asp Gly Ser Lys Ser Lys Leu Val Lys Ala His Arg Lys Ile
1               5                   10                  15

Asp Glu Ile Leu Gly
            20

<210> SEQ ID NO 9
<211> LENGTH: 20
<212> TYPE: PRT
<213> ORGANISM: Artificial Sequence
<220> FEATURE:
<223> OTHER INFORMATION: Synthesized peptide

<400> SEQUENCE: 9

Arg Asp Ala Phe Arg Glu Lys Glu Thr Phe Asp Glu Asn Asp Val Glu
1               5                   10                  15

Glu Leu Asn Tyr
            20

<210> SEQ ID NO 10
<211> LENGTH: 22
<212> TYPE: PRT
<213> ORGANISM: Artificial Sequence
<220> FEATURE:
<223> OTHER INFORMATION: Synthesized peptide

<400> SEQUENCE: 10

Phe Lys Asn Asn Gly Asp Glu Asp Arg His Phe Ser Gln Lys Leu Gly
1               5                   10                  15

Asp Leu Ala Asp Lys Tyr
            20

<210> SEQ ID NO 11
<211> LENGTH: 6
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (2)..(2)
<223> OTHER INFORMATION: Xaa = any amino acid

```
<400> SEQUENCE: 11

Phe Xaa Pro Glu Arg Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Ala or Gly

<400> SEQUENCE: 12

Gly Arg Arg Xaa Cys Pro Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Ala or Gly

<400> SEQUENCE: 13

Gly Xaa Arg Xaa Cys Pro Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (1)..(1)
<223> OTHER INFORMATION: Xaa = Glu or Lys
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Pro, Thr, Ser, or, Met

<400> SEQUENCE: 14

Xaa Xaa Xaa Arg Xaa Xaa Xaa
1               5
```

<210> SEQ ID NO 15
<211> LENGTH: 6
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid

<400> SEQUENCE: 15

Pro Xaa Arg Phe Xaa Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Consensus Sequence Conserved p450 Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 16

Gly Xaa Arg Xaa Cys
1               5

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
ggctctagat aaatctctta agttactagg ttctaa                         36

<210> SEQ ID NO 18
<211> LENGTH: 44
<212> TYPE: DNA
<213> ORGANISM: Artificial Sequence
<220> FEATURE:
<223> OTHER INFORMATION: Primer

<400> SEQUENCE: 18
ggctctagaa gtcaattatc ttctacaaac ctttatatat tagc                44

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
ctctattgat actagctggt tttggac                                   27

-continued

```
<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ggagggagag tataacttac ggattc                                          26

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
agtaaccgat tgctcacgtt atcctc                                          26

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
ctctattcaa ccccacacgt aactg                                           25

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
ctaaactctg gtctgatcct gatactt                                         27

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
ctatacgtaa ggtaaatcct gtggaac                                         27

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
tctctaaagt ccccttcc                                                   18

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26
```

```
ccagcattcc tcaatttc                                              18

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
tagctacgcg gatccatgct ttctcccata gaagcc                          36

<210> SEQ ID NO 28
<211> LENGTH: 64
<212> TYPE: DNA
<213> ORGANISM: Artificial Sequence
<220> FEATURE:
<223> OTHER INFORMATION: Primer

<400> SEQUENCE: 28
ctggatcaca attgttagtg atggtgatgg tgatgcgatc ctctataaag ctcaggtgcc 60
aggc                                                             64

<210> SEQ ID NO 29
<211> LENGTH: 7
<212> TYPE: PRT
<213> ORGANISM: Artificial Sequence
<220> FEATURE:
<223> OTHER INFORMATION: Consensus Sequence For Conserved p450 Motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Gly or Ala

<400> SEQUENCE: 29

Gly Xaa Arg Xaa Cys Xaa Xaa
1               5
```